(12) United States Patent
Dmitrovsky et al.

(10) Patent No.: US 8,207,325 B2
(45) Date of Patent: Jun. 26, 2012

(54) MICRORNA BIOMARKERS FOR HUMAN BREAST AND LUNG CANCER

(75) Inventors: Ethan Dmitrovsky, Hanover, NH (US); Xi Liu, Lebanon, NH (US); Sarah Freemantle, Hanover, NH (US); Lorenzo Sempere, Elche (ES); Charles Cole, Thetford, VT (US); Sakari Kauppinen, Smoerum (DK); Mads Bak, Vanloese (DK); Mette Christensen, Valby (DK)

(73) Assignees: Univ. of Copenhagen, Copenhagen K (DK); Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 12/436,576

(22) Filed: May 6, 2009

(65) Prior Publication Data

US 2010/0010072 A1 Jan. 14, 2010

Related U.S. Application Data

(63) Continuation-in-part of application No. 11/730,570, filed on Apr. 2, 2007.

(60) Provisional application No. 60/788,067, filed on Apr. 3, 2006.

(51) Int. Cl.
*C07H 21/04* (2006.01)
(52) U.S. Cl. .................. 536/24.5; 536/24.1; 536/24.31; 514/44
(58) Field of Classification Search .................. None
See application file for complete search history.

(56) References Cited

U.S. PATENT DOCUMENTS

| 7,683,036 | B2 * | 3/2010 | Esau et al. ................. 514/44 R |
| 2005/0059005 | A1 | 3/2005 | Tuschl et al. |
| 2005/0182005 | A1 | 8/2005 | Tuschl et al. |
| 2005/0221293 | A1 | 10/2005 | Tuschl et al. |
| 2005/0260648 | A1 | 11/2005 | Huffel et al. |
| 2005/0261218 | A1 * | 11/2005 | Esau et al. ..................... 514/44 |
| 2005/0272075 | A1 | 12/2005 | Jacobsen et al. |
| 2006/0105360 | A1 * | 5/2006 | Croce et al. ................... 435/6 |
| 2007/0050146 | A1 | 3/2007 | Bentwich et al. |

FOREIGN PATENT DOCUMENTS

| JP | 2005-296014 A | 10/2005 |
| WO | WO 03/029459 A2 | 4/2003 |
| WO | WO 2004/076622 A2 | 9/2004 |
| WO | WO 2005/013901 A2 | 2/2005 |
| WO | WO 2005/040419 A1 | 5/2005 |
| WO | WO 2005/054494 A2 | 6/2005 |
| WO | WO 2005/056797 A1 | 6/2005 |
| WO | WO 2005/078096 A2 | 8/2005 |
| WO | WO 2005/092393 A1 | 10/2005 |
| WO | WO 2005/098029 A2 | 10/2005 |
| WO | WO 2005/103298 A2 | 11/2005 |

OTHER PUBLICATIONS

Bandres et al. (Molecular Cancer 2006; 5(29) 1-10.*
Doe, Jenna Marie, "MicroRNA:Cancer and Future Treatment Applications", *MMG 445Basic Biotechnology EJournal*, vol. 4, pp. 36-42, 2008.
Liu, et al., "MicroRNA-31 functions as an oncogenic microRNA in mouse and human lung cancer cells by repressing specific tumor suppressors", *The Journal of Clinical Investigation*, vol. 120(4), pp. 1298-1309, Apr. 2010.
Lee P. Lim et al., "Vertebrate MicroRNA Genes", *Science*, vol. 299, p. 1540, Mar. 7, 2003.
M. Z. Michael et a., "Reduced Accumulation of Specific MicroRNAs in Colorectal Neoplasia", *Molecular Cancer Research*, vol. 1, pp. 882-891, Oct. 2003.
J. A. Chan et al., "MicroRNA-2 Is an Antiapoptotic Factor in Human Glioblastoma Cells", *Cancer Research*, vol. 65, No. 14, pp. 6029-6033, Jul. 15, 2005.
I. Bentwich et al., "Identification of hundreds of conserved and nonconserved human microRNAs", *Nature Genetics*, vol. 37, No. 7, pp. 776-770, Jul. 2005.
M. V. Iorio et al., "MicroRNA Gene Expression Deregulation in Human Breast Cancer", *Cancer Research*, vol. 65, No. 16, pp. 7065-7070, Aug. 15, 2005.
I. Bentwich. "Prediciton and validation of microRNAs and their targets", *FEBS Letters*, No. 579, pp. 5904-5910, 2005.

* cited by examiner

*Primary Examiner* — Kimberly Chong
(74) *Attorney, Agent, or Firm* — Licata & Tyrell P.C.

(57) ABSTRACT

The present invention relates to novel molecular markers for diagnosis and classification of human breast cancer and lung cancer.

8 Claims, 16 Drawing Sheets

A

B

A

B

MICRORNA BIOMARKERS FOR HUMAN BREAST AND LUNG CANCER

This application is a continuation-in-part of 11/730,570, filed Apr. 2, 2007, which claims benefit under 35 USC 119(e) of provisional application 60/788,067, filed Apr. 3, 2006.

All patent and non-patent references cited in the application, are also hereby incorporated by reference in their entirety.

This invention was made with government support under CA111422, CA087546, and CA130102 awarded by the National Institutes of Health. The government has certain rights in the invention.

BACKGROUND OF INVENTION

MicroRNAs —Novel Regulators of Gene Expression

MicroRNAs (miRNAs) are an abundant class of short endogenous RNAs that act as post-transcriptional regulators of gene expression by base-pairing with their target mRNAs. The ~22 nucleotide (nt) mature miRNAs are processed sequentially from longer hairpin transcripts (primary miRNA/pri-miRNA or precursor miRNA) by the RNAse III ribonucleases Drosha (Lee et al. 2003) and Dicer (Hutvagner et al. 2001, Ketting et al. 2001). To date more than 3400 miRNAs have been annotated in vertebrates, invertebrates and plants according to the miRBase microRNA database re-lease 7.1 in October 2005 (Griffith-Jones 2004, Griffith-Jones et al. 2006), and many miRNAs that correspond to putative miRNA genes have also been bioinformatically predicted. More than half of all known mammalian miRNAs are hosted within the introns of pre-mRNAs or long ncRNA transcripts (Rodriquez et al. 2004). Many miRNA genes are arranged in genomic clusters (Lagos-Quintana et al. 2001). For example, ca. 40% of human miRNA genes appear in clusters of two or more, with the largest cluster of 40 miRNA genes being located in the human imprinted 14q32 domain (Setiz et al. 2004; Altuvia et al. 2005). In plants, 117 miRNA genes have been identified in *Arabidopsis thaliana* while number of miRNAs identified in rice is currently 178 (Griffith-Jones 2004, Griffith-Jones et al. 2006). The identified miRNAs to date represent most likely the tip of the iceberg, and the number of miRNAs might turn out to be very large. Recent bioinformatic predictions combined with array analyses, small RNA cloning and Northern blot validation indicate that the total number of miRNAs in vertebrate genomes is significantly higher than previously estimated and may be as many as 1000 (Bentwich et al. 2005, Berezikov et al. 2005, Xie et al. 2005).

The first miRNAs genes to be discovered, lin-4 and let-7, base-pair incompletely to repeated elements in the 3' untranslated regions (UTRs) of heterochronic genes, and control developmental timing in *C. elegans* by regulating translation directly and negatively via antisense RNA-RNA interaction (Lee et al. 1993, Reinhart et al. 2000). The majority of plant miRNAs have perfect or near-perfect complementarity with their target sites and direct RISC-mediated target mRNA cleavage (for review, see Bartel 2004). A large fraction of the plant miRNAs appear to regulate genes with roles in developmental processes, such as control of meristem identity, cell proliferation, developmental timing and patterning (Kidner and Martienssen 2005). In contrast, most animal miRNAs recognise their target sites located in 3'-UTRs by incomplete base-pairing, resulting in translational repression of the target genes (Bartel 2004). An increasing body of research shows that animal miRNAs play fundamental biological roles in cell growth and apoptosis (Brennecke et al. 2003), hematopoietic lineage differentiation (Chen et al. 2004), life-span regulation (Boehm and Slack 2005), photoreceptor differentiation (Li and Carthew 2005), homeobox gene regulation (Yekta et al. 2004, Hornstein et al. 2005), neuronal asymmetry (Johnston et al. 2004), insulin secretion (Poy et al. 2004), brain morphogenesis (Giraldez et al. 2005), muscle proliferation and differentiation (Chen, Mandel et al. 2005, Kwon et al. 2005, Sokol and Ambros 2005), cardiogenesis (Zhao et al. 2005) and late embryonic development in vertebrates (Wienholds et al. 2005). Several studies have identified sub-classes of miRNAs directly implicated in the regulation of mammalian brain development and neuronal differentiation (Krichevsky et al. 2003, Miska et al. 2004, Sempere et al. 2004, Smirnova et al. 2005). Interestingly, many neural miRNAs appear to be temporally regulated in cortical cultures copurifying with polyribosomes, suggesting that they may control localized translation of dendrite-specific mRNAs (Kim et al. 2004).

The number of regulatory mRNA targets of vertebrate miRNAs has been estimated by identifying conserved complementarity to the miRNA seed sequences (nucleotide 2-7 of the miRNA), suggesting that ~30% of the human genes may be miRNA targets (Lewis et al. 2005). Computational predictions in *Drosophila* provide evidence that a given miRNA has on average ~100 mRNA target sites in the fly, while another recent study reported that vertebrate miRNAs may target ~200 mRNAs each, further supporting the notion that miRNAs can regulate the expression of a large fraction of the protein-coding genes in multicellular eukaryotes (Brennecke et al. 2005, Krek et al. 2005). Most recent reports indicate that miRNAs may not function as developmental switches, but rather play a role in maintaining tissue identity by conferring accuracy to gene-expression programs (Giraldez et al. 2005, Lim et al. 2005, Stark et al. 2005, Farh et al. 2005, Wienholds et al. 2005).

MicroRNAs in Human Disease

The expanding inventory of human miRNAs along with their highly diverse expression patterns and high number of potential target mRNAs suggest that miRNAs are involved in a wide variety of human diseases. One is spinal muscular atrophy (SMA), a paediatric neurodegenerative disease caused by reduced protein levels or loss-of-function mutations of the survival of motor neurons (SMN) gene (Paushkin et al. 2002). A mutation in the target site of miR-189 in the human SLITRK1 gene was recently shown to be associated with Tourette's syndrome (Abelson et al. 2005), while another recent study reported that the hepatitis C virus (HCV) RNA genome interacts with a host-cell miRNA, the liver-specific miR-122a, to facilitate its replication in the host (Jopling et al. 2005). Other diseases in which miRNAs or their processing machinery have been implicated, include fragile X mental retardation (FXMR) caused by absence of the fragile X mental retardation protein (FMRP) (Nelson et al. 2003, Jin et al. 2004) and DiGeorge syndrome (Landthaler et al. 2004). In addition, perturbed miRNA expression patterns have been reported in many human cancers. For example, the human miRNA genes miR-15a and miR-16-1 are deleted or down-regulated in the majority of B-cell chronic lymphocytic leukemia (CLL) cases, where a unique signature of 13 miRNA genes was recently shown to associate with prognosis and progression (Calin et al. 2002, Calin et al. 2005). The role of miRNAs in cancer is further supported by the fact that more than 50% of the human miRNA genes are located in cancer-associated genomic regions or at fragile sites (Calin et al. 2004). Recently, systematic expression analysis of a diversity of human cancers revealed a general down-regulation of miRNAs in tumours compared to normal tissues (Lu et al. 2005). Interestingly, miRNA-based classification of poorly differentiated tumours was successful, whereas mRNA profiles were highly inaccurate when applied to the same samples. miRNAs have also been shown to be deregulated in lung cancer (Johnson et al. 2005) and colon cancer (Michael et al. 2004), while the miR-17~92 cluster, which is amplified in human B-cell lymphomas and miR-155 which is upregulated in Burkitt's lymphoma have been reported as the first human miRNA oncogenes (E is et al. 2005, He et al. 2005). Thus, human miRNAs may not only be highly useful as biomarkers for future cancer diagnostics, but are rapidly emerging as attractive targets for disease intervention by antisense oligonucleotide technologies.

Human Breast Cancer

Breast cancer is one of the most common cancers of women; it is a complex, inadequately understood, and often a fatal disease. Studies in many laboratories over the past few decades have demonstrated that breast cancer (and indeed cancer in general) results from a series of mutations affecting multiple classes of genes. Natural selection favours the growth of cells containing mutations that confer growth advantages and prevent the functioning of normal growth inhibitory mechanisms such as apoptosis. Mutations affecting both proto-oncogenes and tumour suppressor genes contribute to breast cancer and affect diverse cellular processes including signal transduction, DNA replication and repair, transcription, translation, apoptosis and differentiation. Factors known to be important for characterization, diagnosis and prognosis of breast tumours include the status of the estrogen receptor (ER), epithelial growth factor receptor (EGFR), human EGF receptor 2 (HER2) and p53, and some of these can be used as targets for therapeutic intervention (Colozza et al., 2005). From a clinical perspective, ER and HER2 are considered the main molecular targets, since effective drugs exist to treat these tumour types: tamoxifen and aromatase inhibitors for ER+ tumours and Herceptin for HER2-overexpressing tumours, respectively.

Human Lung Cancer

Lung cancer is the leading cause of cancer deaths in both women and men in the United States and throughout the world. Lung cancer is the number one cause of cancer deaths in men and has surpassed breast cancer as the leading cause of cancer deaths in women. In the United States in 2004, 160,440 people were projected to die from lung cancer compared with a projected 127,210 deaths from colorectal, breast, and prostate cancer combined. Only about 14% of all people who develop lung cancer survive for 5 years.

The lungs are a common site for metastasis, i.e. spreading of tumours to nearby lymph nodes or to other organs via the blood system. Lung cancers are usually divided into 2 groups accounting for about 95% of all cases. The division is based on the type of cells that comprise the cancer. The 2 types of lung cancer are classified based on the cell size of the tumour. They are called small cell lung cancer (SCLC) and non-small cell lung cancer (NSCLC) where the latter includes several types of tumours. SCLC is less common, however they grow more rapid and are more likely to metastasize than NSCLCs. SCLCs have often already spread to other parts of the body when the disease is diagnosed thus it is of high importance to detect lung cancer at an early stage using efficient markers.

About 5% of lung cancers are of rare cell types, such as carcinoid tumour, lymphoma, or metastatic (cancers from other parts of the body that spread to the lungs).

The specific types of primary lung cancers are Adenocarcinoma (an NSCLC) which is the most common type of lung cancer, making up 30-40% of all cases. A subtype of adenocarcinoma is called bronchoalveolar cell carcinoma, which creates a pneumonia-like appearance on chest x-ray films. Squamous cell carcinoma (an NSCLC) is the second most common type of lung cancer, making up about 30% of all lung cancers while large cell cancer makes up 10% and SCLC 20% of all cases and carcinoid lung cancer accounts for 1% of all cases.

Cancer Diagnosis and Identification of Tumour Origin

Cancer classification relies on the subjective interpretation of both clinical and histo-pathological information by eye with the aim of classifying tumours in generally accepted categories based on the tissue of origin of the tumour. However, clinical information can be incomplete or misleading. In addition, there is a wide spectrum in cancer morphology and many tumours are atypical or lack morphologic features that are useful for differential diagnosis. These difficulties may result in diagnostic confusion, with the need for mandatory second opinions in all surgical pathology cases (Tomaszewski and LiVolsi 1999, Cancer 86: 2198-2200).

Another problem for cancer diagnostics is the identification of tumour origin for metastatic carcinomas. For example, in the United States, 51,000 patients (4% of all new cancer cases) present annually with metastases arising from occult primary carcinomas of unknown origin (ACS Cancer Facts & Figures 2001: American Cancer Society). Adenocarcinomas represent the most common metastatic tumours of unknown primary site. Although these patients often present at a late stage, the outcome can be positively affected by accurate diagnoses followed by appropriate therapeutic regimens specific to different types of adenocarcinoma (Hillen 2000, Postgrad. Med. J. 76: 690-693). The lack of unique microscopic appearance of the different types of adenocarcinomas challenges morphological diagnosis of adenocarcinomas of unknown origin. The application of tumour-specific serum markers in identifying cancer type could be feasible, but such markers are not available at present (Milovic et al. 2002, Med. Sci. Monit. 8: MT25-MT30). Microarray expression profiling has been used to successfully classify tumours according to their site of origin (Ramaswamy et al. 2001, Proc. Natl. Acad. Sci.U.S.A. 98: 15149-15154), but the lack of a standard for array data collection and analysis make them difficult to use in a clinical setting. SAGE (serial analysis of gene expression), on the other hand, measures absolute expression levels through a tag counting approach, allowing data to be obtained and compared from different samples. The drawback of this method is, however, its low throughput, making it inappropriate for routine clinical applications. Quantitative real-time PCR is a reliable method for assessing gene expression levels from relatively small amounts of tissue (Bustin 2002, J. Mol. Endocrinol. 29: 23-39). Although this approach has recently been successfully applied to the molecular classification of breast tumours into prognostic subgroups based on the analysis of 2,400 genes (Iwao et al. 2002, Hum. Mol. Genet. 11: 199-206), the measurement of such a large number of randomly selected genes by PCR is still not clinically practical.

Another limitation to further study and identify potential biomarkers is the difficulty of conducting retrospective studies with archived tumour samples (Ludwig and Weinstein, 2005). To be useful for subsequent studies, tumour samples obtained from the operating room must be transported to the pathology laboratory in a timely manner, where the samples are sectioned and stored as frozen or formalin-fixed and paraffin-embedded (FFPE) for archiving in a tumour bank. The quality of the RNA of frozen and FFPE samples is often compromised and is, thus, unsuitable for conducting accurate molecular tests. Hence, the small size of miRNAs offers a unique advantage due to the fact that these short RNA molecules are more stable and less prone to enzymatic degradation by RNAses, and are therefore amenable to an accurate assessment of miRNA levels in archival tumour samples.

SUMMARY OF INVENTION

The present invention solves the above described problems by providing novel miRNA sequences useful as biomarkers for diagnostic purposes of human breast and lung cancers.

The present invention furthermore provides novel miRNA sequences which are useful as forming the basis for molecular targeting for cancer intervention, in which for example LNA-modified, stabilized synthetic miRNA species (miRNA agonist) are used to replace the activity of a missing or a down-regulated miRNA or an LNA-modified antagonistic-miR oligonucleotide used to inhibit the activity of an amplified or over-expressed miRNA, as well as for engineered over-expression of a repressed species in desired pulmonary epithelial cells that basally do not express them.

The invention furthermore provides novel miRNA sequences, which allow identification of the target genes of these miRNAs, thereby enabling us to understand how the altered expression of these miRNAs affects cellular properties important for oncogenesis (including activation or repression in dysplastic tissues) and for the maintenance or progression of early pre-malignant lesions. This, in turn, can be used to identify additional molecular targets for development of novel, targeted breast and lung cancer treatment or chemoprevention.

The invention furthermore provides protocols for clinical application of miRNA detection as diagnostic and/or prognostic tools which would permit detecting these diagnostic miRNAs with less invasive techniques than biopsy, such as in ductal fluid samples (from nipple aspirates or ductal lavage) or in peripheral blood, in order to screen for early stages of breast cancer. This allows predicting outcomes of pre-treatment and to predict which therapeutic agents would be most effective. The invention furthermore provides novel miRNA sequences and methods based on these sequences allowing monitoring of changes in the miRNA expression patterns useful as early indicators of response to treatment.

These provisions are encompassed by the embodiments of the present invention characterised in the claims.

It is thus an object of the present invention to provide a method for detection, classification, diagnosis and prognosis of a disease comprising the steps of obtaining at least one sample from an individual and detecting the presence or absence of expression and/or the expression level of at least one nucleic acid molecule described herein.

It is likewise an object of the present invention to provide a method for detection, classification, diagnosis and prognosis of breast or lung cancer comprising the steps of obtaining at least one sample from an individual and detecting the presence or absence of expression and/or the expression level of at least one nucleic acid molecule described herein.

Thus it is an aspect of the present invention to provide a probe for the detection of said nucleic acid molecule.

It is furthermore an aspect of the present invention to provide a nucleic acid molecule as specified herein for the production of a pharmaceutical composition, and a pharmaceutical composition comprising at least one nucleic acid molecule as described herein.

An aspect of the invention regards a kit comprising at least one probe for detection of at least one nucleic acid molecule as described herein.

It is also an aspect of the present invention to provide a nucleic acid construct encoding at least one nucleic acid molecule described herein.

It is a further aspect of the present invention to provide a delivery vehicle comprising the nucleic acid molecule described herein or the nucleic acid construct of the above.

Yet an aspect of the present invention provides a cell comprising at least one nucleic acid molecule described herein.

It follows that the present invention also provides a pharmaceutical composition comprising any of the nucleic acid constructs, cells or delivery vehicles mentioned herein.

An object of the present invention regards a method of modulating the expression of a pre-miRNA or miRNA in a cell, tissue or animal comprising contacting the cell, tissue or animal with any of the compositions of the present invention.

Yet an object of the present invention regards a method of treating or preventing a disease or disorder associated with aberrant expression of a pre-miRNA, miRNA or the target of a miRNA in a cell, tissue or animal comprising contacting the cell, tissue or animal with any of the compositions of the present invention.

The present invention also provides for the use of a nucleic acid molecule described herein, for the production of a pharmaceutical composition for the diagnosis or treatment of cancer.

DETAILED DESCRIPTION OF THE INVENTION

Definitions

Figure 1:
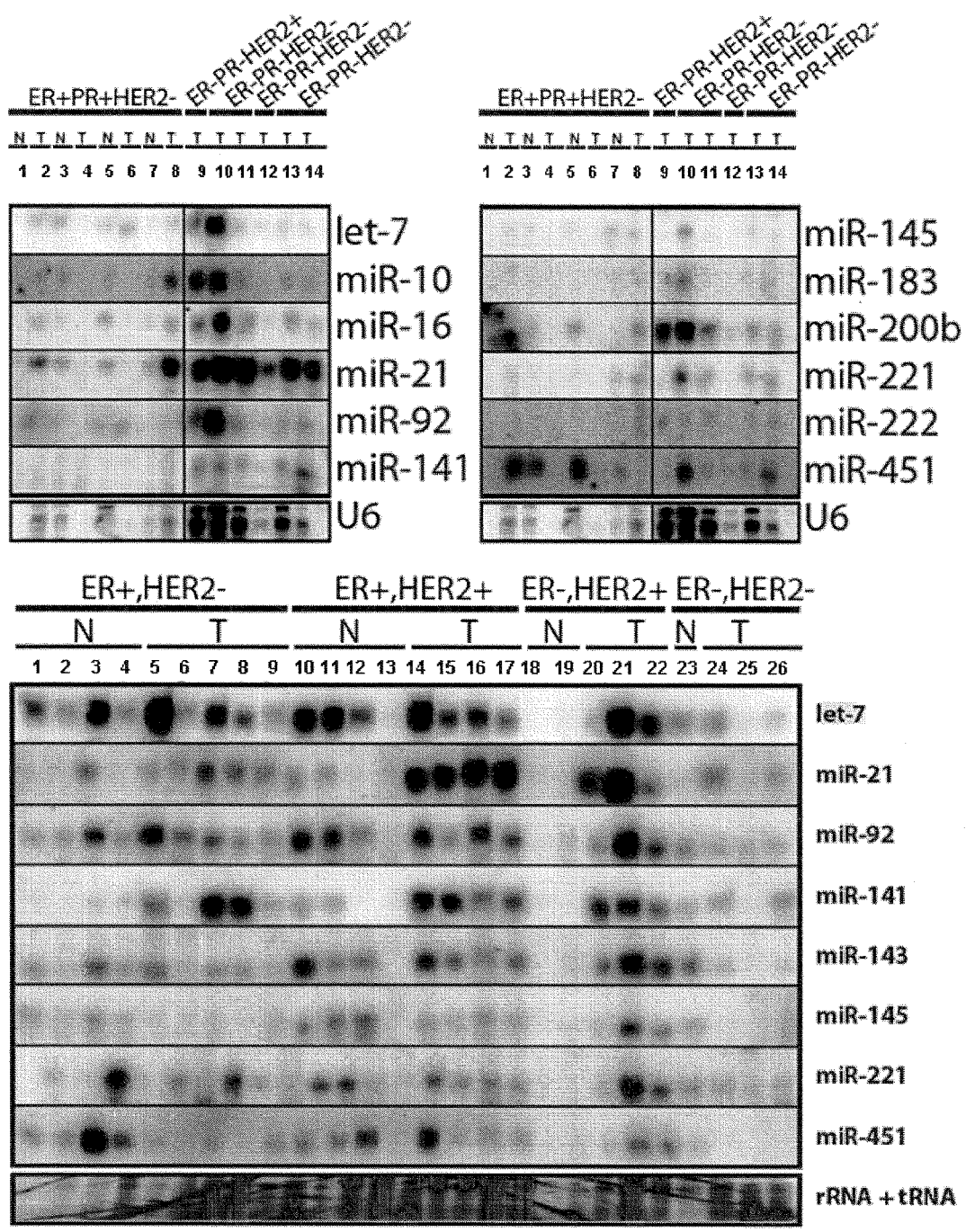
FIG. 1: Northern blots used for quantification of data presented in table IV (upper panel) and table V (lower panel). Numbers directly above panels refer to BC # numbers in tables IV and V.

Chemotherapeutic: A drug used to treat a disease, especially cancer. In relation to cancer the drugs typically target rapidly dividing cells, such as cancer cells.

Complementary or substantially complementary: Refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 80% of the nucleotides of the other strand, usually at least about 90% to 95%, and more preferably from about 98 to 100%.

Complementary DNA (cDNA): Any DNA obtained by means of reverse transcriptase acting on RNA as a substrate. Complementary DNA is also termed copy DNA.

Complementary strand: Double stranded polynucleotide contains two strands that are complementary in sequence and capable of hybridizing to one another.

Cytostatic: A drug that inhibits or suppresses cellular growth and multiplication.

Delivery vehicle: An entity whereby a nucleotide sequence or polypeptide or both can be transported from at least one media to another.

Fragment: is used to indicate a non-full length part of a nucleic acid or polypeptide. Thus, a fragment is itself also a nucleic acid or polypeptide, respectively.

In situ detection: The detection of expression or expression levels in the original site hereby meaning in a tissue sample such as biopsy.

LNA: Locked nucleic acid. LNA is a modified RNA nucleotide in which the sugar ring is conformationally locked in the 3' endo conformation by introduction of a O2', C4'-methylene linkage thereby increasing its thermal stability.

miRNA: miRNA or microRNA refer to 19-25 nt non-coding RNAs derived from endogenous genes that act as post-transcriptional regulators of gene expression. They are processed from longer (ca 70-80 nt) hairpin-like precursors termed pre-miRNAs by the RNAse III enzyme Dicer. MiRNAs assemble in ribonucleoprotein complexes termed miRNPs and recognise their target sites by antisense complementarity thereby mediating down-regulation of their target genes. Near-perfect or perfect complementarity between the miRNA and its target site results in target mRNA cleavage, whereas limited complementarity between the miRNA and the target site results in translational inhibition of the target gene.

miRNA targeting moiety: Is any moiety or entity capable of binding, inhibiting, or interfering with the activity and/or expression of a miRNA, this being either a (such as one or more) mature or precursor miRNA. Preferably, the moiety is capable of binding the target miRNA.

Nucleic acid: The term "nucleic acid" refers to polydeoxyribonucleotides (containing 2-deoxy-D-ribose), to polyribonucleotides (containing D-ribose), and to any other type of polynucleotide which is an N glycoside of a purine or pyrimidine base, or modified purine or pyrimidine bases. The term refers only to the primary structure of the molecule. Thus, the term "nucleic acid" includes double- and single-stranded DNA of different lengths, as well as double- and single stranded RNA of different lengths, or synthetic variants hereof such as for example LNA, of different lengths. Thus, the nucleic acid may for example be DNA, RNA, LNA, HNA, PNA, or any other variant hereof. Chemically modified oligonucleotides are especially relevant aspects of the present invention; these are known to the skilled person. As used herein the term nucleotide includes linear oligomers of natural or modified monomers or linkages, including deoxyribonucleotides, ribonucleotides, anomeric forms thereof, peptide nucleic acid monomers (PNAs), locked nucleotide acid monomers (LNA), and the like, capable of specifically binding to a single stranded polynucleotide tag by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3-4, to several tens of monomeric units, e.g. 40-60. Whenever an oligonucleotide is represented by a sequence of letters, such as "ATGCCTG," it will be understood that the nucleotides are in 5' 3' order from left to right and the "A" denotes deoxyadenosine, "C" denotes deoxycytidine, "G" denotes deoxyguanosine, and "T" denotes thymidine, unless otherwise noted. In addition to the 100% complementary form of double-stranded oligonucleotides, the term "double-stranded" as used herein is also meant to refer to those forms which include such structural features as bulges and loops.

Operative linker: A nucleic acid sequence or a peptide that bind together two sequences in a nucleic acid construct or (chimeric) polypeptide in a manner securing the biological processing of the nucleic acid or polypeptide.

Plurality: At least two.

pri-miRNA: Refers to the primary miRNA transcript. Initially, miRNA genes are transcribed by RNA polymerase II into long primary miRNAs (pri-miRNAs). The processing of these pri-miRNAs into the final mature miRNAs occurs stepwise and compartmentalized. In animals, pri-miRNAs are processed in the nucleus into 70-80-nucleotide precursor miRNAs (pre-miRNAs) by the RNase III enzyme Drosha. Both pri-miRNA and pre-RNA are objects of the present invention and the terms may be used interchangeably herein.

Probe: The term "probe" refers to a defined oligonucleotide sequence or a nucleic acid sequence which said sequence is used to detect target DNA or RNA nucleic acid sequences by hybridization, bearing a complementary sequence to the probe. A probe may be labelled to facilitate detection.

Promoter: Refers to a regulatory region of DNA a short distance upstream from the 5' end of a transcription start site that acts as the binding site for RNA polymerase. A region of DNA to which RNA polymerase binds in order to initiate transcription.

siRNA: (Small interfering RNAs) The term "siRNA" refers to 21-25 nt RNAs derived from processing of linear double-stranded RNA. siRNAs assemble in complexes termed RISC(RNA-induced silencing complex) and target homologous RNA sequences for endonucleolytic cleavage. Synthetic siRNAs also recruit RISCs and are capable of cleaving homologous RNA sequences.

Surfactant: A surface active agent capable of reducing the surface tension of a liquid in which it is dissolved. A surfactant is a compound containing a polar group which is hydrophilic and a non polar group which is hydrophobic and often composed of a fatty acid chain.

Vaccine: A substance or composition capable of inducing a protective immune response in an animal. A protective immune response being an immune response (humoral/antibody and/or cellular) inducing memory in an organism, resulting in the infectious agent, being met by a secondary rather than a primary response, thus reducing its impact on the host organism.

Variant: a 'variant' of a given reference nucleic acid or polypeptide refers to a nucleic acid or polypeptide that displays a certain degree of sequence homology to said reference nucleic acid or polypeptide but is not identical to said reference nucleic acid or polypeptide.

Vector: A genetically engineered nucleic acid also referred to as nucleic acid construct: Typically comprising several elements such as genes or fragments of same, promoters, enhancers, terminators, polyA tails, linkers, selection markers or others. A vector may enable expression of cloned genes or gene fragments in a particular cell type, or be used to transfer genetic information by insertion etc.

Vehicle: An agent with which genetic material can be transferred e.g. a modified virus or a chemical or other transfection agent.

The present invention relates to methods of detecting, classifying, diagnosing and providing a prognosis for hyperproliferative diseases such as cancer and especially breast and lung cancer by the detection of nucleic acid molecules. The invention furthermore relates to pharmaceutical compositions comprising nucleic acid molecules and their use in treatment of said diseases.

miRNA

An aspect of the present invention relates to the use and detection of microRNA (miRNA) sequences especially regarding cancer and specifically human breast and lung cancer respectively.

By miRNA is understood a single-stranded RNA of typically 19-25 nucleotides length, also referred to as a mature miRNA. Such single-stranded RNAs may be isolated from an organism, but may also be synthesized by standard techniques. miRNA is in an organism synthesized as pri-miRNA or primary miRNA transcript which is enzymatically cleaved into pre-miRNA and finally after a second round of enzymatic cleavage results in miRNA.

The present invention relates to the discovery of differential expression levels of various miRNAs in cancerous tissue compared to normal tissue, see examples for specifics. When compared to biopsies from corresponding healthy tissue both by analysing whole samples by Northern and LNA microarray techniques and by analysing spatial distribution of miRNAs within epithelial structures of breast tissue by in situ hybridization techniques, the following miRNAs are down-regulated in breast tumours: hsa-miR-451, hsa-miR-143 and hsa-miR-145. In contrast, the following miRNAs are upregulated in specific subtypes of breast tumours compared to normal breast biopsies: hsa-miR-141, hsa-miR-200b, hsa-miR-200c, hsa-miR-221, hsa-miR-222 and hsa-miR-21. The results of the experiments are summarised in Table A, see Example 3 for more details. The hereby disclosed discovery is obviously of great interest and consequently it is worth noting that all of these miRNAs are aspects of the present invention. The downregulation of hsa-miR-451 and the upregulation of hsa-miR-200b, hsa-miR-200c, hsa-miR-221 and hsa-miR-222 are of significant interest, especially in relation to breast cancer, and especially the discovery of the downregulation of hsa-miR-451 is of great importance.

The present invention furthermore relates to the discovery of differential expression levels of various miRNAs in cancerous lung tissue compared to normal tissue, see examples for specifics. When compared to biopsies from corresponding healthy tissue both by analysing whole samples by Northern and LNA microarray techniques and by analysing spatial distribution of miRNAs within epithelial structures of lung tissue by in situ hybridization techniques, the following miRNAs are down-regulated in lung tumours: hsa-miR-34b, hsa-miR-34c, hsa-miR-142-3p, hsa-miR-142-5p, hsa-miR-486, hsa-miR-451, hsa-miR-145, hsa-miR-144 and hsa-miR-150. In contrast, the following miRNAs are upregulated in lung tumours compared to biopsies from healthy lung tissue: hsa-miR-31, hsa-miR-127, hsa-miR-141, hsa-miR-136 and hsa-miR-376a.

The results of the experiments are summarised in Table A, see examples for more details. The hereby disclosed discovery is obviously of great interest and consequently it is worth noting that all of these miRNAs are aspects of the present invention. The downregulation of hsa-miR-34c and hsa-miR150 are of significant interest, especially in relation to lung cancer.

TABLE A

| SEQ ID NO | Name | Form | Tumour vs normal expr. |
|---|---|---|---|
| 1 | hsa-miR-451 | mature | down |
| 2 | hsa-miR-143 | mature | down |
| 3 | hsa-miR-145 | mature | down |
| 4 | hsa-miR-141 | mature | up |
| 5 | hsa-miR-200b | mature | up |
| 6 | hsa-miR-200c | mature | up |
| 7 | hsa-miR-221 | mature | up |
| 8 | hsa-miR-222 | mature | up |
| 9 | hsa-miR-451 | precursor | No data (ND) |
| 10 | hsa-miR-143 | precursor | (ND) |
| 11 | hsa-miR-145 | precursor | (ND) |
| 12 | hsa-miR-141 | precursor | (ND) |
| 13 | hsa-miR-200b | precursor | (ND) |
| 14 | hsa-miR-200c | precursor | (ND) |
| 15 | hsa-miR-221 | precursor | (ND) |
| 16 | hsa-miR-222 | precursor | (ND) |
| 17 | hsa-miR-21 | mature | up |
| 18 | hsa-miR-21 | precursor | (ND) |
| 19 | hsa-miR-34b | mature | down |
| 20 | hsa-miR-34c | mature | down |
| 21 | hsa-miR-142-3p | mature | down |
| 22 | hsa-miR-142-5p | mature | down |
| 23 | hsa-miR-486 | mature | down |
| 24 | hsa-miR-144 | mature | down |
| 25 | hsa-miR-31 | mature | up |
| 26 | hsa-miR-127 | mature | up |
| 27 | hsa-miR-136 | mature | up |
| 28 | hsa-miR-376a | mature | up |
| 29 | hsa-miR-150 | mature | down |

All of the miRNAs of Table A are thus differentially expressed in hyperproliferative tissue compared to normal tissue and all are of special interest with regard to the present invention. Both miRNAs, the expression of which is upregulated in hyperproliferative tissue are aspects of the present invention as are miRNAs the expression of which is down-regulated in hyperproliferative tissues compared to normal tissue. A preferred embodiment of the present invention regards all the miRNAs or nucleic acid molecules as defined herein below in respect to hyperproliferative tissue such as cancerous tissue. A more preferred embodiment regards the miRNAs/the nucleic acid molecules as defined herein of SEQ ID NOs 1 to 18 of Table A in regards to breast cancer tissue and SEQ ID NOs: 1, 3, 4 and 19 to 29 of Table A in regards to lung cancer tissue. Thus SEQ ID NOs: 1, 3 and 4 are an embodiment of both present invention regarding both lung and breast cancer. An even more preferred embodiment regards the miRNAs/nucleic acid molecules of SEQ ID NO: 1, 5, 6, 7, 8, 9, 13, 14, 15 and 16 in regards to breast cancer and SEQ ID NO: 1, 3, 4 and 19 to 29 in regards to lung cancer. A most preferred embodiment regards the miRNA of SEQ ID NO: 1 and 9 in regards to breast cancer and SEQ ID NO: 19 and 29 in regards to lung cancer.

The present invention thus regards the sequences identified herein as SEQ ID NOs: 1 to 29. These sequences are exact sequences of miRNAs and their precursors as found in the human body. The sequences of the present invention may be isolated here from or may be synthesized by standard techniques known in the art.

Bases not commonly found in natural nucleic acids may be included in the nucleic acids of the present invention and these include, for example, inosine and 7-deazaguanine. Furthermore, synthetic nucleotides that confer an added stability to the nucleotides of the present invention, such as LNA, fall within the scope of the present invention. LNA is a synthetic RNA analog that increases the thermal stability of oligonucleotides. Other modifications of the nucleotides of the present invention that confer added metabolic or thermal stability to these are also included within the scope of the present invention.

The invention also regards sequences which are complementary to any of sequences SEQ ID NO: 1 to 29. The complementary sequence of a nucleic acid sequence as used herein refers to an oligonucleotide or a nucleic acid sequence that can form a double-stranded structure by means of Watson-Crick base pairing, i.e. by formation of hydrogen bonds between the complementary nucleobases. Thus complementary refers to the capacity for precise pairing between two nucleic acid sequences with one another. For example, if a nucleotide at a certain position of an oligonucleotide is capable of hydrogen bonding with a nucleotide at the corresponding position of a DNA, RNA or other nucleic acid molecule as defined herein, then the oligonucleotide and the DNA or RNA are considered to be complementary to each other at that position. The DNA or RNA strand are considered complementary to each other when a sufficient number of nucleotides in the oligonucleotide can form hydrogen bonds with corresponding nucleotides in the target DNA or RNA to enable the formation of a stable complex. Thus, complementarity may not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

The invention also relates to fragments of said sequences. For the mature miRNAs (SEQ ID NOs: 1 to 8, 17 and 19 to 29) said fragments are at least 10 nucleotides in length, such as 11, 12, 13, 14, 15, 16, 17 or 18 nucleotides in length. Preferably, the fragments are 19, 20, 21, 22, or 23 nucleotides in length. For the precursor miRNA sequences, the fragments comprise either the sequence of the mature miRNA or its complementary sequence or both. The precursor miRNA sequences are at least 40 nucleotides in length, such as at least 50, 60, 65, 70, 75, 80, 85, 90, 95, 100 or 105 nucleotides in length.

In one preferred embodiment of the invention there is also provided variants of the sequences SEQ ID NO: 1 to 8 and 17 and variants of fragments thereof. In these variants one or more nucleotides have been substituted for (an)other nucleotide(s) or nucleotides may be added or deleted from the variant compared to the predetermined sequence. The variant sequences may herein be referred to as such or functional equivalents or substituted sequences; these expressions are used interchangeably herein.

Variants are characterized by their degree of identity to the predetermined sequence identified by a given SEQ ID NO from which the variant sequence is derived or to which it can be said to be related. The degree of identity shared between any of the sequences identified as SEQ ID NO 1 to 29 and a variant sequence is preferably at least 55% sequence identity, such as 60% sequence identity, for example 65%, such as at least 70% sequence identity or 75% sequence identity. More preferably the variant sequence shares at least 80% sequence identity to any of sequences SEQ ID NO: 1 to 29, such as 85% sequence identity, for example 90% sequence identity, such as at least 92% sequence identity or 94% sequence identity. Most preferably the variant sequences share at least 95%, for example 96% sequence identity, such as 97% sequence identity, such as at least 98% sequence identity, or most preferably the variant shares 99% sequence identity with the predetermined sequence.

The term "identity" or "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleotide (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The identity of the sequences is calculated by standard sequence identity calculation methods.

The present invention also regards nucleic acid molecules which under stringent conditions can hybridize to any of the nucleic acid molecules described in the above. Stringent conditions as used herein denote stringency as normally applied in connection with Southern blotting and hybridization as described e.g. by Southern E. M., 1975, J. Mol. Biol. 98:503-517. For such purposes it is routine practice to include steps of prehybridization and hybridization. Such steps are normally performed using solutions containing 6×SSPE, 5% Denhardt's, 0.5% SDS, 50% formamide, 100 μg/ml denatured salmon sperm DNA (incubation for 18 hrs at 42° C.), followed by washings with 2×SSC and 0.5% SDS (at room temperature and at 37° C.), and a washing with 0.1×SSC and 0.5% SDS (incubation at 68° C. for 30 min), as described by Sambrook et al., 1989, in "Molecular Cloning/A Laboratory Manual", Cold Spring Harbor), which is incorporated herein by reference.

When referring to a nucleotide sequence or nucleic acid molecule in the remainder of the text, it shall be understood to be a nucleotide sequence or nucleic acid molecule comprising:
 a) a nucleotide sequence selected from the group consisting of SEQ ID NO 1 to 29.
 b) a nucleotide sequence which is complementary to a) and/or,
 c) a nucleotide sequence which is a fragment of a) or b) and/or,
 d) a nucleotide sequence which has an identity of at least 80% to a sequence of a), b) or c) and/or,
 e) a nucleotide sequence which hybridizes under stringent conditions to a sequence of a), b), c) or d).

Cancer

An aspect of the present invention regards the detection, classification, prevention, diagnosis, prognosis and treatment of cancer, especially breast and lung cancers.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as nonpathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumour growth. Examples of nonpathologic hyperproliferative cells include proliferation of cells associated with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renalcell carcinoma, prostate cancer and/or testicular tumours, non-small cell carcinoma of the lung, cancer of the small intestine and cancer of the esophagus.

Preferably, the present invention regards breast and lung cancer respectively. Breast cancer is a cancer of the breast tissue. There are many different types of breast cancer, but the vast majority, over 80%, begins in either the milk ducts or the lobular tissue. Breast cancers can be classified histologically based upon the types and patterns of cells that compose them. Carcinomas can be invasive; extending into the surrounding stroma, or non-invasive; confined just to the ducts or lobules. Invasive carcinomas of the breast include: Infiltrating Ductal Carcinoma, Infiltrating Lobular Carcinoma, Infiltrating Ductal & Lobular Carcinoma, Medullary Carcinoma, Mucinous (colloid) Carcinoma, Comedocarcinoma, Paget's disease, Papillary Carcinoma, Tubular Carcinoma, Adenocarcinoma and Carcinoma. Non-invasive carcinomas of the breast include: Intraductal Carcinoma, Lobular Carcinoma in situ (LCIS), Intraductal & LCIS, Papillary Carcinoma and Comedocarcinoma.

Microarray expression profiling of mRNAs in breast cancers indicate that they can be grouped into five distinct subtypes that differ with respect to their patterns of gene expression, detailed phenotypes, prognosis, and susceptibility to specific treatments (Perou et al., 1999, Sorlie et al., 2001, 2003, 2004, 't Veer et al., 2002). These five subtypes are: luminal A, luminal B, HER2-overexpressing, basal and normal-like. The subtypes exhibit distinct gene signatures that correlate with clinical outcome ('t Veer et al., 2002, Sorlie et al., 2003). For example, luminal A subtype is mainly ER+ and its gene signature includes expression of ER, FBP1, GATA3 and other genes. This subtype has the most favourable prognosis and clinical outcome. Similarly, HER2-overexpressing subtype comprises mainly HER2-amplified tumours that express high levels of e.g. HER2, FLOT1, GRB7. This subtype has a less favourable prognosis and clinical outcome.

It is an object of the present invention to provide a method to detect, classify, diagnose and enable a prognosis of cancer. Preferably it is an object of the present invention to provide a method to detect, classify, diagnose and enable a prognosis of breast cancer. The breast cancer may be any breast cancer, specifically any breast cancer selected from the group of: luminal A, luminal B, HER2-overexpressing, basal and normal-like subtypes of breast cancer.

A preferred embodiment of the present invention provides a method to detect, classify, diagnose and enable a prognosis of a breast cancer comprising at least one nucleic acid molecule such as SEQ ID NO: 1, 5, 6, 7, 8, 9, 13, 14, 15 and 16.

A more preferred embodiment of the present invention provides a method to detect, classify, diagnose and enable a prognosis of a hyperproliferative disease comprising detecting a nucleic acid molecule such as SEQ ID NO: 1 or 9.

A most preferred embodiment of the present invention provides a method to detect, classify, diagnose and enable a prognosis of a cancer comprising any of the above molecules in combination with at least one nucleic acid molecule such as SEQ ID NO: 1 to 29.

Another highly preferred embodiment of the present invention regards lung cancer.

Lung cancer is the malignant transformation and expansion of lung tissue, and is the most lethal of all cancers worldwide, responsible for 1.2 million deaths annually. It is caused predominantly by cigarette smoking, and predominantly affected men, but with increased smoking among women, it is now the leading cause of death due to cancer in women. However, some people who have never smoked still get lung cancer.

It is an object of the present invention to provide a method to detect, classify, diagnose and enable a prognosis of cancer. Preferably it is an object of the present invention to provide a method to detect, classify, diagnose and enable a prognosis of lung cancer. The lung cancer may be any lung cancer, specifically any lung cancer selected from the group of small cell lung cancer (SCLC) and non-small cell lung cancer (NSCLC).

A preferred embodiment of the present invention provides a method to detect, classify, diagnose and enable a prognosis of a lung cancer comprising detecting at least one nucleic acid molecule such as SEQ ID NO: 19 to 29.

A more preferred embodiment of the present invention provides a method to detect, classify, diagnose and enable a prognosis of a hyperproliferative disease comprising detecting a nucleic acid molecule such as SEQ ID NO: 19 or 29.

A most preferred embodiment of the present invention provides a method to detect, classify, diagnose and enable a prognosis of a cancer comprising any of the above molecules in combination with at least one nucleic acid molecule such as SEQ ID NO: 1 to 29.

Sample

The present invention provides a method of detection, classification, diagnosis or prognosis of hyperproliferative diseases on at least one sample obtained from an individual. The individual may be any mammal, but is preferably a human. The individual may be any individual, an individual predisposed of a disease or an individual suffering from a disease, wherein the disease is a hyperproliferative disease.

A sample as defined herein is a small part of an individual, representative of the whole and may be constituted by a biopsy or a body fluid sample. Biopsies are small pieces of tissue and may be fresh, frozen or fixed, such as formalin-fixed and paraffin embedded (FFPE). Body fluid samples may be blood, plasma, serum, urine, sputum, cerebrospinal fluid, milk, or ductal fluid samples and may likewise be fresh, frozen or fixed. Samples may be removed surgically, by extraction i.e. by hypodermic or other types of needles, by microdissection or laser capture.

As the object of the present invention regards hyperproliferative diseases especially cancers and specifically breast and lung cancers, obtaining more than one sample, such as two samples, such as three samples, four samples or more from individuals, and preferably the same individual, is of importance. The at least two samples may be taken from normal tissue and hyperproliferative tissue, respectively. This allows the relative comparison of expression both as in the presence or absence of at least one nucleic acid and/or the level of expression of the at least one nucleic acid between the two samples. Alternatively, a single sample may be compared against a "standardized" sample, such a sample being a sample comprising material or data from several samples, preferably also from several individuals. A standardized sample may comprise either normal or hyperproliferative sample material or data.

In a preferred embodiment of the present invention the method of detection, classification, diagnosis or prognosis is performed on a biopsy. In a more preferred embodiment of the present invention the method of detection, classification, diagnosis or prognosis is performed on a body fluid sample such as a blood sample or a ductal fluid sample. Ductal fluid samples may be from nipple aspirates or ductal lavage.

Sample Preparation

Before analyzing the sample, it will often be desirable to perform one or more sample preparation operations upon the sample. Typically, these sample preparation operations will include such manipulations as concentration, suspension, extraction of intracellular material, e.g., nucleic acids from tissue/whole cell samples and the like, amplification of nucleic acids, fragmentation, transcription, labelling and/or extension reactions.

Nucleic acids, especially RNA and specifically miRNA can be isolated using any techniques known in the art. There are two main methods for isolating RNA: phenol-based extraction and silica matrix or glass fiber filter (GFF)-based binding. Phenol-based reagents contain a combination of denaturants and RNase inhibitors for cell and tissue disruption and subsequent separation of RNA from contaminants. Phenol-based isolation procedures can recover RNA species in the 10-200-nucleotide range e.g., miRNAs, 5S rRNA, 5.8S rRNA, and U1 snRNA. If a sample of "total" RNA was purified by the popular silica matrix column or GFF procedure, it may be depleted in small RNAs. Extraction procedures such as those using Trizol or TriReagent, however will purify all RNAs, large and small, and are the recommended methods for isolating total RNA from biological samples that will contain miRNAs/siRNAs.

Any method required for the processing of a sample prior to detection by any of the herein mentioned methods falls within the scope of the present invention. These methods are typically well known by a person skilled in the art.

Detection

It is within the general scope of the present invention to provide methods for the detection of miRNA. An aspect of the present invention relates to the detection of the miRNA sequences of table A or of any nucleic acid molecule as defined in the above. By detection is meant both 1) detection in the sense of presence versus absence of one or more miRNAs as well as 2) the registration of the level or degree of expression of one or more miRNAs, depending on the method of detection employed.

The detection of one or more nucleic acid molecules allows for the classification, diagnosis and prognosis of a disease such as a hyperproliferative disease, e.g. a cancer and specifically a breast or lung cancer. The classification of a disease is of relevance both medically and scientifically and may provide important information useful for the diagnosis, prognosis and treatment of the disease. The diagnosis of a disease is the affirmation of the presence of the disease based, as is the object of the present invention, on the expression of at least one miRNA or miRNA precursor molecule herein also referred to as a nucleic acid molecule. Prognosis is the estimate or prediction of the probable outcome of a disease and the prognosis of a disease is greatly facilitated by increasing the amount of information on the particular disease. The method of detection is thus a central aspect of the present invention.

Any method of detection falls within the general scope of the present invention. The detection methods may be generic for the detection of nucleic acids especially RNA, or be optimized for the detection of small RNA species, as both mature and precursor miRNAs fall into this category or be specially designed for the detection of miRNA species. The detection methods may be directed towards the scoring of a presence or absence of one or more nucleic acid molecules or may be useful in the detection of expression levels.

The detection methods can be divided into two categories herein referred to as in situ methods or screening methods. The term in situ method refers to the detection of nucleic acid molecules in a sample wherein the structure of the sample has been preserved. This may thus be a biopsy wherein the structure of the tissue is preserved. In situ methods are generally histological i.e. microscopic in nature and include but are not limited to methods such as: in situ hybridization techniques and in situ PCR methods Screening methods generally employ techniques of molecular biology and most often require the preparation of the sample material in order to access the nucleic acid molecules to be detected. Screening methods include, but are not limited to methods such as: Array systems, affinity matrices, Northern blotting and PCR techniques, such as real-time quantitative RT-PCR.

Probe

It is an object of the present invention to provide a probe which can be used for the detection of a nucleic acid molecule as defined herein. A probe as defined herein is a specific sequence of a nucleic acid used to detect nucleic acids by hybridization. A nucleic acid is also here any nucleic acid, natural or synthetic such as DNA, RNA, LNA or PNA. A probe may be labelled, tagged or immobilized or otherwise modified according to the requirements of the detection method chosen. A label or a tag is an entity making it possible to identify a compound to which it is associated. It is within the scope of the present invention to employ probes that are labelled or tagged by any means known in the art such as but not limited to: radioactive labelling, fluorescent labelling and enzymatic labelling. Furthermore the probe, labelled or not, may be immobilized to facilitate detection according to the detection method of choice and this may be accomplished according to the preferred method of the particular detection method.

An aspect of the present invention relates to the use of a nucleic acid molecule as described herein as a probe, wherein the probe is a nucleotide sequence selected from the group consisting of SEQ ID NOs: 1 to 29, and/or a nucleotide sequence which is complementary to any of the nucleotide sequences in the group consisting of SEQ ID NOs: 1 to 29, or a fragment hereof, can hybridize under stringent condition and/or has an identity of at least 80% to any of these sequences. In a preferred embodiment the probe is selected from the group of SEQ ID NOs: 1, 5, 6, 7, 8, 9, 13, 14, 15, 16, 19 and 29 and/or a nucleotide sequence which is complementary to any of the nucleotide sequences in the group consisting of SEQ ID NOs: 1 to 29, or a fragment hereof, can hybridize under stringent conditions and/or has an identity of at least 80% to any of these sequences. Most preferably the probe is either SEQ ID NO: 1, 9, 19 or 29 and/or a nucleotide sequence which is complementary to either SEQ ID NO: 1, 9, 19 or 29 and/or a fragment hereof, and/or can hybridize under stringent condition and/or has an identity of at least 80% to any of these sequences. Any of the herein described probes may be modified by labelling or immobilization as mentioned above.

Detection Methods

An aspect of the present invention regards the detection of nucleic acid molecules by any method known in the art. In the following are given examples of various detection methods that can be employed for this purpose, and the present invention includes all the mentioned methods, but is not limited to any of these.

In Situ Hybridization

In situ hybridization (ISH) applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). DNA ISH can be used to determine the structure of chromosomes and the localization of individual genes and optionally their copy numbers. Fluorescent DNA ISH (FISH) can for example be used in medical diagnostics to assess chromosomal integrity. RNA ISH is used to assay expression and gene expression patterns in a tissue/ across cells, such as the expression of miRNAs/nucleic acid molecules as herein described.

Sample cells are treated to increase their permeability to allow the probe to enter the cells, the probe is added to the treated cells, allowed to hybridize at pertinent temperature, and then excess probe is washed away. A complementary probe is labelled with a radioactive, fluorescent or antigenic tag, so that the probe's location and quantity in the tissue can be determined using autoradiography, fluorescence microscopy or immunoassay, respectively. The sample may be any sample as herein described and will often be a FFPE sample. The probe is likewise a probe according to any probe mentioned herein. An example of the method of detection of selected miRNAs by the method of in situ hybridization is given in Example 2.

An embodiment of the present invention regards the method of detection by in situ hybridization as described herein.

In Situ PCR

In situ PCR is the PCR based amplification of the target nucleic acid sequences prior to ISH. For detection of RNA, an intracellular reverse transcription (RT) step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR the cells are cytocentrifugated onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens. Detection of intracellular PCR-products is achieved by one of two entirely different techniques. In indirect in situ PCR by ISH with PCR-product specific probes, or in direct in situ PCR without ISH through direct detection of labelled nucleotides (e.g. digoxigenin-11-dUTP, fluorescein-dUTP, 3H-CTP or biotin-16-dUTP) which have been incorporated into the PCR products during thermal cycling.

An embodiment of the present invention regards the method of in situ PCR as mentioned herein above for the detection of nucleic acid molecules as detailed herein.

Microarray

A microarray is a microscopic, ordered array of nucleic acids, proteins, small molecules, cells or other substances that enables parallel analysis of complex biochemical samples. A DNA microarray consists of different nucleic acid probes, known as capture probes that are chemically attached to a solid substrate, which can be a microchip, a glass slide or a microsphere-sized bead. Microarrays can be used e.g. to measure the expression levels of large numbers of mRNAs/miRNAs simultaneously.

Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays.

An aspect of the present invention regards the use of microarrays for the expression profiling of miRNAs in hyperproliferative diseases. For this purpose, RNA is extracted from a cell or tissue sample, the small RNAs (18-26-nucleotide RNAs) are size-selected from total RNA using denaturing polyacrylamide gel electrophoresis (PAGE). Then oligonucleotide linkers are attached to the 5' and 3' ends of the small RNAs and the resulting ligation products are used as templates for an RT-PCR reaction with 10 cycles of amplification. The sense strand PCR primer has a Cy3 fluorophore attached to its 5' end, thereby fluorescently labelling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA.

Alternatively, total RNA containing the small RNA fraction (including the miRNA) extracted from a cell or tissue sample is used directly without size-selection of small RNAs, and 3' end labeled using T4 RNA ligase and either a Cy3- or Cy5-labeled short RNA linker (f. ex. 5'-PO4-rUrUrU-Cy3/dT-3' or 5'-PO4-rUrUrU-Cy5/dT-3'). The RNA samples are labelled by incubation at 30° C. for 2 hours followed by heat inactivation of the T4 RNA ligase at 80° C. for 5 minutes. The fluorophore-labelled miRNAs complementary to the corresponding miRNA capture probe sequences on the array will hybridize, via base pairing, to the spot at which the capture probes are affixed. The microarray scanning and data processing is carried out as above.

Several types of microarrays can be employed such as spotted oligonucleotide microarrays, pre-fabricated oligonucleotide microarrays or spotted long oligonucleotide arrays In spotted oligonucleotide microarrays the capture probes are oligonucleotides complementary to miRNA sequences. This type of array is typically hybridized with amplified PCR products of size-selected small RNAs from two samples to be compared (e.g. hyperproliferative and normal samples from an individual) that are labelled with two different fluorophores. Alternatively, total RNA containing the small RNA fraction (including the miRNAs) is extracted from the above-mentioned two samples and used directly without size-selection of small RNAs, and 3' end labeled using T4 RNA ligase and short RNA linkers labelled with two different fluorophores. The samples can be mixed and hybridized to one single microarray that is then scanned, allowing the visualization of up-regulated and down-regulated miRNA genes in one go. The downside of this is that the absolute levels of gene expression cannot be observed, but the cost of the experiment is reduced by half. Alternatively, a universal reference can be used, comprising of a large set of fluorophore-labelled oligonucleotides, complementary to the array capture probes.

In pre-fabricated oligonucleotide microarrays or single-channel microarrays, the probes are designed to match the sequences of known or predicted miRNAs. There are commercially available designs that cover complete genomes from companies such as Affymetrix, or Agilent. These microarrays give estimations of the absolute value of gene expression and therefore the comparison of two conditions requires the use of two separate microarrays.

Spotted long Oligonucleotide Arrays are composed of 50 to 70-mer oligonucleotide capture probes, and are produced by either ink-jet or robotic printing. Short Oligonucleotide Arrays are composed of 20-25-mer oligonucleotide probes, and are produced by photolithographic synthesis (Affymetrix) or by robotic printing. More recently, Maskless Array Synthesis from NimbleGen Systems has combined flexibility with large numbers of probes. Arrays can contain up to 390,000 spots, from a custom array design.

A preferred embodiment of the present invention regards the method of microarray use and analysis as described herein.

A more preferred embodiment of the present invention regards the use of microarrays for the expression profiling of miRNAs in hyperproliferative diseases such as cancer and especially breast cancer.

A most preferred embodiment of the present invention regards the use of microarrays for the expression profiling of miRNAs such as any of SEQ ID NO: 1 to 29 and especially SEQ ID NO 1 and/or 9 and/or 19 and/or 29 in hyperproliferative diseases such as cancer and especially breast and lung cancers.

PCR

The terms "PCR reaction", "PCR amplification", "PCR", "pre-PCR", "Q-PCR", "real-time quantitative PCR" and "real-time quantitative RT-PCR" are interchangeable terms used to signify use of a nucleic acid amplification system, which multiplies the target nucleic acids being detected. Examples of such systems include the polymerase chain reaction (PCR) system and the ligase chain reaction (LCR) system. Other methods recently described and known to the person of skill in the art are the nucleic acid sequence based amplification and Q Beta Replicase systems. The products formed by said amplification reaction may or may not be monitored in real time or only after the reaction as an end-point measurement.

Real-Time Quantitative RT-PCR

Real-time quantitative RT-PCR is a modification of polymerase chain reaction used to rapidly measure the quantity of a product of polymerase chain reaction. It is preferably done in real-time, thus it is an indirect method for quantitatively measuring starting amounts of DNA, complementary DNA or ribonucleic acid (RNA). This is commonly used for the purpose of determining whether a genetic sequence is present or not, and if it is present the number of copies in the sample. There are 3 methods which vary in difficulty and detail. Like other forms of polymerase chain reaction, the process is used to amplify DNA samples, using thermal cycling and a thermostable DNA polymerase.

The three commonly used methods of quantitative polymerase chain reaction are through agarose gel electrophoresis, the use of SYBR Green, a double stranded DNA dye, and the fluorescent reporter probe. The latter two of these three can be analysed in real-time, constituting real-time polymerase chain reaction method.

Agarose gel electrophoresis is the simplest method, but also often slow and less accurate then other methods, depending on the running of an agarose gel via electrophoresis. It cannot give results in real time. The unknown sample and a known sample are prepared with a known concentration of a similarly sized section of target DNA for amplification. Both reactions are run for the same length of time in identical conditions (preferably using the same primers, or at least primers of similar annealing temperatures). Agarose gel electrophoresis is used to separate the products of the reaction from their original DNA and spare primers. The relative quantities of the known and unknown samples are measured to determine the quantity of the unknown. This method is generally used as a simple measure of whether the probe target sequences are present or not, and rarely as 'true' Q-PCR.

Using SYBR Green dye is more accurate than the gel method, and gives results in real time. A DNA binding dye binds all newly synthesized double stranded (ds)DNA and an increase in fluorescence intensity is measured, thus allowing initial concentrations to be determined. However, SYBR Green will label all dsDNA including any unexpected PCR products as well as primer dimers, leading to potential complications and artefacts. The reaction is prepared as usual, with the addition of fluorescent dsDNA dye. The reaction is run, and the levels of fluorescence are monitored; the dye only fluoresces when bound to the dsDNA. With reference to a standard sample or a standard curve, the dsDNA concentration in the PCR can be determined.

The fluorescent reporter probe method is the most accurate and most reliable of the methods. It uses a sequence-specific nucleic acid based probe so as to only quantify the probe sequence and not all double stranded DNA. It is commonly carried out with DNA based probes with a fluorescent reporter and a quencher held in adjacent positions, so-called dual-labelled probes. The close proximity of the reporter to the quencher prevents its fluorescence; it is only on the breakdown of the probe that the fluorescence is detected. This process depends on the 5' to 3' exonuclease activity of the polymerase involved. The real-time quantitative PCR reaction is prepared with the addition of the dual-labelled probe. On denaturation of the double-stranded DNA template, the probe is able to bind to its complementary sequence in the region of interest of the template DNA (as the primers will too). When the PCR reaction mixture is heated to activate the polymerase, the polymerase starts synthesizing the complementary strand to the primed single stranded template DNA. As the polymerisation continues it reaches the probe bound to its complementary sequence, which is then hydrolysed due to the 5'-3' exonuclease activity of the polymerase thereby separating the fluorescent reporter and the quencher molecules. This results in an increase in fluorescence, which is detected. During thermal cycling of the real-time PCR reaction, the increase in fluorescence, as released from the hydrolysed dual-labelled probe in each PCR cycle is monitored, which allows accurate determination of the final, and so initial, quantities of DNA.

Any method of PCR that can determine the expression of a nucleic acid molecule as defined herein falls within the scope of the present invention. A preferred embodiment of the present invention regards the real-time quantitative RT-PCR method, based on the use of either SYBR Green dye or a dual-labelled probe for the detection and quantification of nucleic acids according to the herein described. Examples of methods for detection of nucleic acid molecules are given in Example 4 and 5

A more preferred embodiment of the present invention regards the methods of real-time quantitative RT-PCR for the expression profiling of miRNAs in hyperproliferative diseases such as cancer and especially breast cancer.

A most preferred embodiment of the present invention regards the methods of real-time quantitative RT-PCR for the expression profiling of miRNAs such as any of SEQ ID NO: 1 to 29 and especially SEQ ID NO 1 and/or 9 and/or 19 and/or 29 in hyperproliferative diseases such as cancer and especially breast and lung cancers.

Northern Blot Analysis

An aspect of the present invention regards the detection of the nucleic acid molecules herein disclosed by the classical and to the art well-known technique of Northern blot analysis. Many variations of the protocol exist and optimizations regarding the detection of miRNAs constitute preferred embodiments of the present invention. It has been indicated that a critical factor in detecting miRNAs is the membrane to which the RNA being detected is bound. An example of the method of Northern blot analysis is given in Example 1.

Affinity Matrices

Affinity matrices may be used as a sample preparation method or preferably as a method of detection. The type of affinity matrix used depends on the purpose of the analysis. For example, where it is desired to analyse miRNA expression levels of particular genes in a complex nucleic acid sample it is often desirable to eliminate ribonucleic acids produced by genes that are constitutively overexpressed and thereby tend to mask gene products expressed at characteristically lower levels. Thus, in one embodiment, the affinity matrix can be used to remove a number of preselected gene products (e.g., actin, GAPDH, globin mRNAs in a blood sample etc.). Similarly, the affinity matrix can be used to efficiently capture, i.e. isolate/detect, a number of known nucleic acid sequences. In this embodiment the matrix is also prepared bearing nucleic acids complementary to those nucleic acids it is desired to isolate. The sample is contacted to the matrix under conditions where the complementary nucleic acid sequences hybridize to the affinity ligands in the matrix. The non-hybridized material is washed off the matrix leaving the desired sequences bound. The hybrid duplexes are then denatured providing a pool of the isolated nucleic acids. The different nucleic acids in the pool can be subsequently separated according to standard methods e.g. gel electrophoresis.

In another embodiment, the affinity matrix is a bead, e.g. a carboxylated five micron polystyrene bead. 5' amino-lined oligonucleotide capture probes complementary to the miRNAs of interest are coupled to the beads impregnated with variable mixtures of two fluorescent dyes that can yield up to 100 colours, each representing a single miRNA species. RNA is isolated from the sample, small RNAs are fractionated, and then RNA oligonucleotide linkers are attached to the 5' and 3' ends of the small RNAs. The resulting ligation products are amplified by polymerase chain reaction (PCR) using a common biotinylated primer, hybridized to the capture beads, and stained with streptavidin-phycoerythrin. The beads are then analysed using a flow cytometer capable of measuring bead colour (denoting miRNA identity) and phycoerythrin intensity (denoting miRNA abundance).

Alternatively, 5'.amino-linked LNA-modified capture probes complementary to the 5'-end of the miRNAs of interest are coupled to the colour-coded beads, contacted with the sample of interest, e.g. a total RNA sample, followed by hybridization of another LNA-modified probe, a so-called detection probe containing a biotin or a fluorophore, which said detection probe hybridizes to the 3'-end of the miRNA of interest. The beads are analysed using a flow cytometer measuring bead colour (denoting miRNA identity) and fluorescence intensity from the detection probe (denoting miRNA abundance).

In a preferred embodiment the abovementioned matrix-based detection methods are applied to the Luminex xMap technology platform and the Luminex compact analyser.

A more preferred embodiment of the present invention regards the methods of matrix-based detection for the expression profiling of miRNAs in hyperproliferative diseases such as cancer and especially breast cancer.

A most preferred embodiment of the present invention regards the methods of matrix-based detection for the expression profiling of miRNAs such as any of SEQ ID NO: 1 to 29 and especially SEQ ID NO 1 and/or 9 and/or 19 and/or 29 in hyperproliferative diseases such as cancer and especially breast and lung cancers.

An embodiment of the present invention comprises any of the herein abovementioned methods for the detection of nucleic acid molecules. In a preferred embodiment an in situ detection method is employed. In another preferred embodiment a screening method is employed. In a more preferred embodiment a method of real-time PCR or microarray analysis is employed.

Preferably, an embodiment of the invention comprises a method of detecting any of the miRNAs of SEQ ID NO: 1 to 29. More preferably, an embodiment of the invention comprises a method of detecting any of the miRNAs of SEQ ID NO: 1, 3, 4, 5, 6, 7, 8, 9, 13, 14, 15, 16, 19, 20, 21, 22, 23, 24, 25, 26, 27, 28 and 29. Most preferably, an embodiment of the invention comprises a method of detecting any of the miRNAs of SEQ ID NO: 1, 9, 19, 25 or 29.

In a further preferred embodiment the invention comprises a method for detecting miR-31 (miRNA of SEQ ID NO: 25) expression, in particular a method detecting an increase level of expression of miR-31, wherein the expression level of miR-31 is higher than a standard value or higher than in corresponding healthy tissue. Such a method may involve detection of miR-31 expression by in situ hybridization, array analysis or PCR, preferably real-time PCR analysis.

Pharmaceutical Composition

"Pharmaceutical agent, drug or composition" refers to any chemical or biological material, compound, or composition capable of inducing a desired prophylactic or therapeutic effect when properly administered to a patient. Some drugs are sold in an inactive form that is converted in vivo into a metabolite with pharmaceutical activity. For purposes of the present invention, the terms "pharmaceutical agent, drug or composition" encompass both the inactive drug and the active metabolite or derivate. Specifically the pharmaceutical agent is an agent with a miRNA targeting moiety. The agent may regulate expression/activity or otherwise interfere with the function of a miRNA and/or pre-miRNA.

A pharmaceutical composition of the invention is formulated to be compatible with its intended route of administration and may thus comprise a pharmaceutically acceptable carrier. Examples of routes of administration include parenteral, e.g., intravenous, intradermal, subcutaneous, intraperitoneal, intramuscular, oral (e.g., inhalation), transdermal (topical), pulmonary and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene-diamine-tetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

It is an aspect of the present invention that the administration form is specifically suited for the disease/disorder to be treated. For example, parenteral and pulmonary administration forms of the active ingredient (e.g. an agent with a miRNA targeting moiety) may be used in the treatment of disorders/diseases of the lungs.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

For pulmonary administration, the compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler. Pulmonay lavage is a further administration form that may be employed.

When desired, formulations can be prepared with enteric coatings adapted for sustained or controlled release administration of the active ingredient.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

Pharmaceutical agent or drug" refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical agent" and "drug" encompass both the inactive drug and the active metabolite.

"Transport" and "delivery" refers to the passage of a substance across or through the skin (i.e., transdermal), including the epidermis and dermis, or across a mucosal membrane (i.e., gastrointestinal, sublingual, buccal, nasal, pulmonary, vaginal, corneal, and ocular membranes), where the substance can contact, and be absorbed into, the capillaries. In certain instances, the delivery and/or transport of the substance across other membranes will be effected.

"Penetration enhancer" refers to a substance which is used to increase the transdermal or transmembrane flux of a compound. A penetration enhancer is typically applied to the skin or mucous membrane in combination with the compound. Enhancers are believed to function by disrupting the skin or mucous membrane barrier or changing the partitioning behavior of the drug in the skin or mucous membrane.

The use and administration of the herein disclosed pharmaceutical components in combination with the pharmaceutically active agent as herein described is standard practice by those skilled in the art.

A therapeutically effective amount of a composition containing a composition of the invention is an amount that is capable of modulating the expression of a pre-miRNA, miRNA or the target of a miRNA according to the herein described. Certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments.

In relation to cancer diseases, upregulated miRNAs are particularly interesting, as potential Onco-miRNA's. Such Onco-miRNA's may act by down-regulating expression of tumor suppressors providing a strong proliferative stimulation. MicroRNAs may target expression of more than one gene, such as two genes or 3 or 4 genes or even such as 10 or 20 genes. In a preferred embodiment of the invention the pharmaceutical composition modulates expression of a pre-miRNA or miRNA that regulates expression of more than one gene, such as at least two genes. It is further preferred that the genes regulated by the miRNA are involved in growth regulation, most preferred are tumor suppressors.

In a preferred embodiment of the invention the pharmaceutical composition comprises an agent that has a miRNA targeting moiety which down-regulates expression of one or more of the miRNAs or pre-miRNAs of SEQ ID NO 4-8, 12-18 and 25-28. In a particularly preferred embodiment the pharmaceutical composition comprises an agent which downregulates expression of miRNA of SEQ ID NO 25.

In a further preferred embodiment of the invention, the pharmaceutical composition comprises an agent that has a miRNA targeting moiety which upregulates expression of the miRNAs or pre-miRNAs of SEQ ID NO 1-3, 9-11, 19-24 and 29.

In an embodiment, the agent that has a miRNA targeting moiety, is a nucleic acid comprising:
a) the nucleotide sequence of SEQ ID NO: 4-8, 12-18 and 25-28 and/or,
b) a nucleotide sequence which is complementary to a) and/or,
c) a nucleotide sequence which is a fragment of a) or b) and/or,
d) a nucleotide sequence which has an identity of at least 80% to a sequence of a), b) or c) and/or,
e) a nucleotide sequence which hybridizes under stringent conditions to a sequence of a), b), c) or d)

In a preferred embodiment the agent is:
b) a nucleotide sequence which is complementary to the nucleotide sequence of SEQ ID NO: 4-8, 12-18 and 25-28 and/or,
c) a nucleotide sequence which is a fragment of b) and/or,
d) a nucleotide sequence which has an identity of at least 80% to a sequence of b) and/or
e) a nucleotide sequence which hybridizes under stringent conditions to a sequence of b).

In a more preferred embodiment the agent is
b) a nucleotide sequence which is complementary to the nucleotide sequence of SEQ ID NO: 25 and/or
c) a nucleotide sequence which is a fragment of b) and/or,
d) a nucleotide sequence which has an identity of at least 80% to a sequence of b) and/or
e) a nucleotide sequence which hybridizes under stringent conditions to a sequence of b).

It is clear from the above that an agent according to the invention may be comprised by a composition, a nucleic acid construct, a delivery vehicle, a cell, a kit or a pharmaceutical composition.

Second Active Ingredient

An aspect of the present invention regards the pharmaceutical composition according to any of the herein disclosed comprising a second active ingredient. The term second active ingredient includes any therapeutic molecule or cocktail of molecules other than the at least one nucleic acid molecule of the herein described.

An embodiment of the present invention regards the prophylaxis and therapy of diseases such as hyperproliferative diseases e.g. cancer and especially breast cancer. It is thus an object of the present invention to provide a pharmaceutical composition comprising a second active ingredient that may be beneficial, i.e. function synergistically, in this regards.

A second active ingredient may therefore be any therapeutic molecule that may be used prophylactically or therapeutically in the treatment of hyperproliferative diseases such as cancer and especially breast cancer. Such therapeutic molecules include, but are not limited to, chemotherapeutic agents, anti-emetic drugs, anti-inflammatory agents, anti-allergenics, cytokines and antibiotics.

Chemotherapy is the use of chemical substances to treat disease. In its modern-day use, it refers primarily to cytotoxic drugs used to treat cancer. The majority of chemotherapeutic drugs can be divided in to: alkylating agents, antimetabolites, anthracyclines, plant alkaloids, topoisomerase inhibitors, and antitumour agents. All of these drugs affect cell division or DNA synthesis and function in some way. Some newer agents don't directly interfere with DNA. These include the new tyrosine kinase inhibitor imatinib mesylate, which directly targets a molecular abnormality in certain types of cancer (chronic myelogenous leukaemia, gastrointestinal stromal tumours). In addition, some drugs may be used which modulate tumour cell behaviour without directly attacking those cells. Hormonal therapy falls into this category.

Several malignancies respond to hormonal therapy. Cancer arising from certain tissues including the mammary glands may be inhibited or stimulated by appropriate changes in hormone balance. Steroids (often dexamethasone) can inhibit tumour growth or the associated edema (tissue swelling), and may cause regression of lymph node malignancies. Breast cancer cells often highly express the estrogen and/or progesterone receptor. Inhibiting the production (with aromatase inhibitors) or action (with tamoxifen) of these hormones can often be used as an adjunct to therapy. Gonadotropin-releasing hormone agonists (GnRH), such as goserelin possess a paradoxic negative feedback effect followed by inhibition of the release of FSH (follicle-stimulating hormone) and LH (luteinizing hormone), when given continuously.

A preferred embodiment of the present invention comprises chemotherapeutic agents such as antineoplastic agents, radioiodinated compounds, toxins, cytostatic and cytolytic drugs, alkylating agents, anti-metabolites, anthracyclines, plant alkaloids, topoisomerase inhibitors, anti-tumour agents, tyrosine kinase inhibitors and hormone agents.

A more preferred embodiment of the present invention comprises chemotherapeutic agents such as any of the above specifically for use with breast cancer. Examples of these include, but are not limited to: Cyclophosphamide, Epirubicin, 5-Fluorouracil or 5 FU, Methotrexate, Mitomycin, Mitozantrone (mitoxantrone), Doxorubicin (Adriamycin), Herceptin, Tamoxifen and other aromatase inhibitors.

These drugs are given in different combinations, also called cocktails. Some of the commonest combinations used for breast cancer are CMF—cyclophosphamide, methotrexate and 5-FU; FEC—epirubicin, cyclophosphamide and 5-FU; E-CMF—epirubicin, followed by CMF; AC—doxorubicin (adriamycin) and cyclophosphamide; MMM—methotrexate, mitozantrone and mitomycin; MM—methotrexate and mitozantrone. All of these fall within the scope of the present invention.

Kit of Parts

An aspect of the present invention regards the inclusion of nucleic acid molecules of the invention in a container, pack, kit or dispenser together with instructions for administration or use. The kit may be for the detection of a nucleic acid molecule, or for the classification, diagnosis and/or prognosis of a disease related to the nucleic acid molecule such as a hyperproliferative disease, e.g. a cancer especially breast cancer. The kit may furthermore provide compositions comprising at least one nucleic acid molecule of the invention for the treatment of diseases such those mentioned herein.

The kit can comprise the nucleic acid molecules or probes of the invention in a form suitable for the detection of said nucleic acid molecules. Thus the kit may comprise the nucleic acid molecules in any composition suitable for the use of the nucleic acid molecules according to the instructions. Furthermore, the kit may comprise any detection device required here for, such as a microarray, a labelling system, a cocktail of components e.g. suspensions required for any type of PCR, especially real-time quantitative RT-PCR, membranes, colour-coded beads, columns or other.

The kit may furthermore contain a pharmaceutical composition comprising the nucleic acid of the invention and an instructional material for the prophylaxis or treatment of a hyperproliferative disease. Such a kit may include a container having the pharmaceutical composition of the invention. Further, a kit comprising a pharmaceutical composition and a delivery device for delivering the composition to an individual can also be provided. By way of example, the delivery device may be an aerosol spray device, an atomizer, a dry powder delivery device, a self-propelling solvent/powder-dispensing device, a syringe, a needle, or a dosage measuring container.

An embodiment of the present invention thus regards pharmaceutical compositions comprising nucleic acid molecules as herein described. Especially pharmaceutical compositions comprising nucleic acid molecules according to SEQ ID NO 1 or 9 or derivates as defined herein are preferred.

Vehicles

Aspects of the present invention relate to various vehicles comprising the nucleic acid molecules of the present invention. By vehicle is understood an agent with which genetic material can be transferred. Herein such vehicles are exemplified as nucleic acid constructs, vectors, and delivery vehicles such as viruses and cells.

Nucleic Acid Construct

By nucleic acid construct is understood a genetically engineered nucleic acid. The nucleic acid construct may be a non-replicating and linear nucleic acid, a circular expression vector, an autonomously replicating plasmid or viral expression vector. A nucleic acid construct may comprise several elements such as, but not limited to genes or fragments of same, promoters, enhancers, terminators, poly-A tails, linkers, markers and host homologous sequences for integration. Methods for engineering nucleic acid constructs are well known in the art (see, e.g., Molecular Cloning: A Laboratory Manual, Sambrook et al., eds., Cold Spring Harbor Laboratory, 2nd Edition, Cold Spring Harbor, N.Y., 1989).

An embodiment of the invention comprises the at least one nucleic acid molecule as herein described comprised within a nucleic acid construct according to the above. Preferred embodiments are nucleic acid constructs comprising at least one of SEQ ID NOs 1 to 29 or their complement, and more preferred embodiments are nucleic acid constructs comprising at least one of SEQ ID NOs 1, 9, 19, 25 or 29 or their complement.

Several nucleic acid molecules may be encoded within the same construct and may be linked by an operative linker. By the term operative linker is understood a sequence of nucleotides two parts of a nucleic acid construct in a manner securing the biological processing of the encoded nucleic acid molecules.

Promoter

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator proteins. At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV 40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. Depending on the promoter, it appears that individual elements can function either cooperatively or independently to activate transcription. Any promoter that can direct transcription initiation of the sequences encoded by the nucleic acid construct may be used in the invention.

An aspect of the present invention comprises the nucleic acid construct wherein the sequence of at least one nucleic acid molecule is preceded by a promoter enabling expression of the at least one nucleic acid molecule. This nucleic acid molecule preferably being at least one of SEQ ID NO: 1 to 29, and more preferably being at least one of SEQ ID NO 1, 9, 19 or 29.

It is a further aspect that the promoter is selected from the group of constitutive promoters, inducible promoters, organism specific promoters, tissue specific promoters and cell type specific promoters. Examples of promoters include, but are not limited to: constitutive promoters such as: simian virus 40 (SV40) early promoter, a mouse mammary tumour virus promoter, a human immunodeficiency virus long terminal repeat promoter, a Moloney virus promoter, an avian leukaemia virus promoter, an Epstein-Barr virus immediate early promoter, a Rous sarcoma virus (RSV) promoter, a human actin promoter, a human myosin promoter, a human haemoglobin promoter, cytomegalovirus (CMV) promoter and a human muscle creatine promoter, inducible promoters such as: a metallothionine promoter, a glucocorticoid promoter, a progesterone promoter, and a tetracycline promoter (tet-on or tet-off), tissue specific promoters such as: HER-2 promoter and PSA associated promoter.

Delivery Vehicle

An aspect of the present invention comprises the nucleic acid construct as described in any of the above, comprised within a delivery vehicle. A delivery vehicle is an entity whereby a nucleotide sequence can be transported from at least one media to another. Delivery vehicles are generally used for expression of the sequences encoded within the nucleic acid construct and/or for the intracellular delivery of the construct. It is within the scope of the present invention that the delivery vehicle is a vehicle selected from the group of: RNA based vehicles, DNA based vehicles/vectors, lipid based vehicles, virally based vehicles and cell based vehicles. Examples of such delivery vehicles include, but are not limited to: biodegradable polymer microspheres, lipid based formulations such as liposome carriers, coating the construct onto colloidal gold particles, lipopolysaccharides, polypeptides, polysaccharides, pegylation of viral vehicles.

A preferred embodiment of the present invention comprises a virus as a delivery vehicle, where the virus is selected from the non-exhaustive group of: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

Recombinant Cell

An aspect of the present invention relates to a cell comprising the nucleic acid construct as defined in any of the above. Such a recombinant cell can be used a tool for in vitro research, as a delivery vehicle for the nucleic acid construct or as part of a gene therapy regime. The nucleic acid construct and nucleic acid based vectors according to the invention can be introduced into cells by techniques well known in the art and which include microinjection of DNA into the nucleus of a cell, transfection, electroporation, lipofection/liposome fusion and particle bombardment. Suitable cells include autologous and non-autologous cells, and may include xenogenic cells.

An embodiment of the present invention is a pharmaceutical composition comprising any of the vehicles described herein, these vehicles being nucleic acid constructs, vectors, delivery vehicles and or cells. Of these embodiments comprising any of SEQ ID NO 1 to 29 are preferred and more preferred are embodiments comprising any of SEQ ID NO 1 and/or 9 and/or 19 and/or 29.

Treatment

The present invention further provides for compositions and methods for treating an individual having or at risk of acquiring a disease or disorder. Treatment includes prophylaxis and/or therapy. The disease may be characterized or caused by the overexpression or overactivity of a gene product, or alternatively, may be caused by the expression or activity of a mutant gene or gene product. The disease may thus be any of the herein mentioned diseases such as hyperproliferative diseases such as cancer and especially breast cancer.

Accordingly, administration of an agent that has a miRNA targeting moiety capable of binding said miRNA, being this either mature or precursor miRNA, or an agent that has an miRNA target binding capability falls within the scope of the present invention. The agent is preferably any of the herein disclosed nucleic acid molecules.

By miRNA target is meant the target mRNA of the miRNA. The target mRNAs of some miRNAs are well characterized and described, for others, the targets are predicted. It is predicted that each miRNA has multiple targets. For a list of predicted targets of miRNA-451 see Example 6.

The present invention provides for both prophylactic and therapeutic methods of treating a subject at risk of or susceptible to, a disease or having a disease associated with aberrant or unwanted target gene expression or activity. Another aspect of the invention pertains to methods of modulating target gene expression, gene product expression or activity for therapeutic purposes. Accordingly, in an exemplary embodiment, the modulatory method of the invention involves contacting a cell capable of expressing a target miRNA or the target mRNA of an miRNA with a therapeutic agent (e.g. a nucleic acid molecule as described herein) that is specific for the target gene or gene product (e.g. a nucleic acid molecule as described herein) such that expression or one or more of the activities of the target is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a target gene product or nucleic acid molecule. Inhibition of target gene activity is desirable in situations in which the target gene is abnormally unregulated and/or in which decreased target gene activity is likely to have a beneficial effect.

An embodiment of the present invention regards the use of any of the herein described pharmaceutical compositions for the treatment or prophylaxis of a disease such as a hyperproliferative disease, e.g. cancer especially breast cancer. A preferred embodiment of the present invention regards the treatment of breast cancers such as any of the breast cancers known as: luminal A, luminal B, HER-2-overexpressing, basal and normal-like breast cancers.

A similarly preferred embodiment of the present invention regards the treatment of lung cancers such as any of the lung cancers known as: small cell lung cancer (SCLC) and non-small cell lung cancer (NSCLC)

Yet an embodiment of the present invention regards the use of a pharmaceutical composition for the modulation of expression or treatment of a disease associated with any aberrant miRNA or any miRNA target mRNA expression. Sequences of human miRNAs are collected in the miRbase.

Targets of miRNAs are likewise found in miRbase, and it is an object of the present invention to treat or modulate the expression of targets of any human miRNAs, preferably the herein mentioned miRNAs such as SEQ ID NOs 1 to 29 and most preferably SEQ ID NO 1, 9, 19 and 29.

An aspect of the present invention relates to the treatment of diseases characterized by the upregulation of miRNAs. Such treatments may comprise administering nucleic acid molecules of the present invention in order to downregulate the miRNAs and/or upregulate the targets of said miRNAs. A preferred embodiment of the present invention relates to treatments counteracting the upregulation of hsa-miR-141, hsa-miR-200b, hsa-miR-200c, hsa-miR-221, has-miR-21, hsa-miR-222, hsa-miR-31, hsa-miR-127, hsa-miR-141, hsa-miR-136 and hsa-miR-376a when these are associated with hyperproliferative diseases. Such treatment may comprise the administration of inhibitory agents e.g. anti-sense molecules, to directly interact with the overexpressed miRNAs.

Another preferred embodiment of the present invention relates to the treatment of diseases characterized by the downregulation of miRNAs. Such treatments may comprise administering nucleic acid molecules of the present invention in order to upregulate the miRNAs and/or downregulate the targets of said miRNAs. A preferred embodiment of the present invention relates to treatments counteracting the downregulation of hsa-miR-451, hsa-miR-143, hsa-miR-145, hsa-miR-34b, hsa-miR-34c, hsa-miR-142-3p, hsa-miR-142-5p, hsa-miR-486, hsa-miR-451, hsa-miR-144 and hsa-miR-150. Such treatment may comprise the administration nucleic acid molecules to supplement the lack of said miRNAs or inducer of the expression of said miRNAs.

It is preferred that agents for regulation of expression of the miRNAs or pre-miRNAs in a cell, tissue or animal normalize the expression level of the targent miRNA or pre-miRNAs. It is further preferred that in case of upregulated miRNAs the expression level is decreased by at least 10%, such as by 20%, such as by 30 or 50%, more preferably such as at least 60% or 70%, most preferably at least 80 or 85%. In case of downregulated miRNAs it is preferred that the expression level is increased to at least 10%, such as by 20%, such as by 30 or 50%, more preferably such as at least 60% or 70% most preferably such as at least 80, 90 or about 100% of the normal expression level in corresponding healthy tissue.

As seen in FIGS. 8-16 upregulation of miR-31 was confirmed in both murine and human lung cancer cells. Directed downregulation of miR-31 secondly conferred growth inhibition involving upregulation of LATS2 and PPP2R2A known as tumour suppressors.

Embodiments of the invention are further exemplified by the following items.

Items

1. A method for detection, classification, diagnosis or prognosis of breast and/or lung cancer comprising the steps of:
    a) obtaining at least one sample from an individual.
    b) detecting the presence or absence of expression and/or the expression level of at least one nucleic acid molecule,
    said nucleic acid molecule comprising:
    c) a nucleotide sequence selected from the group consisting of SEQ ID NOs: 1, 5, 6, 7, 8, 9, 13, 14, 15, 16, 17, 18, in relation to breast cancer and SEQ ID NOs: 1, 3, 4, 19, 20, 21, 22, 23, 24, 25, 26, 27, 28 and 29 in relation to lung cancer.
    d) a nucleotide sequence which is complementary to c) and/or,
    e) a nucleotide sequence which is a fragment of c) or d) and/or,
    f) a nucleotide sequence which has an identity of at least 80% to a sequence of c), d) or e) and/or,
    g) a nucleotide sequence which hybridizes under stringent conditions to a sequence of c), d), e) or f).

2. A method for detection, classification, diagnosis or prognosis of a disease comprising the steps of:
    a) obtaining at least one sample from an individual.
    b) detecting the presence or absence of expression and/or the expression level of at least one nucleic acid molecule,
    said nucleic acid molecule comprising:
    c) a nucleotide sequence selected from the group consisting of SEQ ID NOs: 1, 3, 4, 9, 19, 20, 21, 22, 23, 24, 25, 26, 27, 28 and 29.
    d) a nucleotide sequence which is complementary to c) and/or,
    e) a nucleotide sequence which is a fragment of c) or d) and/or,
    f) a nucleotide sequence which has an identity of at least 80% to a sequence of c), d) or e) and/or,
    g) a nucleotide sequence which hybridizes under stringent conditions to a sequence of c), d), e) or f).

3. The method of item 2, wherein the disease is a hyperproliferative disease such as cancer.

4. The method according to item 3, wherein the cancer is breast cancer.

5. The method according to item 3, wherein the cancer is lung cancer.

6. The method according to any of items 1 to 5, comprising the detection of the expression levels of at least two or more nucleic acid molecules.

7. The method according to any of items 1 to 6, wherein the nucleic acid molecule(s) are selected from the group of SEQ ID NO: 1 to 29.

8. The method according to any of items 1 to 7, wherein at least one nucleic acid molecule is SEQ ID NO: 1 or SEQ ID NO: 9 in relation to breast cancer and/or SEQ ID NO: 19 or SEQ ID NO: 29 in relation to lung cancer.

9. The method according to any of items 1 to 8, wherein a probe comprising:
    a) a nucleotide sequence selected from the group consisting of SEQ ID NOs: 1 to 29.
    b) a nucleotide sequence which is complementary to a) and/or,
    c) a nucleotide sequence which is a fragment of a) or b) and/or,
    d) a nucleotide sequence which has an identity of at least 80% to a sequence of a), b) or c) and/or,
    e) a nucleotide sequence which hybridizes under stringent conditions to a sequence of a), b), c) or d),
    is used for the detection of said nucleic acid molecule(s)

10. The method according to any of items 1 to 9, wherein the at least one sample
    is a biopsy obtained from an individual.

11. The method according to any of items 1 to 10, wherein the at least one sample is a ductal fluid sample.

12. The method according to any of items 1 to 10, wherein the at least one sample is a blood sample.

13. The method according to any of items 1 to 12, wherein the individual is predisposed to or suffering from cancer.

14. The method according to any of items 1 to 13, wherein the expression level of the at least one nucleic acid molecule is detected by in situ detection methods.

15. The method of any of items 1 to 14, wherein the expression level of the at least one nucleic acid molecule is detected by a screening method.

16. The method according to item 15, wherein the screening method comprises comparing at least two samples from the same or different individuals.
17. The method according to items 15 and 16, wherein the screening method comprises an array detection method.
18. The method according to any of items 15 to 17, wherein the screening method comprises a PCR detection method such as real time RT-PCR and/or Q-PCR.
19. The method according to any of items 1 to 18, for detection of the expression level of the nucleic acid molecule for diagnostic purposes.
20. The method according to any of items 1 to 19, for the detection of the expression and or level of same of the nucleic acid molecule prior to treatment of a clinical condition in an individual.
21. The method according to any of items 1 to 20, for the detection of the expression level of the nucleic acid molecule during or after treatment of a clinical condition in an individual.
22. A nucleic acid molecule comprising:
   a) the nucleotide sequence of SEQ ID NO: 1 or 9 or 19 or 29 and/or,
   b) a nucleotide sequence which is complementary to a) and/or,
   c) a nucleotide sequence which is a fragment of a) or b) and/or,
   d) a nucleotide sequence which has an identity of at least 80% to a sequence of a), b) or c) and/or,
   e) a nucleotide sequence which hybridizes under stringent conditions to a sequence of a), b), c) or d)
   for the production of a pharmaceutical composition.
23. A pharmaceutical composition, comprising at least one nucleic acid molecule as defined in item 22.
24. The pharmaceutical composition of item 23, comprising at least two nucleic acid molecules, wherein the second or subsequent nucleic acid molecules comprise:
   a) the nucleotide sequence of SEQ ID NO: 2 to 8 or 1, 3, 4, 10 to 18 and 20 to 28 and/or,
   b) a nucleotide sequence which is complementary to a) and/or,
   c) a nucleotide sequence which is a fragment of a) or b) and/or,
   d) a nucleotide sequence which has an identity of at least 80% to a sequence of a), b) or c) and/or,
   e) a nucleotide sequence which hybridizes under stringent conditions to a sequence of a), b), c) or d).
25. The pharmaceutical composition according to item 23 or 24, for prophylactic or therapeutic applications.
26. The pharmaceutical composition according to any of items 23 to 25, wherein the pharmaceutical composition comprises a pharmaceutically acceptable carrier.
27. The pharmaceutical composition according to any of items 23 to 26, comprising a second active ingredient.
28. The pharmaceutical composition according to item 27, wherein the second active ingredient is selected from the group of chemotherapeutics (cytostatics, anti-virals etc).
29. A kit comprising at least one nucleic acid molecule wherein the nucleic acid molecule comprises:
   a) the nucleotide sequence of SEQ ID NO: 1 or 9 or 19 or 29 and/or,
   b) a nucleotide sequence which is complementary to a) and/or,
   c) a nucleotide sequence which is a fragment of a) or b) and/or,
   d) a nucleotide sequence which has an identity of at least 80% to a sequence of a), b) or c) and/or,
   e) a nucleotide sequence which hybridizes under stringent conditions to a sequence of a), b), c) or d)
30. The kit according to item 29 comprising at least one additional nucleic acid molecule wherein the at least one additional nucleic acid molecule comprises:
   a) the nucleotide sequence of SEQ ID NO: 2 to 8 or 1, 3, 4, 10 to 18 and 20 to 28 and/or,
   b) a nucleotide sequence which is complementary to a) and/or,
   c) a nucleotide sequence which is a fragment of a) or b) and/or,
   d) a nucleotide sequence which has an identity of at least 80% to a sequence of a), b) or c) and/or,
   e) a nucleotide sequence which hybridizes under stringent conditions to a sequence of a), b), c) or d).
31. The kit according to item 29 or 30, wherein the kit comprises a detection device such as a microarray.
32. A nucleic acid construct encoding at least one nucleic acid molecule according to any of items 1, 22 or 24.
33. The nucleic acid construct of item 31 encoding a promoter enabling expression of the at least one nucleic acid molecule.
34. The nucleic acid construct of item 33, wherein the promoter is selected from the group of tissue-specific promoters, cell-type specific promoters, constitutive promoters or inducible promoters.
35. A delivery vehicle comprising the nucleic acid molecule according to any of items 1, 22 or 24 or the nucleic acid construct of any of items 32 to 34.
36. A cell comprising at least one nucleic acid molecule of item 1, 22 or 24.
37. The cell defined in item 36, comprising the nucleic acid construct or vehicle of any of items 32 to 36.
38. A pharmaceutical composition comprising any of the nucleic acid constructs, cells or delivery vehicles of items 32 to 37.
39. A method of modulating the expression of a pre-microRNA or microRNA in a cell, tissue or animal comprising contacting the cell, tissue or animal with a composition according to any of items 22 to 28 or 38.
40. A method of treating or preventing a disease or disorder associated with aberrant expression of a pre-microRNA, microRNA or the target of a miRNA in a cell, tissue or animal comprising contacting the cell, tissue or animal with a composition according to items any of the items 22 to 28 or 38.
41. The method according to item 40, wherein the disease or disorder is a cancer.
42. The method according to item 41, wherein the cancer is a breast cancer.
43. The method according to item 42, wherein the breast cancer is selected from the group of: Luminal A, luminal B, HER-2-overexpressing, basal and normal-like breast cancers.
44. The method according to any of items 39 to 43, wherein the pre-microRNA or microRNA is selected from among any human miRNA.
45. The method according to any of items 39 to 43, wherein the pre-microRNA or microRNA is selected from the group of: SEQ ID NO:1 to 29.
46. The method according to any of items 39 to 45, wherein the modulation, prophylaxis or treatment comprises administering the pharmaceutical composition of any of items 22 to 28 or 38.
47. Use of a nucleic acid molecule according to any of items 1, 2, 22 or 24, for the production of a pharmaceutical composition for the diagnosis or treatment of cancer.

48. The use according to item 47, wherein the cancer is a breast cancer.
49. The use according to item 48, wherein the breast cancer is from the group of: Luminal A, luminal B, HER-2-overexpressing, basal and normal-like breast cancers.
50. The use according to item 47, wherein the cancer is a lung cancer.
51. The use according to item 50, wherein the lung cancer is from the group of: small cell lung cancer (SCLC) or non-small cell lung cancer (NSCLC).

DETAILED DESCRIPTION OF THE DRAWINGS

FIG. 1: Northern blots used for quantification of data presented in Table IV (upper panel) and Table V (lower panel). 5 µg of total RNA were electrophoretically resolved through a 12% urea-polyacrylamide gel, transferred to a nylon membrane and hybridized with radioactively-labelled StarFire probes (IDT) following vendor's recommendations. Northern blots of selected miRNAs in the same set of patient cases used for microarray experiments (upper panel) and in an additional set of 15 patients (lower panel). Molecular pathology for each patient case is indicated in the figure.

Figure 2:
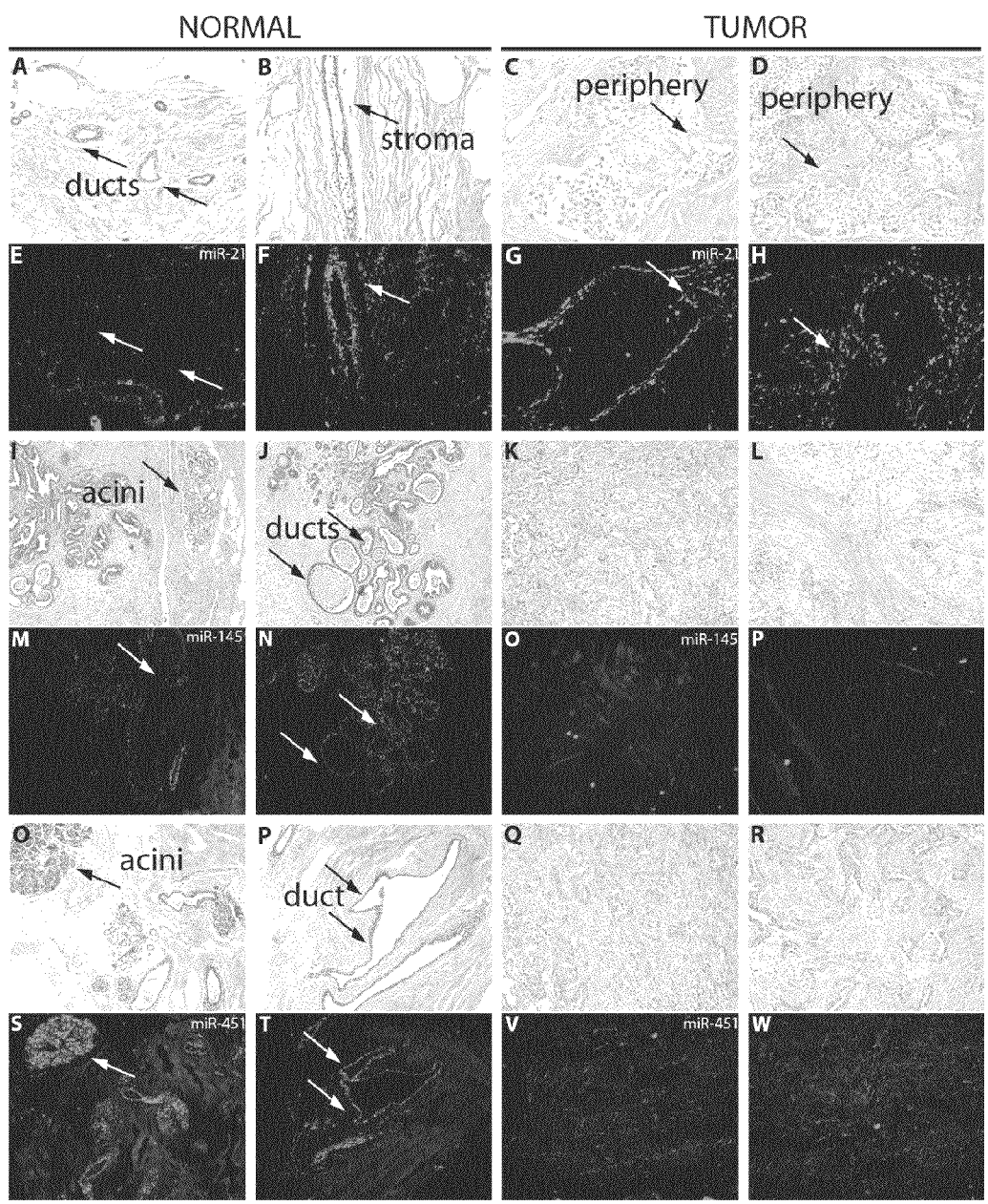
FIG. 2: Detection of miRNA expression by in situ hybridization using FITC-labeled LNA probes in FFPE sections from breast cancer patients.

FIG. 2: Detection of miRNA expression by in situ hybridization using FITC-labelled LNA probes in FFPE sections from breast cancer patients. Archival paraffin-embedded samples were retrieved and examined by surgical pathologist Dr. Wendy Wells at Dartmouth Hitchcock Medical Center. Samples were serially sectioned at 5 µm and mounted in positively-charged slides using floatation technique. Each slide contains two section representing normal and tumour samples from the same patient. One serial section was stained with hematoxylin (A-D, I-L, O-R) and another section from the same patient was used for detection of miRNAs by in situ hybridization. Two fields of the same section are displayed for each N and T samples. A-H) PS6 case is ER-PR-HER2+: miR-21 is detected high levels in the periphery of tumor mass (arrows on C-D and G-H point to the same structures); signal in N section does not come from epithelia (arrows on A and E), it is rather autofluorescence emanating from stroma and adipose tissue (arrows on B and F). I-P) PS2 case is ER+PR+HER2+: miR-145 is detected almost exclusively in N lobular and ductal epithelial structures (arrows on I-J and M-N), but not stroma; miR-145 expression is significantly downregulated in T section. Q-X) PS1 case is ER+PR+HER2-: miR-451 expression pattern and distribution in epithelial structures is very similar to miR-145 (arrows on O-P and S-T).

Figure 3:
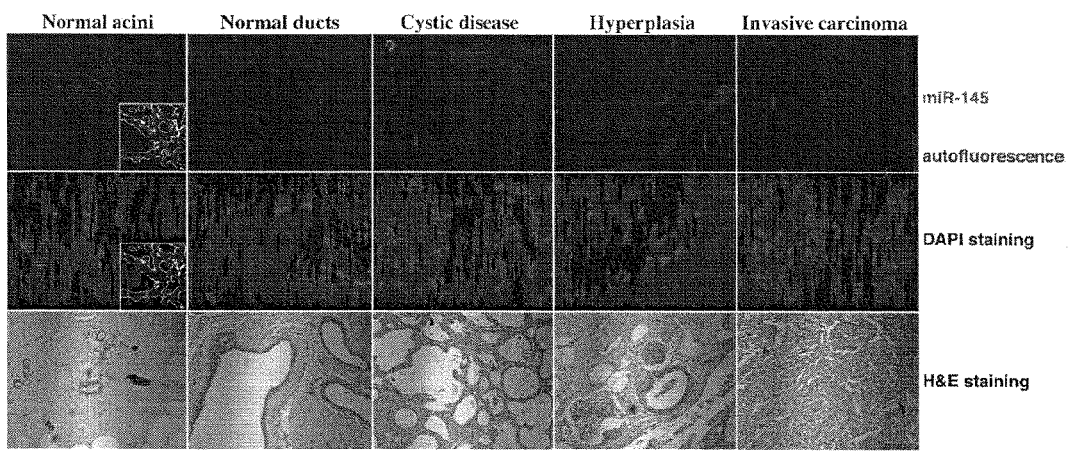
FIG. 3: Detection of miRNA expression by in situ hybridization using FITC-labeled LNA probes in FFPE sections from a breast cancer patient case showing a progression series from normal to malignant tissue. miR-145 expression is detected in fewer cells and at lower levels as the cells become malignant.

FIG. 3: Detection of miRNA expression by in situ hybridization using FITC-labeled LNA probes in FFPE sections from a breast cancer patient case showing a progression series from normal to malignant tissue. Specimen was prepared as described in FIG. 2. Top row panels show miR-145 expression in indicated tissue. Middle row panels display nuclei by DAPI staining of the same section specimens used for detection of miR-145 expression. Low row panels display hematoxylin and eosin staining of a different serial section used for detection of miR-145 expression. Inset of top left panel indicated that miR-145 is almost exclusively expressed in basal epithelial or myoepithelials cells, and not in luminal epithelial cells or surrounding stroma. miR-145 expression is detected in fewer cells and at lower levels as the cells become malignant. Tissue autoflouresence is indicated in red, and include signal emanating from erytrocytes and other cell types.

Figure 4:
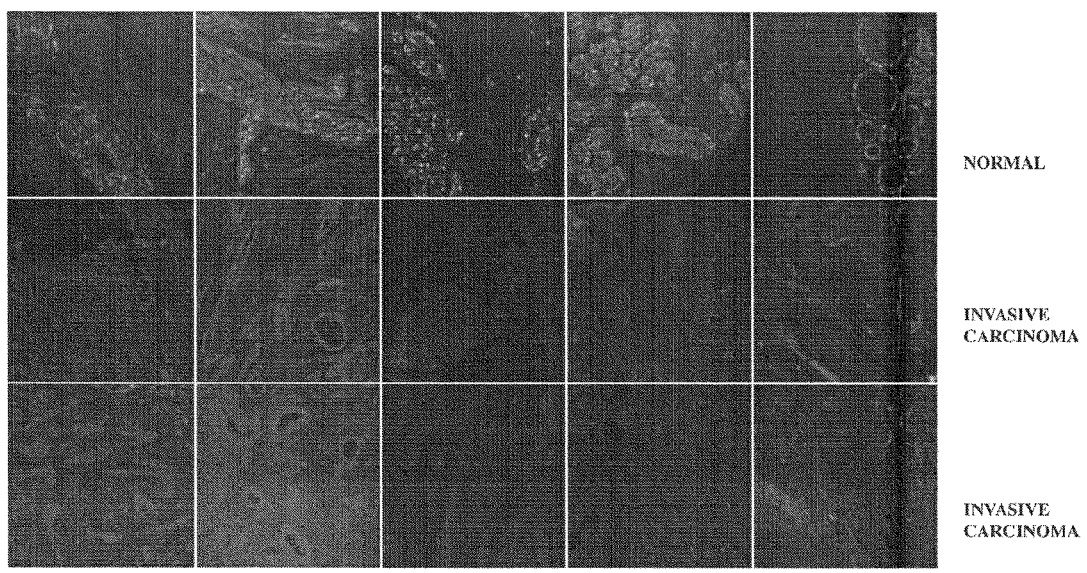
FIG. 4: Detection of miRNA expression by in situ hybridization using FITC-labeled LNA probes in 0.6 mm cores assembled in a tissue microarray from FFPE blocks of 59 breast cancer patients. Images of representative cases, used for data analysis in table VII, are shown.

FIG. 4: Detection of miRNA expression by in situ hybridization using FITC-labeled LNA probes in 0.6 mm cores assembled in a tissue microarray from FFPE blocks of 59 breast cancer patients. Images of five representative cases, used for data analysis in table VII, are shown. Upper panels display normal lobular and/or ductal epithelial structures. Mid and lower panel display two cores of invasive carcinoma from the same patient as the normal tissue above. miR-145 is clearly detected in normal epithelial structures in all five patient cases, and very faintly and/or sparsely in the invasive carcinoma tissue.

Figure 5:
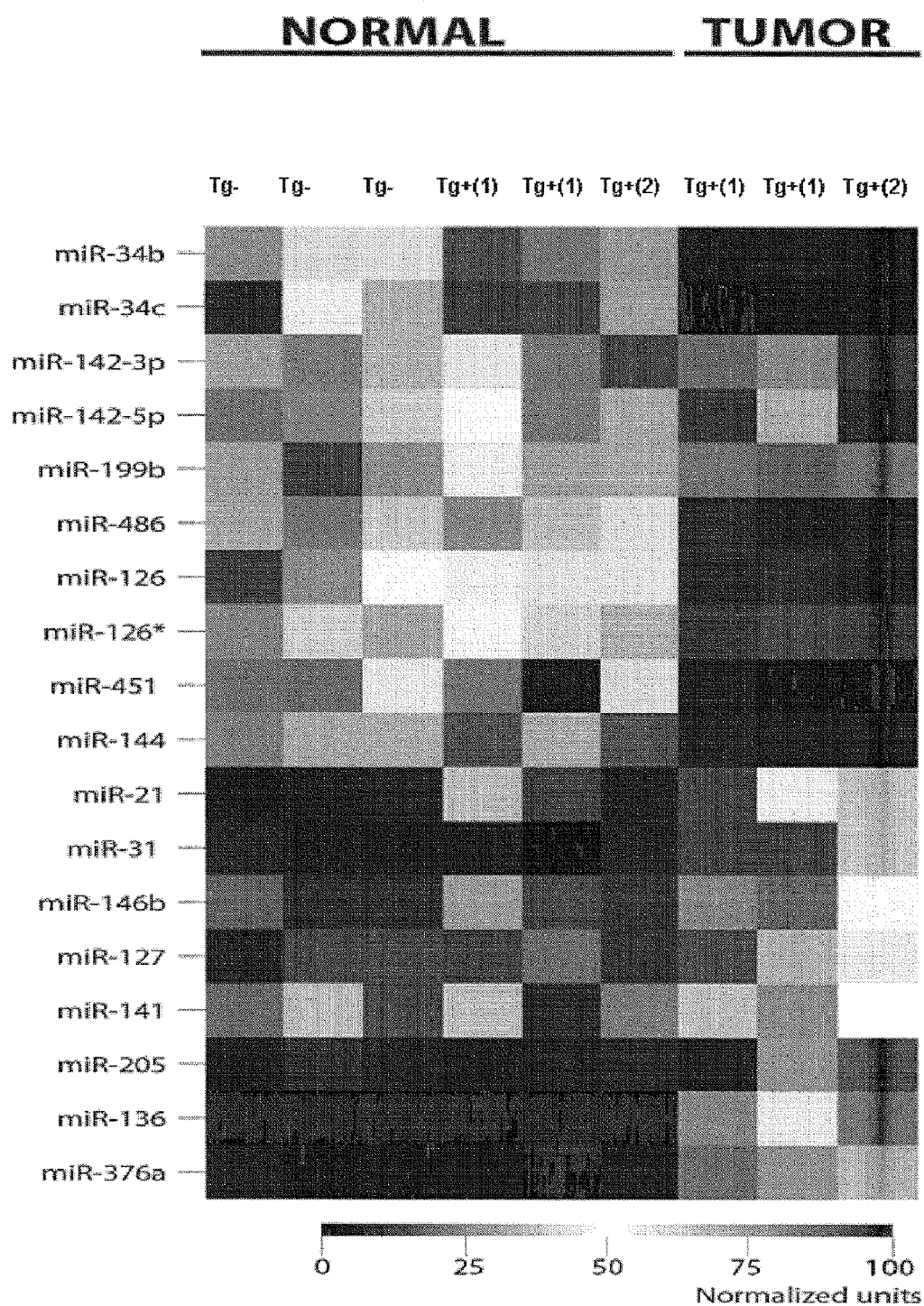
FIG. 5: Cluster analysis of miRNA expression in mouse lung specimens.

FIG. 5: Cluster analysis of miRNA expression in mouse lung specimens. Colour scale represents normalized units. For the expression of each miRNA, the highest value was arbitrarily set at 100 and the other values were set accordingly. The profiles display prominently repressed (black) or induced (medium grey) miRNAs in transgenic cyclin E adenocarcinomas from representative wild-type [Tg+(1)] and degradation resistant cyclin E [Tg+(2)] mice. Comparisons are made to expression profiles in adjacent normal lung. The two most repressed miRNAs in tumors were miR-34c and miR-142-5p. The two most abundantly expressed miRNAs were miR-136 and miR-376a. These are each novel species, not previously reported in human lung cancers. Results were confirmed in replicate arrays, each performed at least twice in three pairs of normal-malignant lung tissues from each line. Prior work in lung tumors recognised miR-199b, miR-126, miR-126*, miR-21, miR-146b and miR205 as being regulated. The novel miRNAs described here are detailed in Table A.

Figure 6:
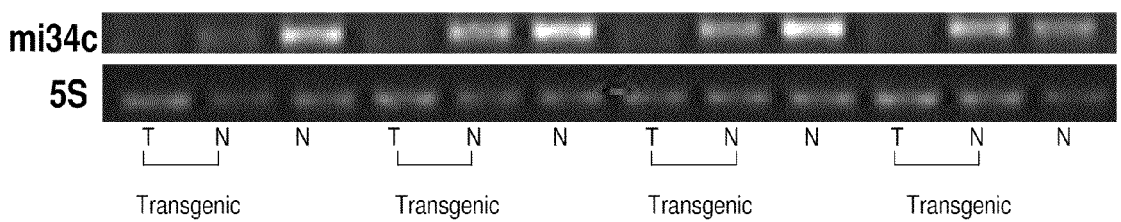
FIG. 6: Semi-quantitative RT-PCR assays for a representative miRNA (mi34c) differentially repressed in malignant versus normal lung from (A) transgenic mouse lines and from (B) paired human normal-malignant lung tissues.
Figure 6:
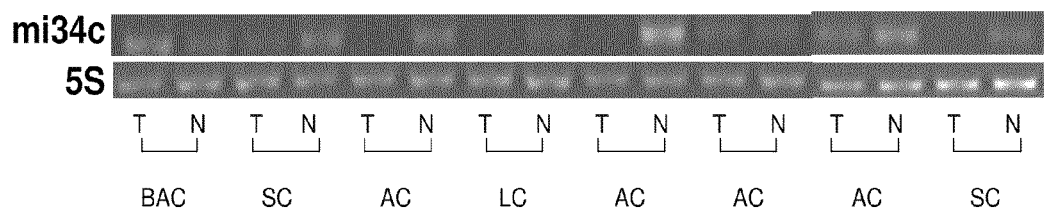

FIG. 6: Semi-quantitative RT-PCR assays for a representative miRNA (mi34C) differentially repressed in malignant versus normal lung from (A) transgenic mouse lines (first two pairs wild-type and second degradation-resistant) and from (B) paired human normal-malignant lung tissues (BAC, bronchioalveolar cancer, SC, squamous cell cancer, LC large cell cancer, and AC, adenocarcinoma). Similar profiles are found in these murine and human tissues, independently confirming the results obtained from gene profiling experiments and establishing the usefulness of these transgenic lines to predict miRNA expression patterns in human tissues.

Figure 7:
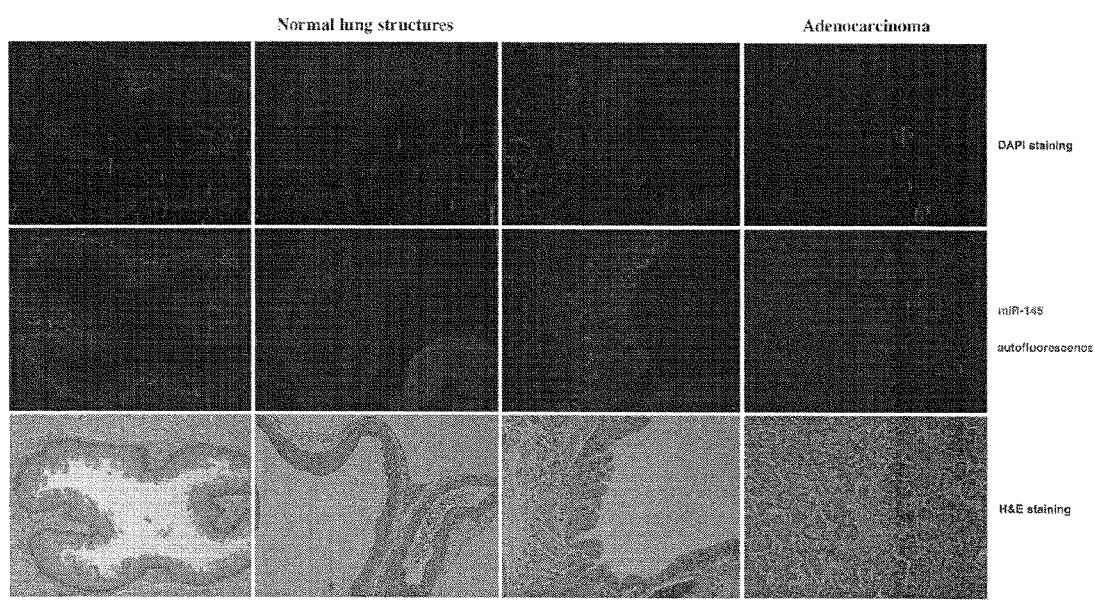
FIG. 7: Detection of miRNA expression by in situ hybridization using FITC-labeled LNA probes in FFPE sections of murine model of lung cancer.

FIG. 7: Detection of miRNA expression by in situ hybridization using FITC-labeled LNA probes in FFPE sections of murine model of lung cancer. Transgenic animals overexpressing human cyclin E were sacrificed. Lung tissue was dissected and fixed with 10% buffered formalin for at least 12 hrs. Then, samples were embedded in paraffin, serially sectioned at 5 µm and mounted in positively-charged slides using floatation technique. Each slide represents adjacent normal lung tissue and human cyclin E-induced displasia and adenocarcinoma. miR-145 is expressed abundantly in normal lung structures, but it is detected at low levels or completely absent in adenocarcinoma lesion.

Figure 8:
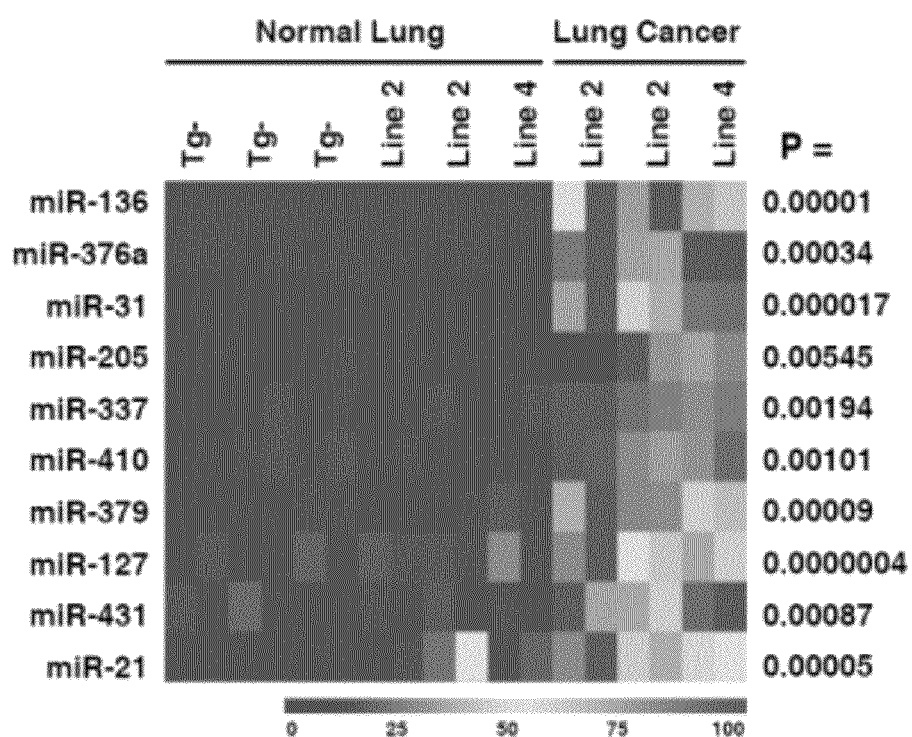
FIG. 8: Over-expressed miRNAs in murine transgenic lung cancers relative to adjacent normal lung tissues.
Figure 8:
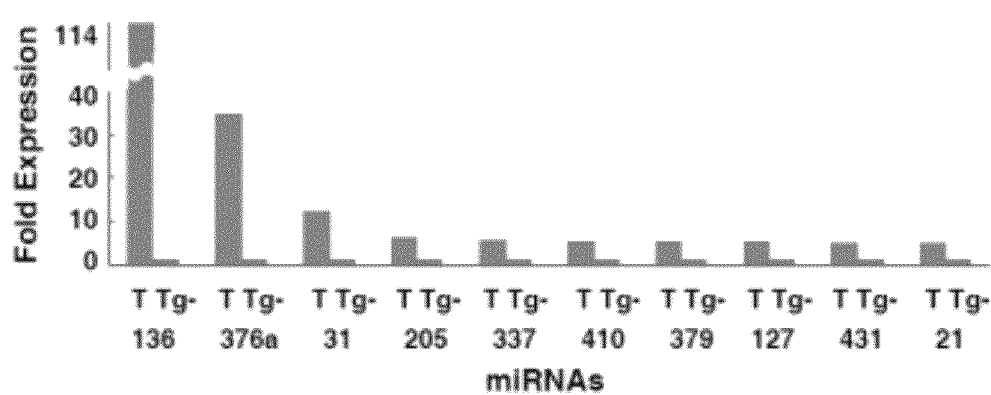

FIG. 8: The most prominently over-expressed miRNAs in murine transgenic lung cancers relative to adjacent normal lung tissues. A) miRNA profiling of lung adenocarcinomas and adjacent normal lung tissues from murine wild-type (line 2) and degradation-resistant (line 4) cyclin E transgenic lines. MiR-136, miR-376a, miR-31, miR-205, miR-337, miR-410, miR-379, miR-127, miR-431 and miR-21 were each significantly over-expressed in lung adenocarcinomas versus normal lung. B) Quantification is displayed of the over-expressed miRNAs in murine lung cancers versus normal lung tissues in panel A.

Figure 9:
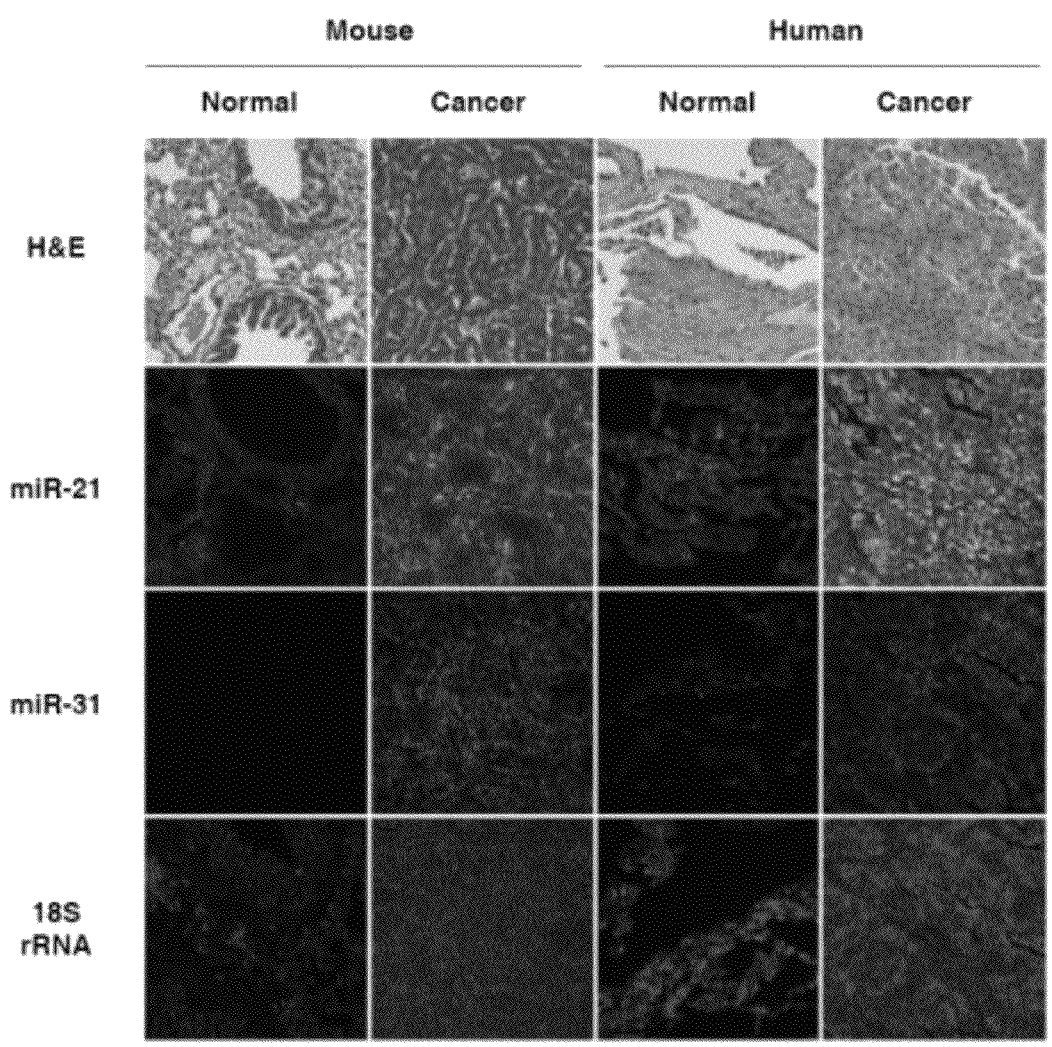
FIG. 9: ISH assays for representative over-expressed miRNAs in lung cancers

FIG. 9: ISH assays for representative over-expressed miRNAs in lung cancers. These assays were conducted on adenocarcinomas and adjacent normal lung tissues from cyclin E transgenic mice and from human paired normal-malignant lung tissues. Over-expression of miR-21 and miR-31 was detected in malignant versus normal lung tissues. The 18S rRNA signal served as a positive control for integrity of RNA. Hematoxylin and eosin (H&E) staining of the indicated tissue sections is shown.

Figure 10:
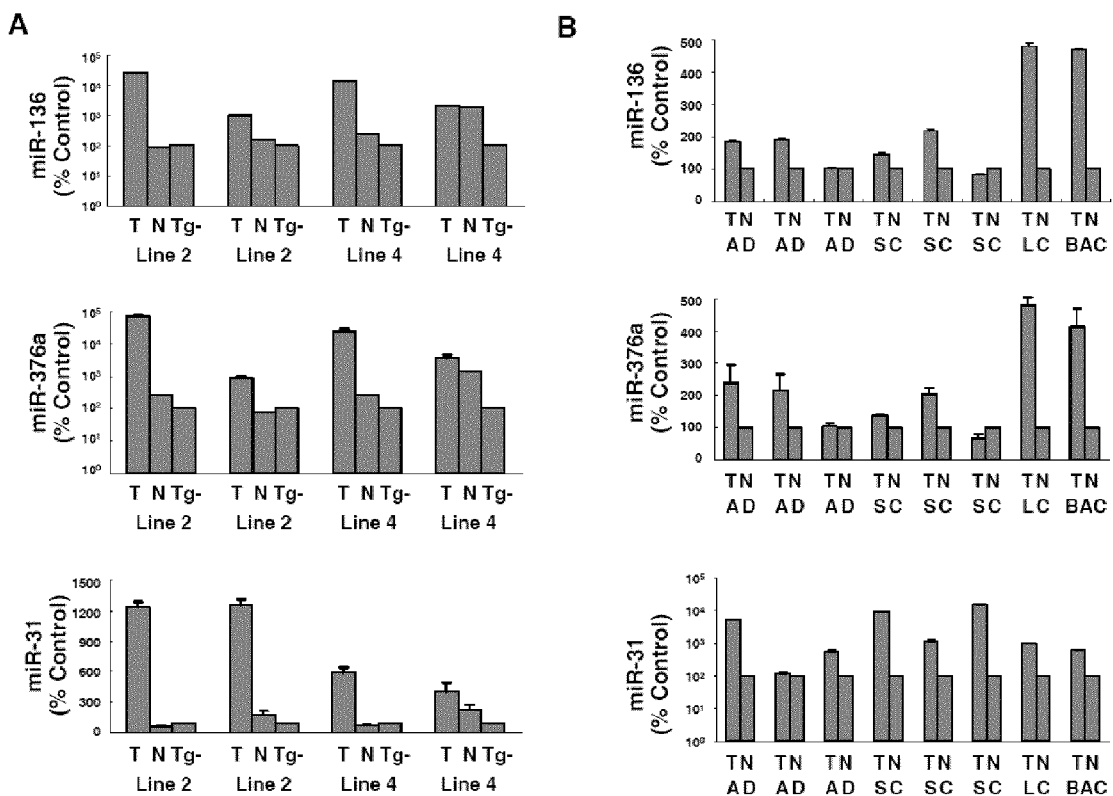
FIG. 10: Validation of miR-136, miR-376a and miR-31 expression profiles by real-time RT-PCR assays.

FIG. 10: Validation of miR-136, miR-376a and miR-31 expression profiles by real-time RT-PCR assays performed on RNA isolated from the indicated murine cyclin E transgenic lines and tissues from paired human normal-malignant lung tissues. A) Real-time RT-PCR assays for miR-136, miR-376a and miR-31 were performed with symbols depicting T, malignant tumor; N, adjacent normal murine lung; and Tg−, murine non-transgenic FVB normal lung tissue. Results were normalized to expression levels detected in FVB murine Tg− lung tissues. B) Real-time RT-PCR assays for miR-136, miR-376a and miR-31 were independently performed on paired human normal-malignant lung tissues, with symbols depicting T, malignant tumor; N, adjacent normal human lung; AD, adenocarcinoma; LC, large cell carcinoma; BAC, bronchioalveolar carcinoma; and SC, squamous cell carcinoma. Results were normalized to expression levels measured in normal human lung. Standard deviation bars are displayed.

Figure 11:
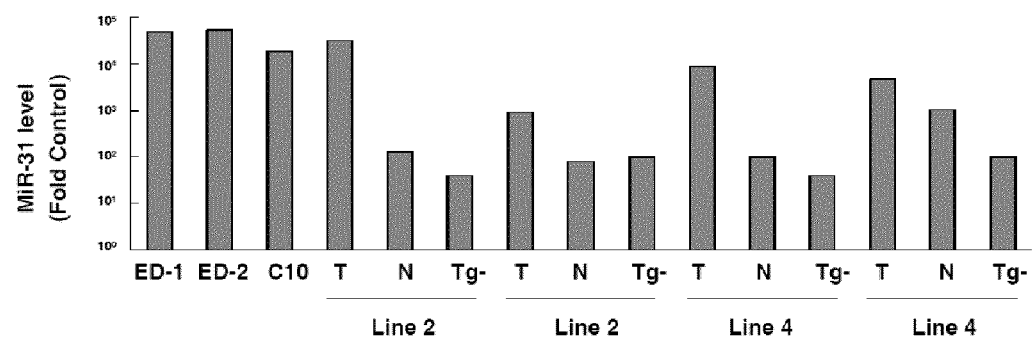
FIG. 11: Validation of miR-31 expression by real-time RT-PCR assays.
Figure 11:
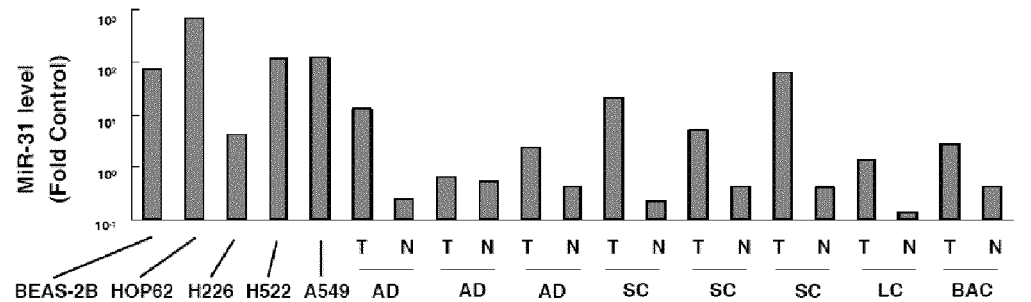

FIG. 11: Validation of miR-31 expression by real-time RT-PCR assays performed on the indicated cell lines as well as malignant and adjacent normal lung tissues from murine cyclin E transgenic lines and independently on paired normal-malignant human lung tissues. A) Real-time RT-PCR assays for miR-31 in murine ED-1, ED-2, C10 cells and murine cyclin E transgenic malignant versus normal lung tissues with symbols depicting T, malignant transgenic lung tumor; N, adjacent normal murine transgenic lung; and Tg−, murine non-transgenic FVB normal lung tissue. Results represented the fold changes of miR-31 expression relative to sno-135 (control small RNA). B) Real-time RT-PCR assays for miR-31 were performed on RNA derived independently from BEAS-2B, HOP62, H226, H522 and A549 cells as well as from paired human normal-malignant lung tissues, with symbols depicting T, malignant lung tumor; N, adjacent normal lung; AD, adenocarcinoma; LC, large cell carcinoma; BAC, bronchioalveolar carcinoma; and SC, squamous cell carcinoma. Results represented the fold of miR-31 relative to RNU6B (control small RNA).

Figure 12:
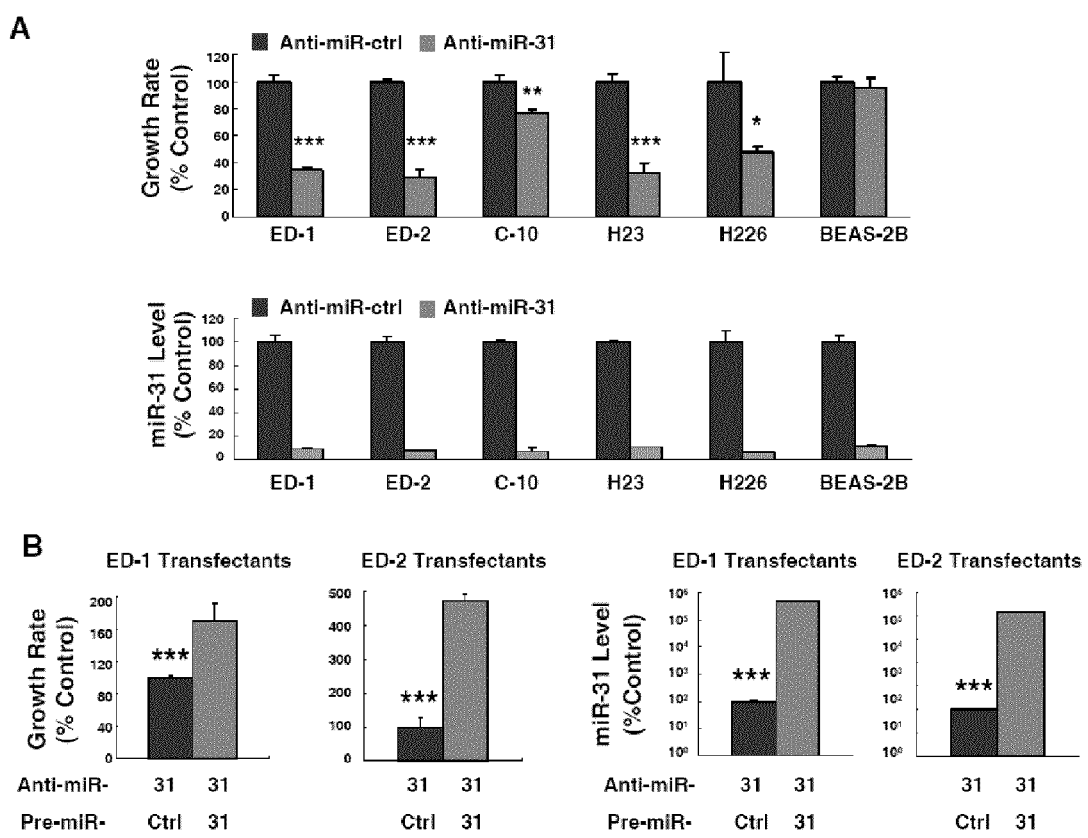
FIG. 12: Regulation of miR-31 expression affects lung cancer cell proliferation.

FIG. 12: Regulation of miR-31 expression affects lung cancer cell proliferation. A) Proliferation of ED-1 and ED-2 murine lung cancer cells and H23 and H226 human lung cancer cells was each suppressed by engineered miR-31 knock-down by anti-miR-31 transfection, but murine C10 pulmonary epithelial cell proliferation was less significantly suppressed and BEAS-2B human immortalized bronchial epithelial cell growth was not significantly suppressed by this transfection. The symbols are: *, P<0.05; , P<0.01; *, P<0.0001. The lower panel displays real-time RT-PCR assays that confirm miR-31 repression and all P values were <0.0001. B) Significant repression of ED-1 and ED-2 cell growth caused by anti-miR-31 was antagonized by transfection of pre-miR-31 at 48 hours after anti-miR-31 transfection. The left panel for each lung cancer cell line displays proliferation and the right panel presents the real-time RT-PCR assay results confirming the expected miR-31 expression levels of these transfectants. In all groups P values were <0.0001.

Figure 13:
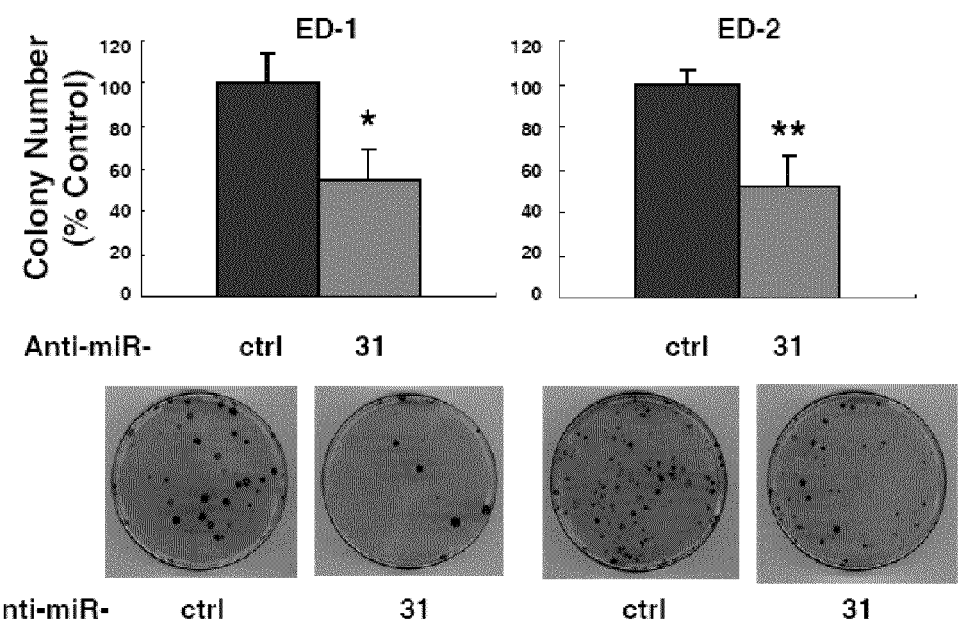
FIG. 13: Repression of miR-31 expression significantly affects murine lung cancer clonal growth and tumorigenicity.
Figure 13:
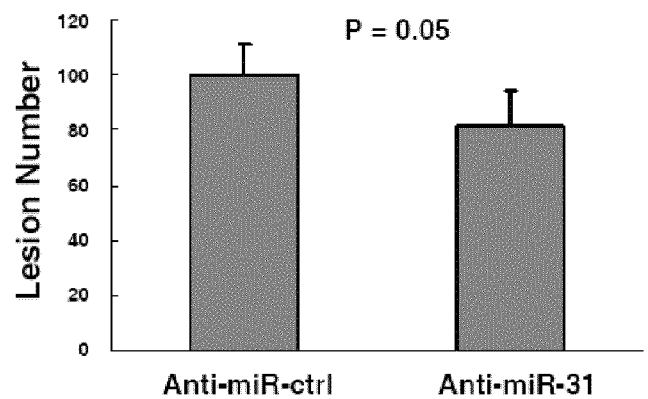

FIG. 13: Repression of miR-31 expression significantly affects murine lung cancer clonal growth and tumorigenicity. A) Colony formation assays for ED-1 and ED-2 murine lung cancer cells were independently suppressed relative to controls (ctrl) by engineered knock-down of miR-31 through transient anti-miR-31 transfection. The stained colonies are displayed in the lower panel. B) Repression of in vivo lung tumorigenicity in the indicated transfected ED-1 cells following FVB mouse tail-vein injections. The bars represent lesion numbers in the lungs. Forty mice in total were used and each group had 10 mice with results pooled from two independent experiments, as described in the Methods and Materials. The symbols displayed are: *, P<0.05; ** and P<0.01.

Figure 14:
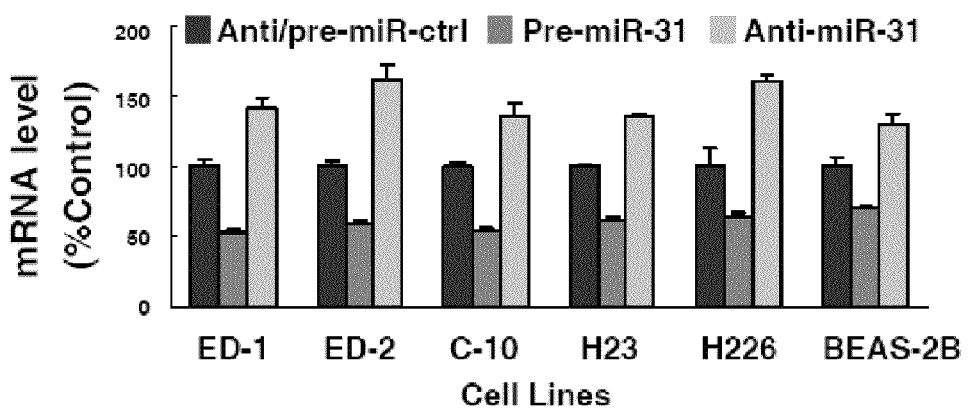
FIG. 14: LATS2 and PPP2R2A are miR-31 target mRNAs.
Figure 14:
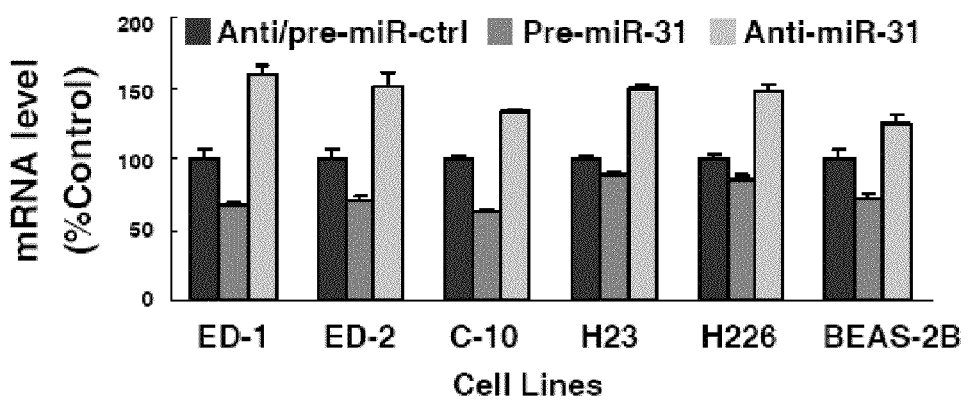

FIG. 14: LATS2 and PPP2R2A are miR-31 target mRNAs. Real-time RT-PCR assays confirmed that the A) LATS2 and B) PPP2R2A expression levels were each down-regulated by pre-miR-31 and up-regulated by anti-miR-31 transfections independently performed in ED-1, ED-2, C-10, H23, H226 and BEAS-2B cells. All transfectant groups had P values <0.0001.

Figure 15:
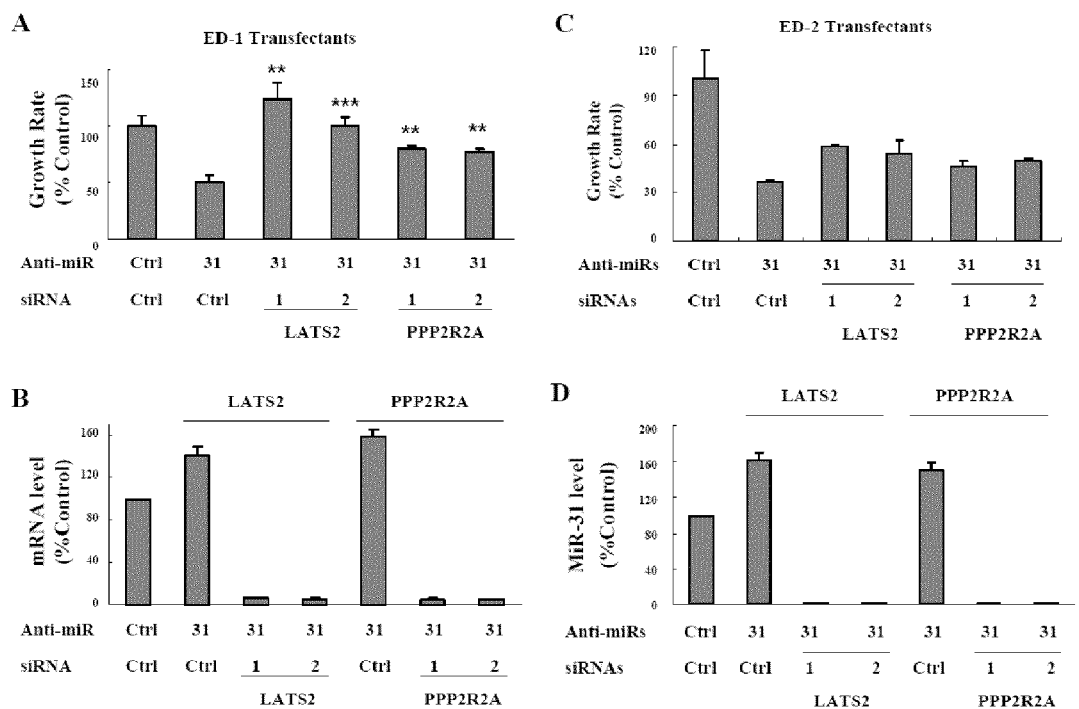
FIG. 15: Proliferation of murine lung cancer cells following regulated expression of miR-31, LATS2 or PPP2R2A.

FIG. 15: The proliferation of murine lung cancer cells following regulated expression of miR-31, LATS2 or PPP2R2A. The panels display A) ED-1 cells and C) ED-2 cells and their growth was suppressed by transfection of anti-miR-31. This was antagonized by either LATS2 or PPP2R2A targeting siRNA transfections performed 48 hours after anti-miR-31 transfection. Two independent siRNAs were each used to target LATS2 as well as PPP2R2A. The symbols displayed are: **, P<0.01 and P<0.0001. The mRNA levels of LATS2 and PPP2R2A are presented for the indicated transfectants in panels B) ED-1 cells and D) ED-2 cells following real-time RT-PCR assays. All results were normalized to the combined anti-miR-neg and the negative control siRNA transfectant group. In all groups P values were <0.0001.

Figure 16:
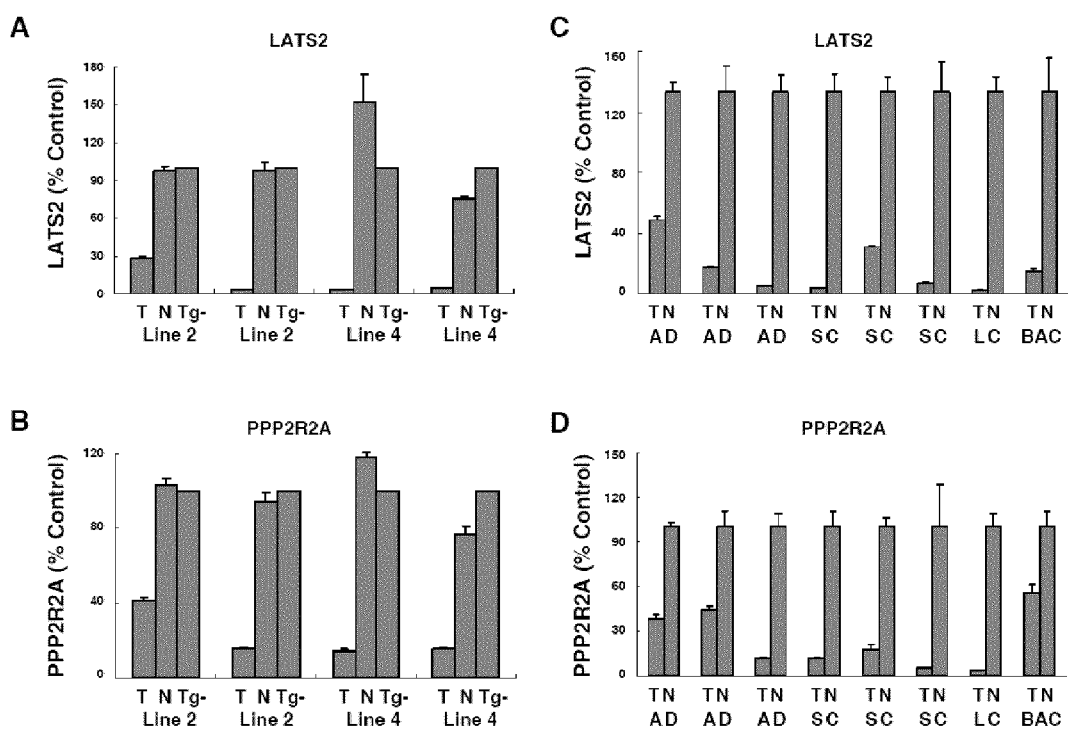
FIG. 16: Validation of LATS2 and PPP2R2A expression profiles by real-time RT-PCR assays

FIG. 16: Validation of LATS2 and PPP2R2A expression profiles by real-time RT-PCR assays performed on RNA isolated from the indicated murine cyclin E transgenic lines and tissues from paired human normal-malignant lung tissues. Real-time RT-PCR assays for: A) LATS2 and B) PPP2R2A were performed with symbols depicting T, malignant lung tumor; N, adjacent normal murine lung; and Tg-, murine non-transgenic FVB normal lung. Results were normalized to expression within non-transgenic FVB mouse lung tissues. Real-time RT-PCR assays for C) LATS2 and D) PPP2R2A were independently performed on paired human normal-malignant lung tissues, with symbols depicting T, malignant lung tumor; N, adjacent normal lung tissues; AD, adenocarcinoma; LC, large cell carcinoma; BAC, bronchioalveolar carcinoma; and SC, squamous cell carcinoma. Results were normalized to expression in normal human lung tissues. Standard deviation bars are displayed. In all groups P values were <0.001.

EXAMPLES

Example 1

Identification of Novel, Differentially Expressed Mirnas in Breast Tumours

Table I. The 10 breast cancer cases used to identify novel, differentially expressed miRNAs in example 1. Four of these cases, all which are ER+ (i.e. BC# 2, 4, 6, 8), have a matching normal tissue section. Most of these tumours are infiltrating ductal carcinomas, of high grade. These tumours represent a range of stages due to tumour size from 1.8 to 7.2 cm and node status.

| Brief name | Subtype | Comments | Type | Grade | Size | Nodes |
|---|---|---|---|---|---|---|
| BC#1 | ER+/PR+/HER2− | Normal | N/A | N/A | N/A | N/A |
| BC#2 | ER+/PR+/HER2− | ER+ Tumor | IDCa | LG | 1.8 cm | 1 of 4 |
| BC#3 | ER+/PR+/HER2− | Normal | N/A | N/A | N/A | N/A |
| BC#4 | ER+/PR+/HER2− | ER+ Tumor | IDCa | HG | 2.0 cm | 1 of 1 |
| BC#5 | ER+/PR+/HER2− | Normal | N/A | N/A | N/A | N/A |
| BC#6 | ER+/PR+/HER2− | ER+ Tumor | IDCa | HG | 7.0 cm | 3 of 7 |
| BC#7 | ER+/PR+/HER2− | Normal | N/A | N/A | N/A | N/A |
| BC#8 | ER+/PR+/HER2− | ER+ Tumor | IDCa | HG | 4.5 cm | Not done |
| BC#9 | ER−/PR−/HER2+ | ER− Tumor | IDCa | HG | 2.1 cm | 1 of 1 |
| BC#10 | ER−/PR−/HER2− | ER− Tumor | Met Ca | HG | 2.9 cm | 0 of 4 |
| BC#11 | ER−/PR−/HER2− | ER− Tumor | IDCa | HG | 2.8 cm | 0 of 7 |
| BC#12 | ER−/PR−/HER2+ | ER− Tumor | IDCa | HG | 3.3 cm | 19 of 22 |
| BC#13 | ER−/PR−/HER2− | ER− Tumor | IDCa | HG | 2.9 cm | 5 of 8 |
| BC#14 | ER−/PR−/HER2− | ER− Tumor | IDCa | HG | 7.2 cm | 17 of 20 |

Key for Table I definitions:
IDCa = infiltrating ductal carcinoma
Met Ca = metaplastic carcinoma
HG = high grade
IG = intermedoate grade
LG = low grade A) Isolation of the Breast Tumour Samples Tumour samples were obtained through the research pathology services at Dartmouth-Hitchcock Medical Center. Tumour samples were excised from patients as result of surgery (lumpectomies or mastectomies). Tumour samples from the operation room were delivered to surgical pathology laboratory for routine diagnosis and archive of the samples.

B) Total RNA Extraction

All breast tumour samples described in detail in Table I, were obtained as frozen specimens preserved in liquid nitrogen. Total RNA was extracted using Trizol reagent according to the manufacturer's instructions (Invitrogen).

C) RNA Labelling for miRNA Microarray Profiling

Total RNA extracted from the breast tumours (Table I) was 3' end labeled using T4 RNA ligase and Cy3- or Cy5-labeled RNA linker (5'-$PO_4$-rUrUrU-Cy3/dT-3' or 5'-$PO_4$-rUrUrU-Cy5/dT-3'). The labeling reactions contained 3.5 µg total RNA, 15 µM RNA linker, 50 mM Tris-HCl (pH 7.8), 10 mM $MgCl_2$, 10 mM DTT, 1 mM ATP, 16% polyethylene glycol and 5 unit T4 RNA ligase (Ambion, USA) and were incubated at 30° C. for 2 hours followed by heat inactivation of the T4 RNA ligase at 80° C. for 5 minutes.

D) Microarray Hybridization and Post-Hybridization Washes

LNA-modified oligonucleotide capture probes comprising probes for all annotated miRNAs annotated from mouse (*Mus musculus*) and human (*Homo sapiens*) in the miRBase MiRNA database Release 7.1 including a set of positive and negative control probes were purchased from Exiqon, Denmark and used to print the LNA microarray platform. The capture probes contain a 5'-terminal C6-amino modified linker and were designed to have a $T_m$ of 72° C. against complementary target miRNAs by adjustment of the LNA content and length of the capture probes. The capture probes were diluted to a final concentration of 10 µM in 150 mM sodium phosphate buffer (pH 8.5) and spotted in quadruplicate onto Codelink slides (Amersham Biosciences) using the MicroGrid II arrayer from BioRobotics at 45% humidity and at room temperature. Spotted slides were post-processed as recommended by the manufacturer.

Labelled RNA was hybridized to the LNA microarrays overnight at 65° C. in a hybridization mixture containing 4×SSC, 0.1% SDS, 1 µg/µl Herring Sperm DNA and 38% formamide. The hybridized slides were washed three times in 2×SSC, 0.025% SDS at 65° C., followed by three times in 0.08×SSC and finally three times in 0.4×SSC at room temperature.

E) Array Scanning, Image Analysis and Data Processing

The microarrays were scanned using the ArrayWorx scanner (Applied Precision, USA) according to the manufacturer's recommendations. The scanned images were imported into TIGR Spotfinder version 3.1 (Saeed et al., 2003) for the extraction of mean spot intensities and median local background intensities, excluding spots with intensities below median local background +4× standard deviations. Background-correlated intensities were normalized using variance stabilizing normalization package version 1.8.0 (Huber et al., 2002) for R (www.r-project.org). Intensities of replicate spots were averaged using Microsoft Excel. Probes displaying a coefficient of variance>100% were excluded from further data analysis.

Table II. Differential expression of nine different miRNAs in breast tumour samples as detected by LNA microarray expression profiling. The displayed expression levels show the average intensities from two or three replica experiments.

TABLE II

| miRNA name | Normal tissue | | | | ER+ tumors | | | | ER− tumors | | | | | |
|---|---|---|---|---|---|---|---|---|---|---|---|---|---|---|
| | BC#1 | BC#3 | BC#5 | BC#7 | BC#2 | BC#4 | BC#6 | BC#8 | BC#9 | BC#10 | BC#11 | BC#12 | BC#13 | BC#14 |
| miR-451 | 3624 | 6578 | 8308 | 1383 | 6051 | 2155 | 1132 | 193 | 150 | 452 | 857 | 1139 | 428 | 2166 |
| miR-143 | 1148 | 1947 | 1064 | 5161 | 1368 | 1177 | 812 | 1448 | 380 | 682 | 655 | 752 | 800 | 1108 |
| miR-145 | 2073 | 3054 | 702 | 4647 | 1290 | 1061 | 401 | 1280 | 245 | 392 | 348 | 368 | 504 | 598 |
| miR-21 | 1982 | 4776 | 4921 | 7810 | 13785 | 10311 | 5640 | 7095 | 2853 | 12869 | 12142 | 14472 | 8903 | 14917 |
| miR-141 | 506 | 423 | 845 | 386 | 318 | 796 | 2035 | 780 | 1224 | 752 | 2362 | 692 | 516 | 1255 |
| miR-200b | 968 | 1596 | 1777 | 1047 | 1145 | 2340 | 2283 | 1675 | 3614 | 1540 | 2393 | 2089 | 1503 | 1878 |
| miR-200c | 941 | 1232 | 1972 | 1410 | 577 | 1758 | 3324 | 1948 | 3840 | 1602 | 4814 | 2262 | 2362 | 2833 |

TABLE II-continued

| miRNA name | Normal tissue | | | | ER+ tumors | | | | ER− tumors | | | | | |
|---|---|---|---|---|---|---|---|---|---|---|---|---|---|---|
| | BC#1 | BC#3 | BC#5 | BC#7 | BC#2 | BC#4 | BC#6 | BC#8 | BC#9 | BC#10 | BC#11 | BC#12 | BC#13 | BC#14 |
| miR-221 | 803 | 920 | 1098 | 2057 | 1235 | 871 | 1013 | 1286 | 923 | 1294 | 1912 | 1141 | 913 | 1488 |
| miR-222 | 656 | 644 | 778 | 1645 | 805 | 624 | 734 | 1252 | 677 | 1068 | 1793 | 904 | 845 | 1263 |

Table III. Log 2-transformed expression ratios of nine microRNAs in breast tumour samples the indicated samples. The ER+ tumours (BC#2, 4, 6, 8) are paired with their matching normal tissue section, while BC#9-14 are paired with BC#N. BC #N represents the average expression of the given miRNAs in the normal tissue samples BC #1, 3, 5, 7 Positive log 2-ratios indicate upregulation, and negative values indicate downregulation of the given miRNA.

miRNA probes, membranes were hybridized for 24 h at 42° C. in 7% SDS. 0.2MNa2PO4, pH 7.2, and washed twice with 2×SSPE 0.1% SDS, and once with 1×SSPE 0.1% SDS, and 0.5×SSPE 0.1% SDS at 42° C. For U6 probe, membranes were hybridized overnight at 42° C. in 7% SDS 0.05 M Na2PO4, pH 7.2, and washed twice with 1×SSPE 0.1% SDS, and once with 0.5×SSPE 0.1% SDS and 0.1×SSPE 0.1% SDS at 42° C.

TABLE III

| miRNA name | ER+ tumors | | | | ER− tumors | | | | | |
|---|---|---|---|---|---|---|---|---|---|---|
| | BC#2/#1 | BC#4/#3 | BC#6/#5 | BC#8/#7 | BC#9/#N | BC#10/#N | BC#11/#N | BC#12/#N | BC#13/#N | BC#14/#N |
| miR-451 | 0.74 | −1.61 | −2.88 | −2.84 | −5.05 | −3.46 | −2.54 | −2.13 | −3.54 | −1.2 |
| miR-143 | 0.25 | −0.73 | −0.39 | −1.83 | −2.61 | −1.77 | −1.83 | −1.63 | −1.54 | −1.07 |
| miR-145 | −0.68 | −1.53 | −0.81 | −1.86 | −3.42 | −2.74 | −2.91 | −2.83 | −2.38 | −2.13 |
| miR-21 | 2.8 | 1.11 | 0.2 | −0.14 | −0.77 | 1.4 | 1.32 | 1.57 | 0.87 | 1.61 |
| miR-141 | −0.67 | 0.91 | 1.27 | 1.01 | 1.18 | 0.48 | 2.13 | 0.36 | −0.07 | 1.22 |
| miR-200b | 0.24 | 0.55 | 0.36 | 0.68 | 1.42 | 0.19 | 0.83 | 0.63 | 0.16 | 0.48 |
| miR-200c | −0.71 | 0.51 | 0.75 | 0.47 | 1.47 | 0.21 | 1.79 | 0.7 | 0.77 | 1.03 |
| miR-221 | 0.62 | −0.08 | −0.12 | −0.68 | −0.4 | 0.09 | 0.65 | −0.1 | −0.42 | 0.29 |
| miR-222 | 0.3 | −0.04 | −0.08 | −0.39 | −0.46 | 0.2 | 0.95 | −0.04 | −0.14 | 0.44 |

F) Northern Blot Analysis

Total RNA of each breast tissue sample (Table I), 5 µg per lane, in formamide loading buffer (Ambion) was heated at 90° C. for 3 min, and electrophoretically separated through a 12% denaturing urea-polyacrylamide gel at 125 V for 1.5 h in 1×TBE at 25° C. RNA was electrophoretically transferred to a Genescreen plus (NEN) at 80 V for 1 h in 0.5×TBE at 4° C. RNA was cross-linked to the membrane by UV irradiation (1200 mJ; Stratagene UV Stratalinker), subsequently the membrane was baked at 80° C. for 30 min. miRNA and snoRNA U6 antisense StarFire (Integrated DNA Technologies) radiolabeled probes were prepared by incorporation of [alpha-$^{32}$P]dATP 6000 Ci/mmol as recommended by the vendor. The StarFire probe sequences are listed below. For Table IV. Confirmation of differentially expressed miRNAs by Northern analysis in breast tumour samples. Expression of listed miRNAs was determined by Northern analysis in the same breast tumour samples:BC#1-14 (Table 1 and II) used for LNA microarray profiling. Radioactive signal of miRNA bands was quantified using ImageQuant and corrected using U6 as loading control. Relative intensities of miRNA expression levels are displayed (− no expression, + low signal to +++ highest signal). We observed a high concordance between microarray and Northern results.

In table IV, miR-451, -21, 141, 200b, -221, and -222 correspond to SEQ ID NOs 30, 31, 32, 33, 34 and 35, respectively.

TABLE IV

| miRNA name | Probe sequence | Normal tissue | | | | ER+ tumors | | | | ER− tumors | | | | | |
|---|---|---|---|---|---|---|---|---|---|---|---|---|---|---|---|
| | | BC#1 | BC#3 | BC#5 | BC#7 | BC#2 | BC#4 | BC#6 | BC#8 | BC#9 | BC#10 | BC#11 | BC#12 | BC#13 | BC#14 |
| miR-451 | AAACTCAGTAATGGTAACGGTTT | + | ++ | +++ | ++ | ++ | − | − | − | − | + | − | − | + | + |
| miR-21 | TCAACATCAGTCTGATAAGCTA | − | + | + | + | ++ | − | − | ++ | +++ | +++ | +++ | ++ | +++ | +++ |
| miR-141 | CCATCTTTACCAGACAGTGTT | − | − | − | − | − | − | − | − | ++ | ++ | ++ | + | ++ | +++ |
| miR-200b | GTCATCATTACCAGGCAGTATTA | − | − | + | − | − | − | + | + | +++ | +++ | ++ | + | + | + |

TABLE IV-continued

| miRNA name | Probe sequence | Normal tissue | | | | ER+ tumors | | | | | ER- tumors | | | | |
|---|---|---|---|---|---|---|---|---|---|---|---|---|---|---|---|
| | | BC#1 | BC#3 | BC#5 | BC#7 | BC#2 | BC#4 | BC#6 | BC#8 | BC#9 | BC#10 | BC#11 | BC#12 | BC#13 | BC#14 |
| miR-221 | GAAACCCAGC AGACAATGTA GCT | − | − | − | + | + | − | − | + | − | +++ | + | − | + | + |
| miR-222 | TCGATGTAGA CCGATGACCC AGAG | − | − | − | − | − | − | − | − | + | + | + | + | + | + |

Table V. Expression profiling of miRNAs by Northern analysis in an additional set of 11 normal/tumour matched samples. Tumour samples 5,6,7,8 (matched to normal 1,2,3,4, respectively) and unmatched 9 are ER+PR+HER2-tumours; tumour samples 14,15,16 (matched to normal 10,11,12,13, respectively) are ER+PR+HER2+ tumours; tumour samples 20,21 (matched to normal 18,19, respectively—though no significant amount of RNA was obtained from these normal samples) and unmatched 22 are ER-PR-HER2+ tumours; tumour samples 24 (matched to are normal 23) and unmatched 25 and 26 ER-PR-HER2-tumours (no significant amount of RNA was obtained). Experiments were conducted as described for Table IV. Samples 18,19, 25 and 26 were discarded from data analysis due to RNA underloading and thus, are not included in this table.

In table V, miR-143, -145, -451, -21, -141, and -221 correspond to SEQ ID NOs 36, 37, 30, 31, 32 and 34, respectively.

miR-143 and miR-145 were found down-regulated in all breast tumour samples studied in this example, while miR-21 and miR-141 were up-regulated in most of the tumour samples. miR-200b and miR-200c showed upregulation in some of the tumour samples. Northern analysis of examined miRNAs corroborates these findings.

Example 2

Determination of spatial distribution of selected miRNAs in formalin-fixed paraffin-embedded tumour sections by LNA in situ hybridization.

Table VI. In situ detection of four miRNAs in tumour sections of 9 cases of breast cancer. All these FFPE tumour sections were accompanied with a matching normal section from the same patient. This table summarizes results of the experiments looking at 5-10 random of each normal and

TABLE V

| miRNA name | Probe sequence | Normal tissue | | | | | | | | | | ER + TUMORS | | | | | | | ER − TUMORS | | | | | |
|---|---|---|---|---|---|---|---|---|---|---|---|---|---|---|---|---|---|---|---|---|---|---|---|---|
| | | 1 | 2 | 3 | 4 | 10 | 11 | 12 | 13 | 18 | 19 | 23 | 5 | 6 | 7 | 8 | 9 | 14 | 15 | 16 | 17 | 20 | 21 | 22 | 24 | 25 | 26 |
| miR-143 | TGAGCTA CAGTGCT TCATCTC A | + | + | ++ | + | +++ | + | + | − | * | * | ++ | + | − | + | + | − | +++ | + | + | + | + | + | + | + | − | + |
| miR-145 | AAGGGAT TCCTGGG AAAACTG GAC | ++ | ++ | ++ | ++ | ++ | +++ | ++ | − | * | * | ++ | + | + | + | − | − | + | + | + | + | + | + | + | − | − | − |
| miR-451 | AAACTCA GTAATGG TAACGGT TT | − | − | − | − | +++ | − | − | − | * | * | + | − | − | − | − | − | + | − | − | + | + | − | − | − | − | − |
| miR-21 | TCAACAT CAGTCTG ATAAGCT A | − | − | − | − | ++ | − | − | − | * | * | + | + | + | + | ++ | − | ++ | ++ | − | ++ | +++ | + | + | ++ | + | + |
| miR-141 | CCATCTT TACCAGA CAGTGTT | + | − | + | + | + | + | − | − | * | * | + | ++ | − | ++ | +++ | + | +++ | +++ | + | + | ++ | + | + | + | − | + |
| miR-221 | GAAACCC AGCAGAC AATGTAG CT | + | − | ++ | + | + | + | + | − | * | * | + | + | − | ++ | + | − | ++ | + | + | + | − | ++ | + | + | − | − |

G) Results

Analysis of the miRNA microarray data revealed that miR-451 was significantly down-regulated in all high grade ER-positive breast tumours as well as in all ER-negative tumours, compared to the normal breast samples. In addition, both tumour section fields under the epifluorescence microscope. Signal intensity was visually quantified from no expression (0) to high expression (3) in stroma and epithelial structures (lobules and milk ducts) for normal section and only in tumour mass for tumour section.

TABLE VI

| Subtype | Patient Case | Tumor Grade | miR-21 Stroma | miR-21 EpiStruct | miR-21 Tumor | miR-141 Stroma | miR-141 EpiStruct | miR-141 Tumor | miR-145 Stroma | miR-145 EpiStruct | miR-145 Tumor | miR-451 Stroma | miR-451 EpiStruct | miR-451 Tumor |
|---|---|---|---|---|---|---|---|---|---|---|---|---|---|---|
| ER+/PR+/HER2− | PS1 | IG | 0 | 2 | 0 | N/A | N/A | N/A | 0 | 2 | 0 | 0 | 3 | 0 |
| ER+/PR+/HER2− | PS2 | HG | 0 | 1 | 0 | N/A | N/A | N/A | 0 | 3 | 1 | 1 | 2 | 0 |
| ER+/PR+/HER2− | PS3 | HG | N/A | N/A | N/A | 0 | 0 | 0 | 1 | 3 | 1 | 0 | 1 | 0 |
| ER+/PR+/HER2+ | PS4 | HG | 1 | 0 | 2 | 0 | 1 | 0 | 0 | 2 | 0 | 0 | 1 | 0 |
| ER+/PR+/HER2+ | PS5 | HG | 0 | 1 | 2 | N/A | N/A | N/A | 0 | 3 | 0 | 0 | 2 | 0 |
| ER−/PR−/HER2+ | PS6 | HG | 0 | 1 | 3 | 1 | 1 | 1 | 0 | 2 | 1 | 0 | 1 | 1 |
| ER−/PR−/HER2+ | PS7 | HG | 0 | 0 | 0 | 0 | 1 | 0 | 0 | 3 | 0 | N/A | N/A | N/A |
| ER−/PR−/HER2− | PS8 | HG | N/A | N/A | N/A | N/A | N/A | N/A | 0 | 2 | 0 | N/A | N/A | N/A |
| ER−/PR−/HER2− | PS9 | HG | 0 | 0 | 0 | 1 | 1 | 2 | 0 | 2 | 0 | 0 | 1 | 1 |

Definitions
IG = intermedoate grade
HG = high grade
EpiStruct = Epithelial structures (ducts and lobules)

5'FITC-labeled LNA probes complementary for hsa-miR-21, hsa-miR-141, hsa-miR-145 and hsa-miR451 were purchased from Exiqon, Denmark and used in this in situ hybridization experiments. In situs with miR-200 and miR-222 required optimization.

Table VII. In situ detection of miR-145 in 0.6 mm core of a tissue microarray representing normal, in situ carcinoma and invasive carcinoma tissue from 59 breast cancer patients. This table summarizes of tissue microarray experiment for miR-145 expression. Tissue microarrays were hybridized in two independent experiments with LNA probes against miR-145. Signal intensity was visually quantified from no expression (0) to high expression and continuous pattern of expression (3). No signal is represented with 0, low expression/expressing cells are sparsely distributed and represented with +, intermediate expression/discontinuous or intermittent pattern of expression is represented with ++, high expression/continuous pattern is represented with +++. Cores that did not represent the appropriate tissue and or had insufficient material to diagnose are indicated with *. Cases are sorted descendingly by signal in normal tissue.

TABLE VII

| miR-145 | 3 | 16 | 18 | 43 | 49 | 35 | 1 | 5 | 28 | 54 | 31 | 30 | 39 | 51 | 37 |
|---|---|---|---|---|---|---|---|---|---|---|---|---|---|---|---|
| Normal | +++ | +++ | +++ | +++ | +++ | +++ | +++ | +++ | +++ | +++ | ++ | ++ | ++ | ++ | ++ |
| Carcinoma in situ | * | * | * | * | 0 | 0 | 0 | + | ++ | ++ | * | * | 0 | 0 | 0 |
| Invasive Carcinoma | 0 | 0 | 0 | 0 | 0 | 0 | * | 0 | 0 | * | 0 | 0 | 0 | 0 | + |
| Invasive Carcinoma | 0 | 0 | 0 | 0 | 0 | 0 | 0 | 0 | 0 | * | 0 | 0 | * | 0 | * |

| miR-145 | 58 | 33 | 7 | 25 | 2 | 6 | 34 | 48 | 15 | 46 | 27 | 41 | 44 | 45 | 14 |
|---|---|---|---|---|---|---|---|---|---|---|---|---|---|---|---|
| Normal | ++ | ++ | ++ | + | + | + | + | + | + | + | + | + | + | + | 0 |
| Carcinoma in situ | 0 | 0 | + | * | * | * | * | 0 | 0 | 0 | 0 | 0 | + | + | 0 |
| Invasive Carcinoma | ++ | * | 0 | 0 | 0 | 0 | * | * | 0 | 0 | 0 | 0 | 0 | 0 | 0 |
| Invasive Carcinoma | 0 | * | 0 | 0 | 0 | 0 | * | 0 | 0 | * | 0 | 0 | 0 | 0 | 0 |

| miR-145 | 26 | 11 | 12 | 17 | 55 | 56 | 20 | 29 | 9 | 19 | 22 | 23 | 36 | 50 | 52 | 32 | 40 | 42 |
|---|---|---|---|---|---|---|---|---|---|---|---|---|---|---|---|---|---|---|
| Normal | 0 | 0 | 0 | 0 | * | * | * | * | * | * | * | * | * | * | * | * | * | * |
| Carcinoma in situ | 0 | 0 | 0 | 0 | * | * | * | * | * | * | * | * | * | * | * | 0 | 0 | 0 |
| Invasive Carcinoma | 0 | 0 | 0 | 0 | * | * | 0 | 0 | 0 | 0 | 0 | 0 | 0 | 0 | * | 0 | 0 | 0 |
| Invasive Carcinoma | 0 | 0 | * | 0 | * | 0 | 0 | 0 | 0 | 0 | 0 | * | 0 | 0 | 0 | 0 | * | 0 |

TABLE VII-continued

| miR-145 | 13 | 4 | 8 | 24 | 38 | 47 | 53 | 10 | 21 | 57 |
|---|---|---|---|---|---|---|---|---|---|---|
| Normal | * | * | * | * | * | * | * | * | * | * |
| Carcinoma in situ | 0 | + | + | + | + | + | 0 | * | * | 0 |
| Invasive Carcinoma | * | 0 | 0 | 0 | 0 | 0 | 0 | * | 0 | * |
| Invasive Carcinoma | 0 | 0 | 0 | 0 | 0 | * | 0 | * | 0 | * |

A) Preparation of the Formalin-Fixed, Paraffin-Embedded Sections for In Situ Hybridization Archival paraffin-embedded samples were retrieved and examined by surgical pathologist Dr. Wendy Wells at Dartmouth Hitchcock Medical Center. Samples were serially sectioned at 5 μm and mounted in positively-charged slides using floatation technique. Each slide contains two sections representing normal and tumour samples from the same patient or 0.6 mm cores from tissue microarray blocks. Slides were stored at 4° C. until the experiments were conducted. The molecular and clinical history of these samples is available to us. These samples represent breast cancer subtypes (ER+vs ER− and HER2+ vs HER2−).

B) In Situ Hybridization

Sections on slides were deparaffinized in xylene and then rehydrated through an ethanol dilution series (from 100% to 25%). Slides were submerged in DEPC-treated water and subject to HCl and 0.2% Glycine treatment, re-fixed in 4% paraformaldehyde and treated with acetic anhydride/triethanolamine; slides were rinse in several washes of 1×PBS in-between treatments. Slides were pre-hybridized in hyb solution (50% formamide, 5×SSC, 500 mg/mL yeast tRNA, 1×Denhardt) at 50° C. for 30 min. Then, 3 pmol of the FITC-labeled LNA probe complementary to each selected miRNA was added to the hyb. solution and hybridized for one hr at a temperature 20-25° C. below the predicted $T_m$ of the probe (typically between 45-55° C. depending on the miRNA). After washes in 0.1× and 0.5×SCC at 65° C., a tyramide signal amplification reaction was carried out using the Genpoint Fluorescein (FITC) kit (DakoCytomation, Denmark) following the vendor's recommendations. Finally, slides were mounted with Prolong Gold solution. Fluorescence reaction was allowed to develop for 16-24 hr before documenting expression of the selected miRNA with epifluorescence microscope.

C) Results

The results show that miR-145 and miR-451 were specifically expressed within epithelial structures of normal tissue, whereas no expression or low expression (in HER2+ tumours) was detected in tumour sections with the exception of normal epithelial structures flanking the tumour mass. This demonstrates that miR-145 and miR-451 are expressed in the epithelial cells from which the carcinoma arises and thus the absence of these miRNAs in the tumour mass strongly suggest that they are downregulated as a direct consequence of the evolution of tumour. In some instances, miR-21 and miR-141 expression was upregulated in the tumour mass, whereas no signal or low signal was observed in normal stroma and/or epithelial structures. This is in agreement with the expression data obtained by microarray profiling and Northern analysis in example 1.

Example 3

The Novel microRNA Biomarker Sequences

1. The following miRNAs are downregulated in breast tumours compared to normal breast biopsies both analyzing whole samples by Northern and LNA microarray technique and analyzing spatial distribution of miRNAs within epithelial structures of breast tissue by in situ hybridization technique:

```
A) hsa-miR-451;
5'-aaaccguuaccauuacugaguuu-3'        (SEQ ID NO: 1)

B) hsa-miR-143;
5'-ugagaugaagcacuguagcuca-3'         (SEQ ID NO: 2)

C) hsa-miR-145;
5'-guccaguuuucccaggaaucccuu-3'       (SEQ ID NO: 3)
```

2. The following miRNAs are upregulated in specific subtypes of breast tumours compared to normal breast biopsies and in some instance additional evidence of this fact was obtained by in situ hybridization technique:

```
A) hsa-miR-141;
5'-uaacacugucugguaaagaugg-3'         (SEQ ID NO: 4)

B) hsa-miR-200b;
5'-uaauacugccugguaaugaugac-3'        (SEQ ID NO: 5)

C) hsa-miR-200c;
5'-uaauacugccgguaaugaugg-3'          (SEQ ID NO: 6)

D) hsa-miR-221;
5'-agcuacauugucugcugggsuuuc-3'       (SEQ ID NO: 7)

E) hsa-miR-222;
5'-agcuacaucuggcuacugggucuc-3'       (SEQ ID NO: 8)

F) hsa-miR-21;
5'-uagcuuaucagacugauguuga-3'         (SEQ ID NO: 17)
```

Table VIII. Chromosomal location of miRNAs as listed in miRbase. Notice that differentially expressed miRNAs are tightly linked in the genome and are related in sequence with the exception of miR-143 and miR-145 and miR-144 and miR-451. Tightly linked or clustered miRNAs are thought to be regulated by the common regulatory signals and in most cases are co-transcribed in a long primary transcript from which individual miRNA hairpin precursors are processed.

| miRNA | Accession nr | Chrom# | from | to |
|---|---|---|---|---|
| hsa-mir-200b | MI0000342 | 1 | 1142407 | 1142501 |
| hsa-mir-200a | MI0000737 | 1 | 1143166 | 1143255 |
| hsa-mir-429 | MI0001641 | 1 | 1144308 | 1144390 |
| hsa-mir-143 | MI0000459 | 5 | 148788674 | 148788779 |
| hsa-mir-145 | MI0000461 | 5 | 148790402 | 148790489 |
| hsa-mir-200c | MI0000650 | 12 | 6943123 | 6943190 |
| hsa-mir-141 | MI0000457 | 12 | 6943521 | 6943615 |
| hsa-mir-451 | MI0001729 | 17 | 24212513 | 24212584 |
| hsa-mir-144 | MI0000460 | 17 | 24212677 | 24212762 |
| hsa-mir-221 | MI0000298 | X | 45361839 | 45361948 |
| hsa-mir-222 | MI0000299 | X | 45362675 | 45362784 |
| hsa-mir-21 | MI0000077 | 17 | 55273409 | 55273480 |

Example 4

Method for Quantification of mRNA Levels by Real-Time RT-PCR Assay

First strand cDNA synthesis is carried out using 1 μg of a total RNA, random hexamer primers and SuperScript II reverse transcriptase. Following spin column purification the volume of the cDNA preparation is adjusted to 100 μl per 1 μg input total RNA and used as template in the real-time PCR reaction. Quantitative real-time PCR assays for the mRNA of interest is performed using 1× TaqMan Universal PCR Master Mix, No AmpErase UNG and 1× TaqMan Assays-on-Demand, Gene Expression Product for the given mRNA (or 1× TaqMan Pre-Developed Assay Reagent endogenous control for the β-actin mRNA (TaqMan PDAR human ACTB; Cat no. 4310881E) in an ABI 7900HT Sequence Detection System as follows: 10 min denaturation at 95° C. followed by 40 cycles of denaturation for 15 s at 95° C. and annealing and elongation for 1 min at 60° C. using 2 μL of the five times diluted cDNA reaction from above as template in a final volume of 25 μL. The relative gene expression level of the mRNA can be calculated as described in the user bulletin #2: ABI PRISM 7700 Sequence Detection System. Unless otherwise stated all reagents and equipment are purchased from Applied Biosystems, USA.

Example 5

Methods for Real-Time Quantification of Mature miRNAs by Stem-Loop RT-PCR

Reverse Transcriptase Reaction

The reverse transcriptase reaction is carried out using 1-25 ng of purified total RNA, 50 nM stem-loop RT primer for a given miRNA (Applied Biosystems, USA), 1× RT buffer (Applied Biosystems, USA), 0.25 mM each of dNTPs, 3.33 U/μl MultiScribe reverse transcriptase (Applied Biosystems, USA) and 0.25 U/μl RNase inhibitor (Applied Biosystems, USA). The 7.5 μl reactions are incubated in an Applied Biosystems 9700 Thermocycler in a 96- or 384-well plate for 30 min at 16° C., 30 min at 42° C., 5 min at 85° C. and then held at 4° C. The reactions, including no-template controls and RT minus controls, are run in duplicate.

Quantification by Real-Time PCR

Real-time PCR is performed using a standard TaqMan PCR kit protocol on an Applied Biosystems 7900HT Sequence Detection System (Applied Biosystems, USA). The 10 μl PCR includes 0.67 μl RT product, 1× TaqMan Universal PCR Master Mix (Applied Biosystems, USA), 0.2 μM TaqMan probe, 1.5 μM forward primer and 0.7 μM reverse primer. The reactions are incubated in a 384-well plate at 95° C. for 10 min, followed by 40 cycles of 95° C. for 15 s and 60° C. for 1 min. All reactions are run in triplicate. The threshold cycle (CT) is defined as the fractional cycle number at which the fluorescence passes the fixed threshold. TaqMan CT values are converted into absolute copy numbers using a standard curve from synthetic lin-4 miRNA.

Example 6

List of Putative Target Genes for Human miR-451

Table IX. List of exemplary target genes for human miR-451 as predicted by the miRBase Targets version 2.0 program (http COLON SLASH SLASH microrna DOT sanger DOT ac DOT uk/targets/v2/). (Hyperlink deactivated by replacing "://" with "COLON SLASH SLASH", and "." with "DOT".)

TABLE IX

| Gene Name | Transcript id | Description | P value | Total Sites | No. Cons Spec |
|---|---|---|---|---|---|
| FTS | ENST00000300245 | Fused toes protein homolog (Ft1). [Source: Uniprot/SWISSPROT; Acc: Q9H8T0] | 1.51E−06 | 1 | 8 |
| NP_054907.1 | ENST00000291386 | Ssu72 RNA polymerase II CTD phosphatase homolog [Source: RefSeq_peptide; Acc: NP_054907] | 1.85E−05 | 1 | 6 |
| ING3 | ENST00000315870 | Inhibitor of growth protein 3 (p47ING3 protein). [Source: Uniprot/SWISSPROT; Acc: Q9NXR8] | 2.98E−05 | 3 | 8 |
| NSMAF | ENST00000038176 | Protein FAN (Factor associated with N-SMase activation) (Factor associated with neutral-sphingomyelinase activation). [Source: Uniprot/SWISSPROT; Acc: Q92636] | 4.75E−05 | 1 | 6 |
| PITPNB | ENST00000320996 | Phosphatidylinositol transfer protein beta isoform (PtdIns transfer protein beta) (PtdInsTP) (PI-TP-beta). [Source: Uniprot/SWISSPROT; Acc: P48739] | 5.74E−05 | 1 | 7 |
| PHTF2 | ENST00000248550 | putative homeodomain transcription factor 2 [Source: RefSeq_peptide; Acc: NP_065165] | 6.01E−05 | 1 | 6 |
| PMM2 | ENST00000268261 | Phosphomannomutase 2 (EC 5.4.2.8) (PMM 2). [Source: Uniprot/SWISSPROT; Acc: O15305] | 6.09E−05 | 1 | 5 |
| APXL | ENST00000275869 | Apical-like protein (APXL protein). [Source: Uniprot/SWISSPROT; Acc: Q13796] | 8.09E−05 | 1 | 4 |

TABLE IX-continued

| Gene Name | Transcript id | Description | P value | Total Sites | No. Cons Spec |
|---|---|---|---|---|---|
| NEDD9 | ENST00000265010 | Enhancer of filamentation 1 (HEF1) (CRK-associated substrate-related protein) (CAS-L) (CasL) (p105) (Neural precursor cell expressed developmentally down-regulated 9). [Source: Uniprot/SWISSPROT; Acc: Q14511] | 8.21E-05 | 1 | 9 |
| TRAF7 | ENST00000326181 | E3 ubiquitin protein ligase TRAF7 (EC 6.3.2.—) (TNF receptor-associated factor 7) (Ring finger and WD repeat domain 1) (RING finger protein 119). [Source: Uniprot/SWISSPROT; Acc: Q6Q0C0] | 9.31E-05 | 1 | 5 |
| TMEM33 | ENST00000264452 | Transmembrane protein 33 (DB83 protein). [Source: Uniprot/SWISSPROT; Acc: P57088] | 9.46E-05 | 3 | 4 |
| NP_060498.2 | ENST00000314471 | PREDICTED: similar to CDNA sequence BC042901 [Source: RefSeq_peptide_predicted; Acc: XP_218384] PREDICTED: similar to CDNA sequence BC042901 [Source: RefSeq_peptide_predicted; Acc: XP_218384] BY ORTHOLOGY TO: ENSRNOT00000026839 | 0.000108 | 1 | 5 |
| LDHA | ENST00000227157 | L-lactate dehydrogenase A chain (EC 1.1.1.27) (LDH-A) (LDH muscle subunit) (LDH-M) (Proliferation-inducing gene 19 protein). [Source: Uniprot/SWISSPROT; Acc: P00338] | 0.000109 | 1 | 5 |
| MORC4_HUMAN | ENST00000255495 | MORC family CW-type zinc finger 4 (Zinc finger CW-type coiled-coil domain protein 2). [Source: Uniprot/SWISSPROT; Acc: Q8TE76] | 0.000118 | 1 | 4 |
| TRIM66 | ENST00000299550 | Tripartite motif protein 66. [Source: Uniprot/SWISSPROT; Acc: O15016] | 0.000147 | 1 | 4 |
| NP_597709.1 | ENST00000331131 | RAVER1 [Source: RefSeq_peptide; Acc: NP_597709] | 0.000164 | 1 | 5 |
| ZFP36L1 | ENST00000336440 | Butyrate response factor 1 (TIS11B protein) (EGF-response factor 1) (ERF-1). [Source: Uniprot/SWISSPROT; Acc: Q07352] | 0.000169 | 1 | 5 |
| U334_HUMAN | ENST00000258258 | Probable UPF0334 kinase-like protein. [Source: Uniprot/SWISSPROT; Acc: Q9BSD7] | 0.000183 | 1 | 7 |
| EHF | ENST00000257831 | ets homologous factor [Source: RefSeq_peptide; Acc: NP_036285] | 0.000204 | 2 | 7 |
| HMGB2 | ENST00000296503 | High mobility group protein 2 (HMG-2). [Source: Uniprot/SWISSPROT; Acc: P26583] | 0.000243 | 1 | 6 |
| CDKN2D | ENST00000250245 | Cyclin-dependent kinase 4 inhibitor D (p19-INK4d). [Source: Uniprot/SWISSPROT; Acc: P55273] | 0.000263 | 1 | 5 |
| CLDN5 | ENST00000329916 | Claudin-5 (Transmembrane protein deleted in VCFS) (TMDVCF). [Source: Uniprot/SWISSPROT; Acc: O00501] | 0.000408 | 1 | 3 |

TABLE IX-continued

| Gene Name | Transcript id | Description | P value | Total Sites | No. Cons Spec |
|---|---|---|---|---|---|
| EHHADH | ENST00000231887 | Peroxisomal bifunctional enzyme (PBE) (PBFE) [Includes: Enoyl-CoA hydratase (EC 4.2.1.17); 3,2-trans-enoyl-CoA isomerase (EC 5.3.3.8); 3-hydroxyacyl-CoA dehydrogenase (EC 1.1.1.35)]. [Source: Uniprot/SWISSPROT; Acc: Q08426] | 0.000425 | 1 | 5 |
| NP_115965.1 | ENST00000253320 | lipopolysaccharide-specific response 5-like protein [Source: RefSeq_peptide; Acc: NP_115965] | 0.000453 | 2 | 1 |
| UPF3A | ENST00000302685 | Regulator of nonsense transcripts 3A (Nonsense mRNA reducing factor 3A) (Up-frameshift suppressor 3 homolog A) (hUpf3). [Source: Uniprot/SWISSPROT; Acc: Q9H1J1] | 0.000455 | 1 | 4 |
| MSH4 | ENST00000263187 | MutS protein homolog 4. [Source: Uniprot/SWISSPROT; Acc: O15457] | 0.000461 | 1 | 5 |
| DPH5_HUMAN | ENST00000251159 | Probable diphthine synthase (EC 2.1.1.98) (Diphthamide biosynthesis methyltransferase). [Source: Uniprot/SWISSPROT; Acc: Q9H2P9] | 0.000467 | 1 | 6 |
| TPK1 | ENST00000360057 | Thiamin pyrophosphokinase 1 (EC 2.7.6.2) (Thiamine pyrophosphokinase 1) (hTPK1) (Placental protein 20) (PP20). [Source: Uniprot/SWISSPROT; Acc: Q9H3S4] | 0.000507 | 1 | 4 |
| NP_079217.1 | ENST00000231526 | hypothetical protein LOC321203 [Source: RefSeq_peptide; Acc: NP_955832] hypothetical protein LOC321203 [Source: RefSeq_peptide; Acc: NP_955832] BY ORTHOLOGY TO: ENSDART00000046274 | 0.000514 | 1 | 4 |
| NP_065108.1 | ENST00000179259 | PREDICTED: similar to chromosome 12 open reading frame 5 [Source: RefSeq_peptide_predicted; Acc: XP_417232] PREDICTED: similar to chromosome 12 open reading frame 5 [Source: RefSeq_peptide_predicted; Acc: XP_417232] BY ORTHOLOGY TO: ENSGALT00000027940 | 0.000517 | 2 | 3 |
| NP_699185.1 | ENST00000296595 | RIKEN cDNA 2810446P07 gene (2810446P07Rik), mRNA [Source: RefSeq_dna; Acc: NM_175187] RIKEN cDNA 2810446P07 gene (2810446P07Rik), mRNA [Source: RefSeq_dna; Acc: NM_175187] BY ORTHOLOGY TO: ENSMUST00000057495 | 0.00052 | 1 | 5 |
| NP_068753.2 | ENST00000336854 | CG7053-PA [Source: RefSeq_peptide; Acc: NP_573326] CG7053-PA [Source: RefSeq_peptide; Acc: NP_573326] BY ORTHOLOGY TO: CG7053-RA | 0.000525 | 1 | 4 |
| CCT6A | ENST00000275603 | T-complex protein 1, zeta subunit (TCP-1-zeta) (CCT-zeta) (CCT-zeta-1) (Tcp20) (HTR3) (Acute morphine dependence related protein 2). [Source: Uniprot/SWISSPROT; Acc: P40227] | 0.00053 | 1 | 4 |

TABLE IX-continued

| Gene Name | Transcript id | Description | P value | Total Sites | No. Cons Spec |
|---|---|---|---|---|---|
| NP_057538.1 | ENST00000267750 | Hypothetical ORF. [Source: *Saccharomyces* Genome Database; Acc: S000003200] Hypothetical ORF. [Source: Saccharomyces Genome Database; Acc: S000003200] BY ORTHOLOGY TO: YGL231C | 0.000572 | 1 | 5 |
| NP_115678.1 | ENST00000288607 | PREDICTED: similar to RIKEN cDNA 1810042K04 [Source: RefSeq_peptide_predicted; Acc: XP_213716] PREDICTED: similar to RIKEN cDNA 1810042K04 [Source: RefSeq_peptide_predicted; Acc: XP_213716] BY ORTHOLOGY TO: ENSRNOT00000001716 | 0.000591 | 1 | 5 |
| K0889_HUMAN | ENST00000279034 | PREDICTED: similar to FLJ44670 protein [Source: RefSeq_peptide; Acc: XP_542984] PREDICTED: similar to FLJ44670 protein [Source: RefSeq_peptide; Acc: XP_542984] BY ORTHOLOGY TO: ENSCAFT00000013710 | 0.000603 | 1 | 3 |
| NP_937794.1 | ENST00000341723 | expressed sequence AI987662 [Source: MarkerSymbol; Acc: MGI: 2141520] expressed sequence AI987662 [Source: MarkerSymbol; Acc: MGI: 2141520] BY ORTHOLOGY TO: ENSMUST00000049985 | 0.000616 | 1 | 5 |
| AEBP2 | ENST00000266508 | AE binding protein 2 [Source: RefSeq_peptide; Acc: NP_694939] | 0.00062 | 1 | 6 |
| YWHAE | ENST00000264335 | 14-3-3 protein epsilon (14-3-3E). [Source: Uniprot/SWISSPROT; Acc: P62258] | 0.000646 | 1 | 10 |
| NP_659416.1 | ENST00000281722 | PREDICTED: similar to hypothetical protein MGC27016 [Source: RefSeq_peptide_predicted; Acc: XP_227311] PREDICTED: similar to hypothetical protein MGC27016 [Source: RefSeq_peptide_predicted; Acc: XP_227311] BY ORTHOLOGY TO: ENSRNOT00000035846 | 0.000659 | 1 | 5 |
| NP_060818.3 | ENST00000338099 | PREDICTED: similar to FLJ11171 protein [Source: RefSeq_peptide_predicted; Acc: XP_425111] PREDICTED: similar to FLJ11171 protein [Source: RefSeq_peptide_predicted; Acc: XP_425111] BY ORTHOLOGY TO: ENSGALT00000003716 | 0.000668 | 1 | 4 |
| PACE1_HUMAN | ENST00000328079 | Protein-associating with the carboxyl-terminal domain of ezrin (Ezrin-binding protein PACE-1) (SCY1-like protein 3). [Source: Uniprot/SWISSPROT; Acc: Q8IZE3] | 0.000669 | 1 | 7 |
| HPN | ENST00000337077 | Serine protease hepsin (EC 3.4.21.—) (Transmembrane protease, serine 1) [Contains: Serine protease hepsin non-catalytic chain; Serine protease hepsin catalytic chain]. [Source: Uniprot/SWISSPROT; Acc: P05981] | 0.000683 | 1 | 5 |

TABLE IX-continued

| Gene Name | Transcript id | Description | P value | Total Sites | No. Cons Spec |
|---|---|---|---|---|---|
| CAP1 | ENST00000340450 | Adenylyl cyclase-associated protein 1 (CAP 1). [Source: Uniprot/SWISSPROT; Acc: Q01518] | 0.00069 | 1 | 5 |
| MYO3A | ENST00000265944 | Myosin IIIA (EC 2.7.1.37). [Source: Uniprot/SWISSPROT; Acc: Q8NEV4] | 0.000701 | 1 | 4 |
| DUSP8 | ENST00000331588 | Dual specificity protein phosphatase 8 (EC 3.1.3.48) (EC 3.1.3.16) (Dual specificity protein phosphatase hVH-5). [Source: Uniprot/SWISSPROT; Acc: Q13202] | 0.000705 | 1 | 7 |
| SPBC25 | ENST00000282074 | spindle pole body component 25 [Source: RefSeq_peptide; Acc: NP_065726] | 0.000709 | 2 | 3 |
| NP_116218.1 | ENST00000358906 | PREDICTED: similar to hypothetical protein FLJ14721 [Source: RefSeq_peptide_predicted; Acc: XP_573412] PREDICTED: similar to hypothetical protein FLJ14721 [Source: RefSeq_peptide_predicted; Acc: XP_573412] BY ORTHOLOGY TO: ENSRNOT00000001588 | 0.000712 | 1 | 5 |
| NP_055764.2 | ENST00000255016 | RIKEN cDNA 2810403A07 gene (2810403A07Rik), mRNA [Source: RefSeq_dna; Acc: NM_028814] RIKEN cDNA 2810403A07 gene (2810403A07Rik), mRNA [Source: RefSeq_dna; Acc: NM_028814] BY ORTHOLOGY TO: ENSMUST00000029696 | 0.000718 | 1 | 5 |
| ZFP64 | ENST00000216923 | Zinc finger protein 64, isoforms 3 and 4 (Zinc finger protein 338). [Source: Uniprot/SWISSPROT; Acc: Q9NTW7] | 0.000745 | 1 | 4 |
| ZBTB37 | ENST00000327714 | Zinc finger and BTB domain containing protein 37. [Source: Uniprot/SWISSPROT; Acc: Q5TC79] | 0.00079 | 1 | 4 |
| NP_004984.2 | ENST00000359819 | ataxin 3 isoform 1 [Source: RefSeq_peptide; Acc: NP_004984] | 0.000796 | 2 | 6 |
| SMS | ENST00000362081 | Spermine synthase (EC 2.5.1.22) (Spermidine aminopropyltransferase) (SPMSY). [Source: Uniprot/SWISSPROT; Acc: P52788] | 0.000798 | 1 | 7 |
| MAML1 | ENST00000292599 | Mastermind-like protein 1 (Mam-1). [Source: Uniprot/SWISSPROT; Acc: Q92585] | 0.000799 | 1 | 3 |
| EDG3 | ENST00000358157 | Sphingosine 1-phosphate receptor Edg-3 (S1P receptor Edg-3) (Endothelial differentiation G-protein coupled receptor 3) (Sphingosine 1-phosphate receptor 3) (S1P3). [Source: Uniprot/SWISSPROT; Acc: Q99500] | 0.000808 | 1 | 4 |
| TESK2 | ENST00000165317 | Dual specificity testis-specific protein kinase 2 (EC 2.7.1.37) (EC 2.7.1.112) (Testicular protein kinase 2). [Source: Uniprot/SWISSPROT; Acc: Q96S53] | 0.00081 | 1 | 5 |
| BTBD2 | ENST00000255608 | BTB/POZ domain containing protein 2 [Source: Uniprot/SWISSPROT; Acc: Q9BX70] | 0.000854 | 1 | 6 |

TABLE IX-continued

| Gene Name | Transcript id | Description | P value | Total Sites | No. Cons Spec |
|---|---|---|---|---|---|
| NP_076416.1 | ENST00000285689 | PREDICTED: similar to HCV NS3-transactivated protein 2 [Source: RefSeq_peptide; Acc: XP_531891] PREDICTED: similar to HCV NS3-transactivated protein 2 [Source: RefSeq_peptide; Acc: XP_531891] BY ORTHOLOGY TO: ENSCAFT00000000901 | 0.000865 | 1 | 4 |
| Q5VWN5_HUMAN | ENST00000263123 | C10orf18 protein (Fragment). [Source: Uniprot/SPTREMBL; Acc: Q6IPC8] | 0.00068 | 2 | 1 |
| DBT | ENST00000260559 | Lipoamide acyltransferase component of branched-chain alpha-keto acid dehydrogenase complex, mitochondrial precursor (EC 2.3.1.168) (Dihydrolipoyllysine-residue (2-methylpropanoyl)transferase) (E2) (Dihydrolipoamide branched chain transacylase) (BCKAD E2) [Source: Uniprot/SWISSPROT; Acc: P11162] | 0.000885 | 1 | 7 |
| EDAR | ENST00000258443 | Tumour necrosis factor receptor superfamily member EDAR precursor (Anhidrotic ectodysplasin receptor 1) (Ectodysplasin-A receptor) (EDA-A1 receptor) (Ectodermal dysplasia receptor) (Downless homolog). [Source: Uniprot/SWISSPROT; Acc: Q9UNE0] | 0.000886 | 1 | 4 |
| CTHRC1 | ENST00000330295 | Collagen triple helix repeat-containing protein 1 precursor (NMTC1 protein). [Source: Uniprot/SWISSPROT; Acc: Q96CG8] | 0.000925 | 1 | 5 |
| ZBT40_HUMAN | ENST00000315432 | Zinc finger and BTB domain containing protein 40. [Source: Uniprot/SWISSPROT; Acc: Q9NUA8] | 0.000952 | 1 | 5 |
| NP_443089.2 | ENST00000361952 | coiled-coil domain containing 16 [Source: RefSeq_peptide; Acc: NP_443089] | 0.000964 | 1 | 5 |
| POU3F2 | ENST00000328345 | POU domain, class 3, transcription factor 2 (Nervous-system specific octamer-binding transcription factor N-Oct-3) (Brain-specific homeobox/POU domain protein 2) (Brain-2) (Brn-2 protein). [Source: Uniprot/SWISSPROT; Acc: P20265] | 0.000974 | 1 | 4 |
| PHF5A | ENST00000216252 | PHD finger-like domain protein 5A (Splicing factor 3B associated 14 kDa protein) (SF3b14b). [Source: Uniprot/SWISSPROT; Acc: Q7RTV0] | 0.000986 | 1 | 4 |
| NP_115554.1 | ENST00000263997 | solute carrier family 7, member 6 opposite strand [Source: RefSeq_peptide; Acc: NP_115554] | 0.001062 | 1 | 4 |
| SLC38A4 | ENST00000266579 | solute carrier family 38, member 4 [Source: RefSeq_peptide; Acc: NP_060488] | 0.001065 | 1 | 4 |
| MTM1 | ENST00000306167 | Myotubularin (EC 3.1.3.48). [Source: Uniprot/SWISSPROT; Acc: Q13496] | 0.001094 | 1 | 4 |
| CDKN2B | ENST00000276925 | Cyclin-dependent kinase 4 inhibitor B (p14-INK4b) (p15-INK4b) (Multiple tumour suppressor 2) (MTS2). [Source: Uniprot/SWISSPROT; Acc: P42772] | 0.001131 | 2 | 4 |

TABLE IX-continued

| Gene Name | Transcript id | Description | P value | Total Sites | No. Cons Spec |
|---|---|---|---|---|---|
| MIF | ENST00000215754 | Macrophage migration inhibitory factor (MIF) (Phenylpyruvate tautomerase) (EC 5.3.2.1) (Glycosylation-inhibiting factor) (GIF). [Source: Uniprot/SWISSPROT; Acc: P14174] | 0.00115 | 1 | 3 |
| ZCCHC8 | ENST00000336229 | Zinc finger CCHC domain containing protein 8. [Source: Uniprot/SWISSPROT; Acc: Q6NZY4] | 0.001197 | 2 | 6 |
| ANKRD27 | ENST00000306065 | ankyrin repeat domain 27 (VPS9 domain) [Source: RefSeq_peptide; Acc: NP_115515] | 0.001244 | 1 | 7 |
| OAT | ENST00000224242 | Ornithine aminotransferase, mitochondrial precursor (EC 2.6.1.13) (Ornithine-oxo-acid aminotransferase) [Contains: Ornithine aminotransferase, hepatic form; Ornithine aminotransferase, renal form]. [Source: Uniprot/SWISSPROT; Acc: P04181] | 0.001252 | 1 | 4 |
| RNF13 | ENST00000344229 | RING finger protein 13. [Source: Uniprot/SWISSPROT; Acc: O43567] | 0.001254 | 2 | 7 |
| TPIS_HUMAN | ENST00000229270 | Triosephosphate isomerase (EC 5.3.1.1) (TIM) (Triose-phosphate isomerase). [Source: Uniprot/SWISSPROT; Acc: P60174] | 0.001261 | 2 | 5 |
| CTNNB1 | ENST00000349496 | Beta-catenin. [Source: Uniprot/SWISSPROT; Acc: P35222] | 0.001303 | 1 | 10 |
| CX041_HUMAN | ENST00000161782 | Protein CXorf41 (Sarcoma antigen NY-SAR-97). [Source: Uniprot/SWISSPROT; Acc: Q9NQM4] | 0.001385 | 1 | 4 |
| BUB1B | ENST00000287598 | Mitotic checkpoint serine/threonine-protein kinase BUB1 beta (EC 2.7.1.37) (hBUBR1) (MAD3/BUB1-related protein kinase) (Mitotic checkpoint kinase MAD3L) (SSK1). [Source: Uniprot/SWISSPROT; Acc: O60566] | 0.001399 | 2 | 5 |
| OSR1 | ENST00000272223 | odd-skipped related 1 [Source: RefSeq_peptide; Acc: NP_660303] | 0.001413 | 1 | 6 |
| GPR88 | ENST00000318647 | Probable G-protein coupled receptor 88 (Striatum-specific G-protein coupled receptor). [Source: Uniprot/SWISSPROT; Acc: Q9GZN0] | 0.001437 | 1 | 4 |
| CCNB3 | ENST00000276014 | G2/mitotic-specific cyclin B3. [Source: Uniprot/SWISSPROT; Acc: Q8WWL7] | 0.001489 | 1 | 5 |
| PYGM | ENST00000164139 | Glycogen phosphorylase, muscle form (EC 2.4.1.1) (Myophosphorylase). [Source: Uniprot/SWISSPROT; Acc: P11217] | 0.001511 | 1 | 5 |
| BNIP2 | ENST00000267859 | BCL2/adenovirus E18 19-kDa protein-interacting protein 2. [Source: Uniprot/SWISSPROT; Acc: Q12982] | 0.001591 | 1 | 6 |
| YAP1 | ENST00000282441 | 65 kDa Yes-associated protein (YAP65). [Source: Uniprot/SWISSPROT; Acc: P46937] | 0.001635 | 1 | 5 |

TABLE IX-continued

| Gene Name | Transcript id | Description | P value | Total Sites | No. Cons Spec |
|---|---|---|---|---|---|
| NP_079001.2 | ENST00000278520 | Adult male tongue cDNA, RIKEN full-length enriched library, clone: 2310043N13 product: weakly similar to HT025 (9 days embryo whole body cDNA, RIKEN full-length enriched library, clone: D030052K04 product: weakly similar to HT025). [Source: Uniprot/SPTREMBL; Acc: Q9D6Z7] Adult male tongue cDNA, RIKEN full-length enriched library, clone: 2310043N13 product: weakly similar to HT025 (9 days embryo whole body cDNA, RIKEN full-length enriched library, clone: D030052K04 product: weakly similar to HT025). [Source: Uniprot/SPTREMBL; Acc: Q9D6Z7] BY ORTHOLOGY TO: ENSMUST00000067578 | 0.001669 | 1 | 4 |
| NP_065988.1 | ENST00000267430 | Fanconi anemia, complementation group M [Source: RefSeq_peptide; Acc: NP_065988] | 0.001692 | 2 | 2 |
| MIDN | ENST00000300952 | midnolin [Source: RefSeq_peptide; Acc: NP_796375] | 0.001695 | 1 | 4 |
| NP_963840.2 | ENST00000287899 | similar to NADH-cytochrome b5 reductase [Source: RefSeq_peptide; Acc: XP_396073] similar to NADH-cytochrome b5 reductase [Source: RefSeq_peptide; Acc: XP_396073] BY ORTHOLOGY TO: ENSAPMT00000013057 | 0.001761 | 1 | 5 |
| NXPH1 | ENST00000265579 | Neurexophilin-1 precursor, [Source: Uniprot/SWISSPROT; Acc: P548417] | 0.001878 | 2 | 6 |
| ZIC2 | ENST00000245295 | Zinc finger protein ZIC 2 (Zinc finger protein of the cerebellum 2). [Source: Uniprot/SWISSPROT; Acc: O95409] | 0.001906 | 1 | 6 |
| ERMAP | ENST00000328249 | erythroblast membrane-associated protein [Source: RefSeq_peptide; Acc: NP_001017922] | 0.001966 | 2 | 1 |
| IRX4 | ENST00000231357 | Iroquois-class homeodomain protein IRX-4 (Iroquois homeobox protein 4) (Homeodomain protein IRXA3). [Source: Uniprot/SWISSPROT; Acc: P78413] | 0.002018 | 1 | 3 |
| PNOC | ENST00000301908 | Nociceptin precursor [Contains: Neuropeptide 1; Nociceptin (Orphanin FQ) (PPNOC); Neuropeptide 2]. [Source: Uniprot/SWISSPROT; Acc: Q13519] | 0.002057 | 1 | 4 |
| ZNF583 | ENST00000291598 | zinc finger protein 583 [Source: RefSeq_peptide; Acc: NP_689691] | 0.00212 | 1 | 4 |
| CCND1 | ENST00000227507 | G1/S-specific cyclin D1 (PRAD1 oncogene) (BCL-1 oncogene). [Source: Uniprot/SWISSPROT; Acc: P24385] | 0.002183 | 1 | 4 |
| NP_116316.1 | ENST00000254742 | RIKEN cDNA 2810021O14 gene (2810021O14Rik), mRNA [Source: RefSeq_dna; Acc: NM_025480] RIKEN cDNA 2810021O14 gene (2810021O14Rik), mRNA [Source: RefSeq_dna; Acc: NM_025480] BY ORTHOLOGY TO: ENSMUST00000087511 | 0.002194 | 2 | 5 |

TABLE IX-continued

| Gene Name | Transcript id | Description | P value | Total Sites | No. Cons Spec |
|---|---|---|---|---|---|
| RNF125 | ENST00000217740 | RING finger protein 125 (EC 6.3.2.—) (T-cell RING activation protein 1) (TRAC-1). [Source: Uniprot/SWISSPROT; Acc: Q96EQ8] | 0.002203 | 1 | 4 |
| TRPC6 | ENST00000344327 | Short transient receptor potential channel 6 (TrpC6). [Source: Uniprot/SWISSPROT; Acc: Q9Y210] | 0.002295 | 1 | 4 |
| NPEPPS | ENST00000322157 | Puromycin-sensitive aminopeptidase (EC 3.4.11.—) (PSA). [Source: Uniprot/SWISSPROT; Acc: P55786] | 0.002348 | 1 | 8 |
| Q9ULK9_HUMAN | ENST00000264229 | PREDICTED: similar to Nucleolar phosphoprotein p130 (Nucleolar 130 kDa protein) (140 kDa nucleolar phosphoprotein) (Nopp140) (Nucleolar and coiled-body phosphoprotein 1) [Source: RefSeq_peptide_predicted; Acc: XP_214022] PREDICTED: similar to Nucleolar phosphoprotein p130 (Nucleolar 130 kDa protein) (140 kDa nucleolar phosphoprotein) (Nopp140) (Nucleolar and coiled-body phosphoprotein 1) [Source: RefSeq_peptide_predicted; Acc: XP_214022] BY ORTHOLOGY TO: ENSRNOT00000002908 | 0.002364 | 1 | 4 |
| GFRA2 | ENST00000306793 | GDNF family receptor alpha 2 precursor (GFR-alpha 2) (Neurturin receptor alpha) (NTNR-alpha) (NRTNR-alpha) (TGF-beta-related neurotrophic factor receptor 2) (GDNF receptor beta) (GDNFR-beta) (RET ligand 2). [Source: Uniprot/SWISSPROT; Acc: O00451] | 0.002495 | 1 | 6 |
| MTHFD2 | ENST00000264090 | Bifunctional methylenetetrahydrofolate dehydrogenase/cyclohydrolase, mitochondrial precurcor [Includes: NAD-dependent methylenetetrahydrofolate dehydrogenase (EC 1.5.1.15); Methenyltetrahydrofolate cyclohydrolase (EC 3.5.4.9)]. [Source: Uniprot/SWISSPROT; Acc: P13995] | 0.002509 | 1 | 5 |
| TEAD2 | ENST00000311227 | Transcriptional enhancer factor TEF-4 (TEA domain family member 2) (TEAD-2). [Source: Uniprot/SWISSPROT; Acc: Q15562] | 0.002529 | 1 | 3 |
| YT521_HUMAN | ENST00000355665 | Putative splicing factor YT521. [Source: Uniprot/SWISSPROT; Acc: Q96MU7] | 0.002572 | 2 | 1 |
| TBX1 | ENST00000332710 | T-box transcription factor TBX1 (T-box protein 1) (Testis-specific T-box protein). [Source: Uniprot/SWISSPROT; Acc: O43435] | 0.002675 | 1 | 6 |
| Q86X61_HUMAN | ENST00000334227 | OVOS2 protein. [Source: Uniprot/SPTREMBL; Acc: Q86X61] | 0.00268 | 2 | 2 |
| EVL | ENST00000355449 | Ena/vasodilator stimulated phosphoprotein-like protein (Ena/VASP-like protein). [Source: Uniprot/SWISSPROT; Acc: Q9UI08] | 0.00269 | 2 | 3 |

TABLE IX-continued

| Gene Name | Transcript id | Description | P value | Total Sites | No. Cons Spec |
|---|---|---|---|---|---|
| EWSR1 | ENST00000332050 | RNA-binding protein EWS (EWS oncogene) (Ewing sarcoma breakpoint region 1 protein). [Source: Uniprot/SWISSPROT; Acc: Q01844] | 0.002703 | 2 | 1 |
| MMRN2 | ENST00000310615 | Multimerin 2 precursor (EMILIN-3) (Elastin microfibril interface located protein 3) (Elastin microfibril interfacer 3) (EndoGlyx-1 p125/p140 subunit). [Source: Uniprot/SWISSPROT; Acc: Q9H8L6] | 0.002759 | 1 | 4 |
| FNTA | ENST00000302279 | Protein farnesyltransferase/geranylgeranyltransferase type I alpha subunit (EC 2.5.1.58) (EC 2.5.1.59) (CAAX farnesyltransferase alpha subunit) (Ras proteins prenyltransferase alpha) (FTase-alpha) (Type I protein geranyl-geranyltansferase alpha subunit) [Source: Uniprot/SWISSPROT; Acc: P49354] | 0.002813 | 1 | 6 |
| OMD | ENST00000247535 | Osteomodulin precursor (Osteoadherin) (OSAD) (Keratan sulfate proteoglycan osteomodulin) (KSPG osteomodulin). [Source: Uniprot/SWISSPROT; Acc: Q99983] | 0.002819 | 1 | 3 |
| ZNF654 | ENST00000309495 | zinc finger protein 654 [Source: RefSeq_peptide; Acc: NP_060763] | 0.002862 | 2 | 3 |
| ING3 | ENST00000315883 | Inhibitor of growth protein 3 (p47ING3 protein). [Source: Uniprot/SWISSPROT; Acc: Q9NXR8] | 0.003065 | 2 | 1 |
| Q9UHS9_HUMAN | ENST00000357012 | NOT ANNOTATED | 0.003127 | 2 | 2 |
| DRG2 | ENST00000225729 | Developmentally regulated GTP-binding protein 2 (DRG 2). [Source: Uniprot/SWISSPROT; Acc: P55039] | 0.003145 | 1 | 4 |
| NP_116203.1 | ENST00000257575 | Putative protein, with at least 4 transmembrane domains, of bilaterial origin (38.9 kD) (XB497) [Source:; Acc: Cel.9253] Putative protein, with at least 4 transmembrane domains, of bilaterial origin (38.9 kD) (XB497) [Source:; Acc: Cel.9253] BY ORTHOLOGY TO: ZC13.1b | 0.003156 | 1 | 4 |
| NP_849149.2 | ENST00000324698 | RIKEN cDNA 4932408B21 gene (4932408B21Rik), mRNA [Source: RefSeq_dna; Acc: NM_172535] RIKEN cDNA 4932408B21 gene (4932408B21 Rik), mRNA [Source: RefSeq_dna; Acc: NM_172535] BY ORTHOLOGY TO: ENSMUST00000052277 | 0.003163 | 1 | 4 |
| GPR85 | ENST00000297146 | Probable G-protein coupled receptor 85 (Super conserved receptor expressed in brain 2). [Source: Uniprot/SWISSPROT; Acc: P60893] | 0.003165 | 1 | 6 |
|  | ENST00000266432 | NOT ANNOTATED | 0.003275 | 2 | 1 |
| SDFR1 | ENST00000345330 | stromal cell derived factor receptor 1 isoform a [Source: RefSeq_peptide; Acc: NP_059429] | 0.003289 | 1 | 9 |
| ARMC4 | ENST00000239715 | armadillo repeat containing 4 [Source: RefSeq_peptide; Acc: NP_060546] | 0.003311 | 2 | 1 |

TABLE IX-continued

| Gene Name | Transcript id | Description | P value | Total Sites | No. Cons Spec |
|---|---|---|---|---|---|
| ATF2 | ENST00000295499 | Cyclic-AMP-dependent transcription factor ATF-2 (Activating transcription factor 2) (cAMP response element binding protein CRE-BP1) (HB16). [Source: Uniprot/SWISSPROT; Acc: P15336] | 0.003334 | 2 | 1 |
| Q9P0E8_HUMAN | ENST00000330598 | NOT ANNOTATED | 0.00338 | 2 | 1 |
| PANX1 | ENST00000227638 | Pannexin-1. [Source: Uniprot/SWISSPROT; Acc: Q96RD7] | 0.003393 | 2 | 5 |
| XP_068632.2 | ENST00000274299 | PREDICTED: hypothetical protein XP_068632 [Source: RefSeq_peptide_predicted; Acc: XP_068632] | 0.003394 | 1 | 3 |
| GALK2 | ENST00000327171 | N-acetylgalactosamine kinase (EC 2.7.1.—) (GalNAc kinase) (Galactokinase 2). [Source: Uniprot/SWISSPROT; Acc: Q01415] | 0.003406 | 2 | 5 |
| NP_071903.2 | ENST00000347571 | limb region 1 protein [Source: RefSeq_peptide; Acc: NP_071903] | 0.003545 | 2 | 1 |
| NP_061961.2 | ENST00000221265 | Paf1, RNA polymerase II associated factor, homolog [Source: RefSeq_peptide; Acc: NP_061961] | 0.003601 | 1 | 4 |
| EVG1_HUMAN | ENST00000249079 | Hypothetical UPF0193 protein EVG1 homolog. [Source: Uniprot/SWISSPROT; Acc: Q9VSS7] Hypothetical UPF0193 protein EVG1 homolog. [Source: Uniprot/SWISSPROT; Acc: Q9VSS7] BY ORTHOLOGY TO: CG5280-RA | 0.003609 | 2 | 5 |
| GMPR | ENST00000259727 | GMP reductase 1 (EC 1.7.1.7) (Guanosine 5'-monophosphate oxidoreductase 1) (Guanosine monophosphate reductase 1). [Source: Uniprot/SWISSPROT; Acc: P36959] | 0.003624 | 1 | 4 |
| CBR1 | ENST00000290349 | Carbonyl reductase [NADPH] 1 (EC 1.1.1.184) (NADPH-dependent carbonyl reductase 1) (Prostaglandin-E(2) 9-reductase) (EC 1.1.1.189) (Prostaglandin 9-ketoreductase) (15-hydroxyprostaglandin dehydrogenase [NADP+]) (EC 1.1.1.197). [Source: Uniprot/SWISSPROT; Acc: P16152] | 0.003639 | 1 | 3 |
| F10C1_HUMAN | ENST00000277884 | Protein FRA10AC1. [Source: Uniprot/SWISSPROT; Acc: Q70Z53] | 0.003645 | 2 | 3 |
| FAM13C1 | ENST00000277705 | Protein FAM13C1. [Source: Uniprot/SWISSPROT; Acc: Q8NE31] | 0.003648 | 1 | 4 |
| EPB41L5 | ENST00000331393 | Band 4.1-like protein 5. [Source: Uniprot/SWISSPROT; Acc: Q9HCM4] | 0.00369 | 2 | 1 |
| IL5 | ENST00000231454 | Interleukin-5 precursor (IL-5) (T-cell replacing factor) (TRF) (Eosinophil differentiation factor) (B cell differentiation factor I). [Source: Uniprot/SWISSPROT; Acc: P05113] | 0.003712 | 1 | 4 |
| NP_115676.1 | ENST00000312777 | trichoplein [Source: RefSeq_peptide; Acc: NP_115676] | 0.003739 | 1 | 4 |

TABLE IX-continued

| Gene Name | Transcript id | Description | P value | Total Sites | No. Cons Spec |
|---|---|---|---|---|---|
| NP_660308.1 | ENST00000296824 | RIKEN cDNA 0610011N22 gene (0610011N22Rik), mRNA [Source: RefSeq_dna; Acc: NM_024201] RIKEN cDNA 0610011N22 gene (0610011N22Rik), mRNA [Source: RefSeq_dna; Acc: NM_024201] BY ORTHOLOGY TO: ENSMUST00000022063 | 0.003745 | 1 | 3 |
| TAS2R14 | ENST00000240689 | Taste receptor type 2 member 14 (T2R14) (Taste receptor family B member 1) (TRB1). [Source: Uniprot/SWISSPROT; Acc: Q9NYV8] | 0.003749 | 2 | 2 |
| SFRS10 | ENST00000342294 | Arginine/serine-rich splicing factor 10 (Transformer-2-beta) (HTRA2-beta) (Transformer 2 protein homolog). [Source: Uniprot/SWISSPROT; Acc: P62995] | 0.003752 | 2 | 1 |
| AKT1 | ENST00000310523 | RAC-alpha serine/threonine-protein kinase (EC 2.7.1.37) (RAC-PK-alpha) (Protein kinase B) (PKB) (C-AKT). [Source: Uniprot/SWISSPROT; Acc: P31749] | 0.003758 | 1 | 4 |
| WTAP | ENST00000337387 | Wilms' tumour 1-associating protein (WT1-associated protein) (Putative pre-mRNA splicing regulator female-lethal(2D) homolog). [Source: Uniprot/SWISSPROT; Acc: Q15007] | 0.003802 | 2 | 1 |
| HTATIP2 | ENST00000338653 | HIV-1 Tat interactive protein 2, 30 kDa [Source: RefSeq_peptide; Acc: NP_006401] | 0.003824 | 1 | 6 |
|  | ENST00000313360 | NOT ANNOTATED | 0.003887 | 2 | 2 |
| KLF6 | ENST00000173785 | Core promoter element-binding protein (Kruppel-like factor 6) (B-cell derived protein 1) (Proto-oncogene BCD1) (Transcription factor Zf9) (GC-rich sites binding factor GBF). [Source: Uniprot/SWISSPROT; Acc: Q99612] | 0.00389 | 1 | 5 |
| Q5VWN5_HUMAN | ENST00000328090 | C10orf18 protein (Fragment). [Source: Uniprot/SPTREMBL; Acc: Q6IPC8] | 0.003926 | 2 | 2 |
| CERK | ENST00000216264 | Ceramide kinase (EC 2.7.1.138) (Acylsphingosine kinase) (hCERK) (Lipid kinase 4) (LK4). [Source: Uniprot/SWISSPROT; Acc: Q8TCT0] | 0.00393 | 1 | 4 |
| HSPA5 | ENST00000265959 | 78 kDa glucose-regulated protein precursor (GRP 78) (Immunoglobulin heavy chain binding protein) (BiP) (Endoplasmic reticulum lumenal Ca(2+) binding protein grp78). [Source: Uniprot/SWISSPROT; Acc: P11021] | 0.003975 | 1 | 5 |
| KLHL1 | ENST00000279889 | Kelch-like protein 1. [Source: Uniprot/SWISSPROT; Acc: Q9NR64] | 0.004008 | 2 | 5 |
| RPSA | ENST00000301821 | 40S ribosomal protein SA (p40) (34/67 kDa laminin receptor) (Colon carcinoma laminin-binding protein) (NEM/1CHD4) (Multidrug resistance-associated protein MGr1-Ag). [Source: Uniprot/SWISSPROT; Acc: P08865] | 0.004055 | 1 | 3 |

TABLE IX-continued

| Gene Name | Transcript id | Description | P value | Total Sites | No. Cons Spec |
|---|---|---|---|---|---|
| TBC1D1 | ENST00000261439 | TBC1 domain family member 1. [Source: Uniprot/SWISSPROT; Acc: Q86TI0] | 0.004086 | 2 | 5 |
| GPR109A | ENST00000328880 | Probable G-protein coupled receptor 109B (G-protein coupled receptor HM74). [Source: Uniprot/SWISSPROT; Acc: P49019] | 0.00416 | 1 | 3 |
| ATN1 | ENST00000356654 | Atrophin-1 (Dentatorubral-pallidoluysian atrophy protein). [Source: Uniprot/SWISSPROT; Acc: P54259] | 0.004207 | 1 | 4 |
| O95036_HUMAN | ENST00000304230 | NOT ANNOTATED | 0.004216 | 2 | 1 |
| SLC39A8 | ENST00000265515 | solute carrier family 39 (zinc transporter), member 8 [Source: RefSeq_peptide; Acc: NP_071437] | 0.00427 | 1 | 5 |
| NP_054890.1 | ENST00000238892 | postsynaptic protein CRIPT [Source: RefSeq_peptide; Acc: NP_054890] | 0.004295 | 2 | 4 |
| CDKN2C | ENST00000262662 | Cyclin-dependent kinase 6 inhibitor (p18-INK6) (Cyclin-dependent kinase 4 inhibitor C) (p18-INK4c). [Source: Uniprot/SWISSPROT; Acc: P42773] | 0.004302 | 1 | 3 |
| NUPL1 | ENST00000306113 | Nucleoporin p58/p45 (Nucleoporin-like protein 1). [Source: Uniprot/SWISSPROT; Acc: Q9BVL2] | 0.004345 | 1 | 5 |
| CJ082_HUMAN | ENST00000356850 | NOT ANNOTATED | 0.004356 | 2 | 1 |
| ELK1 | ENST00000247161 | ETS domain protein Elk-1. [Source: Uniprot/SWISSPROT; Acc: P19419] | 0.004382 | 1 | 4 |
| CENTD3 | ENST00000239440 | Centaurin-delta 3 (Cnt-d3) (Arf-GAP, Rho-GAP, ankyrin repeat and pleckstrin homology domains-containing protein 3). [Source: Uniprot/SWISSPROT; Acc: Q8WWN8] | 0.004384 | 1 | 6 |
| NP_005109.2 | ENST00000313163 | tumour necrosis factor (ligand) superfamily, member 15 [Source: RefSeq_peptide; Acc: NP_005109] | 0.00447 | 1 | 4 |
| Q5VY36_HUMAN | ENST00000258651 | OTTHUMP00000018470. [Source: Uniprot/SPTREMBL; Acc: Q5VY36] | 0.004492 | 2 | 2 |
| CDH8 | ENST00000299345 | Cadherin-8 precursor. [Source: Uniprot/SWISSPROT; Acc: P55286] | 0.004507 | 1 | 6 |
| CD99L2 | ENST00000320893 | CD99 antigen-like 2 isoform E3'-E4'-E3-E4 [Source: RefSeq_peptide; Acc: NP_113650] | 0.004543 | 2 | 1 |
| PMP22 | ENST00000312280 | Peripheral myelin protein 22 (PMP-22). [Source: Uniprot/SWISSPROT; Acc: Q01453] | 0.004582 | 1 | 9 |
| KIAA1958 | ENST00000356558 | PREDICTED: similar to RIKEN cDNA E130308A19 [Source: RefSeq_peptide; Acc: XP_538791] PREDICTED: similar to RIKEN cDNA E130308A19 [Source: RefSeq_peptide; Acc: XP_538791] BY ORTHOLOGY TO: ENSCAFT00000004894 | 0.004632 | 1 | 7 |
| LECT1 | ENST00000258609 | Chondromodulin-I precursor (ChM-I) (Leukocyte cell-derived chemotaxin 1) [Contains: Chondrosurfactant protein (CH-SP)]. [Source: Uniprot/SWISSPROT; Acc: O75829] | 0.004669 | 1 | 7 |

TABLE IX-continued

| Gene Name | Transcript id | Description | P value | Total Sites | No. Cons Spec |
|---|---|---|---|---|---|
| NP_001003684.1 | ENST00000332801 | ubiquinol-cytochrome c reductase complex 7.2 kDa protein isoform b [Source: RefSeq_peptide; Acc: NP_001003684] | 0.004744 | 1 | 2 |
| PDXK | ENST00000291565 | Pyridoxal kinase (EC 2.7.1.35) (Pyridoxine kinase). [Source: Uniprot/SWISSPROT; Acc: O00764] | 0.004927 | 1 | 3 |
| PDC | ENST00000271587 | Phosducin (PHD) (33 kDa phototransducing protein) (MEKA protein). [Source: Uniprot/SWISSPROT; Acc: P20941] | 0.004942 | 1 | 5 |
| XPO1 | ENST00000195419 | Exportin-1 (Chromosome region maintenance 1 protein homolog). [Source: Uniprot/SWISSPROT; Acc: O14980] | 0.004947 | 1 | 7 |
| FZD5 | ENST00000295417 | Frizzled 5 precursor (Frizzled-5) (Fz-5) (hFz5) (FzE5). [Source: Uniprot/SWISSPROT; Acc: Q13467] | 0.004985 | 1 | 5 |
| Q8WV45_HUMAN | ENST00000307544 | Novel protein. [Source: Uniprot/SPTREMBL; Acc: Q5T5P3] | 0.005014 | 1 | 1 |
| NUP37 | ENST00000251074 | Nucleoporin Nup37 (p37). [Source: Uniprot/SWISSPROT; Acc: Q8NFH4] | 0.005016 | 1 | 3 |
| TAF11 | ENST00000334316 | Transcription initiation factor TFIID subunit 11 (Transcription initiation factor TFIID 28 kDa subunit) (TAF(II)28) (TAFII-28) (TAFII28) (TFIID subunit p30-beta). [Source: Uniprot/SWISSPROT; Acc: Q15544] | 0.00503 | 1 | 4 |
| APBA3 | ENST00000316757 | Amyloid beta A4 precursor protein-binding family A member 3 (Neuron-specific X11L2 protein) (Neuronal Munc18-1-interacting protein 3) (Mint-3) (Adapter protein X11gamma). [Source: Uniprot/SWISSPROT; Acc: O96018] | 0.005054 | 1 | 5 |
| NP_689672.2 | ENST00000315997 | PREDICTED: similar to MGC45438 protein [Source: RefSeq_peptide_predicted; Acc: XP_155973] PREDICTED: similar to MGC45438 protein [Source: RefSeq_peptide_predicted; Acc: XP_155973] BY ORTHOLOGY TO: ENSMUST00000050160 | 0.00519 | 1 | 5 |
| NP_065170.1 | ENST00000215906 | PREDICTED: similar to aspartyl(asparaginyl)beta-hydroxylase; HAAH [Source: RefSeq_peptide_predicted; Acc: XP_424691] PREDICTED: similar to aspartyl(asparaginyl)beta-hydroxylase; HAAH [Source: RefSeq_peptide_predicted; Acc: XP_424691] BY ORTHOLOGY TO: ENSGALT00000004159 | 0.0052 | 1 | 4 |
| Q96LP0_HUMAN | ENST00000299326 | NOT ANNOTATED | 0.005387 | 1 | 2 |
| Q9P2J0_HUMAN | ENST00000258005 | NHS-like 1 [Source: MarkerSymbol; Acc: MGI: 106390] NHS-like 1 [Source: MarkerSymbol; Acc: MGI: 106390] BY ORTHOLOGY TO: ENSMUST00000037341 | 0.005482 | 1 | 4 |

TABLE IX-continued

| Gene Name | Transcript id | Description | P value | Total Sites | No. Cons Spec |
|---|---|---|---|---|---|
| CLP24_HUMAN | ENST00000253934 | Claudin-like protein 24. [Source: Uniprot/SWISSPROT; Acc: Q9BSN7] | 0.005535 | 1 | 4 |
| SBF2 | ENST00000256190 | SET binding factor 2 [Source: RefSeq_peptide; Acc: NP_112224] | 0.005559 | 1 | 2 |
| BRP44L | ENST00000341756 | Brain protein 44-like protein. [Source: Uniprot/SWISSPROT; Acc: Q9Y5U8] | 0.005595 | 1 | 6 |
| EEF1E1 | ENST00000264871 | Eukaryotic translation elongation factor 1 epsilon-1 (Multisynthetase complex auxiliary component p18) (Elongation factor p18). [Source: Uniprot/SWISSPROT; Acc: O43324] | 0.005618 | 1 | 5 |
| NP_036404.1 | ENST00000261897 | Huntingtin interacting protein C isoform 2 [Source: RefSeq_peptide; Acc: NP_036404] | 0.005628 | 1 | 3 |
| KLRC1 | ENST00000347831 | NKG2-A/NKG2-B type II integral membrane protein (NKG2-A/B activating NK receptor) (NK cell receptor A). [Source: Uniprot/SWISSPROT; Acc: P26715] | 0.005685 | 1 | 1 |
| NP_694946.1 | ENST00000331203 | PREDICTED: similar to hypothetical protein FLJ37440 [Source: RefSeq_peptide_predicted; Acc: XP_419304] PREDICTED: similar to hypothetical protein FLJ37440 [Source: RefSeq_peptide_predicted; Acc: XP_419304] BY ORTHOLOGY TO: ENSGALT00000013441 | 0.005686 | 1 | 5 |
| KLRC1 | ENST00000359151 | NKG2-A/NKG2-B type II integral membrane protein (NKG2-A/B activating NK receptor) (NK cell receptor A). [Source: Uniprot/SWISSPROT; Acc: P26715] | 0.005697 | 1 | 2 |
| NP_997343.1 | ENST00000340819 | NOT ANNOTATED | 0.005703 | 1 | 2 |
| SUPT16H | ENST00000216297 | chromatin-specific transcription elongation factor large subunit [Source: RefSeq_peptide; Acc: NP_009123] | 0.005743 | 1 | 6 |
| MUC16 | ENST00000331986 | Ovarian cancer related tumour marker CA125. [Source: Uniprot/SPTREMBL; Acc: Q8WXI7] | 0.005825 | 1 | 2 |
| NP_689988.1 | ENST00000307588 | KM-HN-1 protein [Source: RefSeq_peptide; Acc: NP_689988] | 0.005895 | 1 | 3 |
| TRA2A_HUMAN | ENST00000297071 | Transformer-2 protein homolog (TRA-2 alpha). [Source: Uniprot/SWISSPROT; Acc: Q13595] | 0.005906 | 1 | 5 |
| NP_077001.1 | ENST00000319285 | RIKEN cDNA 2410015N17 gene (2410015N17Rik), mRNA [Source: RefSeq_dna; Acc: NM_023203] RIKEN cDNA 2410015N17 gene (2410015N17Rik), mRNA [Source: RefSeq_dna; Acc: NM_023203] BY ORTHOLOGY TO: ENSMUST00000035276 | 0.005907 | 1 | 3 |
| SFRS11 | ENST00000235399 | Splicing factor arginine/serine-rich 11 (Arginine-rich 54 kDa nuclear protein) (p54). [Source: Uniprot/SWISSPROT; Acc: Q05519] | 0.005937 | 1 | 7 |
| CALN1 | ENST00000329008 | Calneuron-1 (Calcium-binding protein CaBP8). [Source: Uniprot/SWISSPROT; Acc: Q9BXU9] | 0.00597 | 1 | 7 |

TABLE IX-continued

| Gene Name | Transcript id | Description | P value | Total Sites | No. Cons Spec |
|---|---|---|---|---|---|
| NP_078959.2 | ENST00000306049 | RIKEN cDNA 1110002N22 gene (1110002N22Rik), mRNA [Source: RefSeq_dna; Acc: NM_183275] RIKEN cDNA 1110002N22 gene (1110002N22Rik), mRNA [Source: RefSeq_dna; Acc: NM_183275] BY ORTHOLOGY TO: ENSMUST00000050207 | 0.005972 | 1 | 3 |
| ATP6V1G1 | ENST00000259415 | Vacuolar ATP synthase subunit G 1 (EC 3.6.3.14) (V-ATPase G subunit 1) (Vacuolar proton pump G subunit 1) (V-ATPase 13 kDa subunit 1) (Vacuolar ATP synthase subunit M16). [Source: Uniprot/SWISSPROT; Acc: O75348] | 0.005978 | 2 | 4 |
| DRP2 | ENST00000263029 | Dystrophin-related protein 2. [Source: Uniprot/SWISSPROT; Acc: Q13474] | 0.005999 | 1 | 3 |

Example 6

Cluster Analysis of miRNA Expression in Mouse Lung Specimens

Total RNA from mouse normal and tumor tissues was prepared using the Trizol reagent (Invitrogen, Calif.). The microarray has LNA-modified oligonucleotide probes to all annotated miRNAs from the mouse (313 miRNAs) and humans (238 miRNAs) in the miRBase MicroRNA database Release 7.1. These miRNAs are displayed in quadruplicate independent positions on each array. The arrays also contain appropriate positive and negative controls, as purchased from Exigon A/S (Copenhagen, Denmark). Each array was independently hybridized two or more times to assure results are replicated. Interpretable findings require concordant findings of four presentations of individual miRNAs. Labeled RNA was hybridized overnight at 65° C. in a hybridization mixture containing 4×SSC, 0.1% SDS, 1 µg/µl Herring Sperm DNA and 38% formamide.

Hybridized slides were washed three times in 2×SSC, 0.25% SDS at 65° C., followed by three times in 0.08×SSC, and finally three times in 0.4×SSC at room temperature. The microarrays were scanned with the ArrayWorx scanner (Applied Precision, USA) and manufacturer's procedures. Scanned images were imported into TIGR Spot Finder version 3.1 (50) for the extraction of mean spot intensities and median local background intensities excluding spots with intensities below median local background and +4× standard deviations. Background-correlated intensities were normalized using variance stabilizing normalization package version 1.8.0 (51) for R (The R Project for Statistical Computing). Intensities of replicate spots are averaged using Microsoft Excel. Probes displaying a coefficient of variance >100% are excluded from further analyses. Results are displayed in FIG. 5.

Example 7

Semi-Quantitative RT-PCR Assays

Total RNA was isolated from desired human and mouse lung tissues as above. Individual miRNA species were detected using the mirVana™ qRT-PCR miRNA detection procedure (Ambion, Tx). This procedure allows nonisotopic, sensitive, and rapid quantitation of mature microRNA (miRNA) expression levels. 25 ng of total RNA was reverse transcribed using a miR-34c specific primer including a minus reverse transcriptase control. PCR was then carried out according to the manufacturers instructions. The resulting approximately 90 bp PCR products were resolved on a 3% agarose gel and stained with GelStar nucleic acid gel stain (Cambrex, Me.).

Results are displayed in FIG. 6.

Example 8

Over-Expression of miRNAs in Murine Transgenic Lung Cancer

Comprehensive locked nucleic acid (LNA) microarray analyses were conducted to profile miRNA expression independently in malignant and normal lung tissues isolated from human surfactant protein C(SP-C) driven wild-type and proteasome-degradation resistant cyclin E transgenic lines (Ma et al). Degradation-resistant cyclin E lines had increased neoplastic lesions as compared to wild-type cyclin E lines even when cyclin E expression levels were comparable (Ma et al). Adenocarcinomas and adjacent normal lung tissues from these transgenic lines and normal lung tissues from age and sex matched non-transgenic (Tg−) FVB mice were each examined in these miRNA microarrays containing 315 murine miRNAs. FIG. 8A displays statistically significantly expression changes of the most to least over-expressed miRNAs. FIG. 8B presents the fold changes of these miRNAs relative to Tg− normal lung tissues.

These lung cancers had 114 to 4 fold higher expression levels of the highlighted miRNAs as compared to Tg− normal lung tissues. Three miRNAs with highest expression levels (>10 fold) in these lung cancers were: miR-136, miR-376a and miR-31, as shown in FIG. 8B. All three miRNAs were previously unrecognized as highlighted miRNAs in lung cancer.

Transgenic Lung Tissues

Murine cyclin E transgenic lines that exhibit pre-malignant and malignant (adenocarcinoma) lung lesions were previously described (Ma et al). Those studied here included human SP-C-driven wild-type cyclin E transgenic (line 2) and proteasome degradation-resistant (line 4) lines (18). Adenocarcinomas and adjacent histopathologically normal lung tissues were individually harvested from age and sex matched mice and immediately placed in RNAlater (Ambion, Austin, Tex.). Total RNA was isolated using established techniques for miRNA expression arrays. Formalin-fixed and paraffin-embedded transgenic lung tissues were harvested and used for ISH assays.

RNA Isolation and miRNA Arrays

The RNA isolation and miRNA array procedures were described previously (Lui et al). In brief, total RNA was isolated from cell lines and lung tissues with TRIzol reagent (Invitrogen, Carlsbad, Calif.) and was 3' end labeled using T4 RNA ligase to couple Cy3-labeled RNA linkers. Labeled RNA was hybridized to LNA microarrays overnight at 65° C. in a hybridization mixture containing 4×sodium chloride citrate (SSC) (1×SSC: 150 mM sodium chloride and 15 mM sodium citrate), 0.1% SDS, 1 µg/µl herring sperm DNA and 38% formamide. Slides were washed three times in 2 ×SSC, 0.025% SDS at 65° C., three times in 0.8×SSC and three times in 0.4×SSC at room temperature. Each RNA sample was independently hybridized twice. There were four probe sets used for each miRNA. Only concordant hybridization results were scored. Microarrays were scanned using an ArrayWorx scanner (Applied Precision, Issaquah, Wash.). Images were analyzed using GridGrinder (http COLON SLASH SLASH gridgrinder DOT sourceforge DOT net/) (Hyperlink deactivated) and background-subtracted spot intensities were normalized using variance stabilization normalization (Sempere et al). The miRNAs selected for in-depth study showed statistically significant expression differences in both murine and human normal versus malignant lung tissues.

Validation using ISH Assays

To independently validate and to determine spatial distribution patterns of specific miRNAs, ISH assays were used. As shown in FIG. 9, malignant (adenocarcinoma) and adjacent normal lung tissues were studied in transgenic cyclin E mice. Histopathologic analyses of lung tissues were performed to identify normal and malignant lung tissues. Expression profiles of miR-31 (the functionally highlighted miRNA), miR-21 and control 18S rRNA were each analyzed by ISH in malignant and normal lung tissues from transgenic mice. As displayed, miR-31 exhibited reduced minimal expression in normal lung tissue, but high miR-31 expression was detected within malignant lung tissue. Concordant results were observed in human paired normal-malignant lung tissues, as in FIG. 9. Low levels of miR-31 expression whereas found in normal human lung tissue, but a high expression level was present in malignant lung tissue. As anticipated from prior work miR-21 was also detected in FIG. 9 at higher expression levels in malignant than in normal human lung tissue. The 18S rRNA signal was ubiquitously expressed in both normal and malignant lung tissues, confirming integrity of RNA used in these tissue analyses. Together, these results confirm expression patterns of specific miRNAs in malignant versus normal lung tissues.

In Situ Hybridization Assays

ISH assays were performed according to standard procedures as described in Example 8B) above. In brief, slides were prehybridized in hybridization solution (50% formamide, 5% SSC, 500 µg/mL yeast tRNA, and 1% Denhardt's solution) at 50° C. for 30 min. Ten pmol of the desired FITC-labeled, LNA-modified DNA probes (Integrated DNA Technologies, Coralville, Iowa) complementary to specific miRNAs and/or biotinylated unmodified DNA probes against 18S rRNA were added and hybridized for 2 hours at a temperature 20° C. to 25° C. below the calculated melting temperature of the LNA probe. After stringent washes, a tyramide signal amplification (TSA) reaction was carried out using the GenPoint Fluorescein kit (DakoCytomation, Glostrup, Denmark) and the manufacturer's recommended procedures and with the substitution of streptavidin/HRP (Invitrogen, Carlsbad, Calif.) for detection of biotinylated probes. A standard immunohistochemistry protocol was used to detect cytokeratin 19 (CK19 1:200 dilution; Biogenex, San Ramon, Calif.) and revealed by TSA with secondary anti-mouse/HRP (1:500 dilution; Biorad, Hercules, Calif.). Slides were mounted with Prolong Gold solution (Invitrogen).

Validation Using Real-Time RT-PCR

To independently validate these highlighted miRNAs, real-time RT-PCR assays were conducted using total RNA isolated from pulmonary adenocarcinomas and adjacent normal lung tissues from the described murine transgenic lines. As shown, miR-136, miR-376a, miR-31 (FIG. 10) and others (data not shown) were each significantly expressed by real-time RT-PCR assays using RNA derived from transgenic malignant (T) versus normal transgenic (N) or Tg− lung tissues. Each assay was conducted at least three independent times with similar results. Results obtained were concordant with findings from miRNA microarray experiments (FIG. 10A and data not shown). The results displayed in FIG. 10A from murine lung tissues are presented because the same miRNAs were also frequently over-expressed in human lung cancers versus adjacent normal lung tissues, as shown in FIG. 10B.

Real-Time RT-PCR Assays

The miRNA RT-PCR assays were performed using the TaqMan miRNA Reverse Transcription Kit (Applied Biosystems, Foster City, Calif.) and the 7500 Fast Real-Time PCR System (Applied Biosystems, Foster City, Calif.) for quantitative miRNA detection, and each miRNA TaqMan PCR probe was purchased from Applied Biosystems, as described (Liu). The real-time RT-PCR assays were performed using the 7500 Fast Real-Time PCR System for quantitative mRNA detection and with the iTaq Fast SYBR Green supermix (BIO-RAD, Hercules, Calif.). TaqMan real-time PCR primer set from Applied Biosystems was use. Control RNA primer wa snoRNA-135 for mouse and RNU6B for human. Taqman Primers: Human miR-31: 4395390, RNU6B: 4373381, Mouse miR-31: 4373331 and SnoRNA-135: 4380912.

Example 9

Over-Expression of miRNAs in Human Lung Cancer

To explore if the identified miRNAs with increased expression in murine lung cancers would also be over-expressed in human lung cancers as compared to adjacent normal lung tissues, paired human normal-malignant lung tissues were examined from each type of non-small cell lung cancers (NSCLC, adenocarcinoma, AD; squamous cell carcinoma, SC; large cell carcinoma, LC; and bronchioalveolar carcinoma, BAC) using a previously described lung tissue bank (Lui, et al and Petty et al). Over-expression of miR-136, miR-376a and miR-31 was frequently detected in each type of NSCLC as compared to adjacent normal lung (FIG. 10B). Each of these highlighted miRNAs was independently examined in the indicated murine and human lung tissues. The other miRNAs identified as differentially over-expressed in murine transgenic lung cancer (FIG. 8) were detected as over-expressed in only a minority of these NSCLC subtypes (data not shown). Of these differentially over-expressed miRNAs, miR-31 was selected for in-depth study.

Human Lung Tissues

Paired human normal and malignant lung tissues were obtained after review and approval of Dartmouth's Institutional Review Board. Patient identifying information was not linked to this tissue bank consecutively accrued over 8 years at Dartmouth-Hitchcock Medical Center.

Example 10

Knock-Down of miR-31 in Lung Cancer Cells

The effect of the highlighted miRNAs on lung cancer cell growth was investigated. Each species was independently transiently engineered with increased or decreased expression in murine lung cancer cell lines (ED-1 and ED-2) as well as in the C10 alveolar type II epithelial cell line. Independent over-expression of miR-136, miR-376a and miR-31 in these cell lines did not appreciably affect murine lung cell growth (data not shown). This was likely due to the high basal levels of these miRNAs in these respective cell lines that prevented eliciting further effects from engineering even higher expression levels. To confirm this, real-time RT-PCR assays were independently conducted (as described above) on these cell lines as well as on murine and human lung cancer tissues to assess the relative levels of the miRNAs of interest as compared to control species (sno-135 for murine cells/tissues and RUN6B for human cells/tissues). Findings revealed that miR-31 expression levels were higher in nearly all these cell lines examined (cancer and normal cell lines) than in murine (FIG. 11A) or human (FIG. 11B) lung cancer tissues.

In contrast, knock-down of miR-31 significantly reduced lung cancer cell growth as compared to controls, as shown in FIG. 12A upper panel, in which miR-31 was independently knocked-down in murine lung cancer cell lines (ED-1 and ED-2) as well as in C10 cells. As displayed in FIG. 12A, ED-1 and ED-2 cell growth was suppressed more than 60% (P<0.0001), while C-10 cell growth was less prominently reduced (P<0.005). Appreciable increase of apoptosis was not observed by knock-down of miR-31 as compared to controls (data not shown). Over 90% of cells from each cell line were transfected (data not shown) and miR-31 levels in each knock-down transfectant was reduced to less than 10% as compared to control transfectants, as confirmed by real-time RT-PCR assays (FIG. 12A, lower panel). It was hypothesized that similar effects would be observed in BEAS-2B human immortalized bronchial epithelial cells versus human lung cancer cell lines. The same transfection experiments were independently conducted in H23 and H226 human lung cancer cell lines as well as in BEAS-2B cells. A significant (P=0.00019 for H23 and P=0.015 for H226) growth suppressive effect was independently caused by knock-down of miR-31 in H23 and H226 cells (FIG. 12A). Intriguingly, proliferation of transfected BEAS-2B cells was not significantly affected by engineered miR-31 knock-down, suggesting a different response to loss of miR-31 expression in human immortalized versus malignant lung epithelial cells. To exclude non-specific transfection effects and to examine whether this growth inhibition was reversible, miR-31 was independently knocked-down in ED-1 and ED-2 cells and growth suppression was examined in these transfectants. Two days after the first transfection, pre-miR-31 or an inactive control pre-miR was transiently over-expressed in these respective cells and growth effects were examined. As expected, engineered over-expression of miR-31 reversed anti-miR-31-mediated growth suppression (FIG. 12B, left panels for each respective transfectant). The miR-31 expression levels in the indicated transfectants were determined by real-time RT-PCR assays (FIG. 12B, right panels for each respective transfectants).

Cell Lines

The murine lung cancer cell lines (ED-1 and ED-2 cells) were derived as described previously from wild-type cyclin E and proteasome-degradation resistant cyclin E transgenic mice, respectively (Luie et al). The C10 murine alveolar type II epithelial cell line and H226, H23, HOP62, H522 and A549 human lung cancer cell lines were each purchased from ATCC. BEAS-2B immortalized human bronchial epithelial cells were kindly provided by Dr. Curtis C. Harris (National Institutes of Health and National Cancer Institute, Bethesda, Md.).

Tissue Culture

ED-1, ED-2, H226, H23, HOP62, H522 and A549 cells were each cultured in RPMI 1640 medium with 10% FBS and 1% antibiotic and antimycotic solution in a humidified incubator at 37° C. in 5% CO2. C10 cells were cultured in CMRL 1066 medium (Life Technologies, Grand Island, N.Y.) with 10% FBS, 2 mM L-glutamine, 100 units/ml penicillin, and 100 μg/ml streptomycin. BEAS-2B cells were cultured in serum-free LHC-9 medium (Invitrogen, Carlsbad, Calif.).

Transient Transfection

ED-1, ED-2, C10, H23, H226 and BEAS-2B cells were individually plated subconfluently onto each well of 6-well tissue culture plates or 10 cm dishes 24 hours before transfection. Transient transfection of pre-miR miRNA precursors and/or anti-miR and control oligonucleotides (anti-miR-neg or pre-miR-neg) (Ambion, Austin, Tex.) at a final concentration of 50 nM was accomplished with siPORT NeoFX reagent (Ambion, Austin, Tex.) using previously optimized methods (Lui et al). Logarithmically growing transfectants were harvested for independent immunoblot, proliferation, apoptosis, and trypan blue viability assays, as described. Over-expression of miR-31 were obtained using pre-miR-31 (pre-miR-neg as control) from Applied Biosystems. The chemically modified oligonucleotides identified as follows Human Pre-miR-31: AM17100, Mouse pre-miR-31: AM17101 and Pre-miR-neg: AM17110 were used. To knock-down miR-31, anti-miR-31 (anti-miR-neg as control) from Applied Biosystems were used. Human anti-miR-31: AM17000, Mouse anti-miR-31: AM17001 and Anti-miR-neg: AM17010.

Example 11

Knock-Down of miR-31 Represses In Vivo Tumorigenicity

To examine if this growth inhibitory effect of mrR-31 knock down causes reduced clonal growth of lung cancer cells colony formation assays were performed. Independent knock-down of miR-31 significantly reduced ED-1 and ED-2 colony formation assays, as shown in FIG. 13A. The colony numbers for anti-miR-31 transfectants whereas significantly less than for the control groups, with P=0.018 for ED-1 cells and P=0.0002 for ED-2 cells, respectively. To examine whether the observed repression of lung cancer cell clonal growth was associated with in vivo repression of tumorigenicity, syngeneic FVB mice were tail-vein injected with ED-1 cells (see the Materials and Methods) that were transiently transfected with anti-miR-31 to achieve knock-down of miR-31. Results were compared to control transfectants. Twenty-five days after tail-vein injections, lung lesions were scored. As displayed in FIG. 13B, ED-1 cells transfected with anti-miR-31 produced significantly fewer (P=0.05) lung lesions as compared to ED-1 control transfectants. The knock-down of miR-31 by transient transfection persisted for approximately 6 days while the outgrowth of lung lesions occurred typically by 7-15 days post injection (data not shown).

Proliferation and Colony Formation Assays

The CellTiter-Glo proliferation assay (Promega, Madison, Wis.) was used along with previously optimized methods (Lui et al). The colony formation assay was performed with 2.5×102 ED-1 cells or 5×102 ED-2 cells or the indicated transfectants independently plated onto 10 cm tissue culture plates. After 10 days, visible colonies were fixed and stained with Diff-Quik solution (Baxtor, Deerfield, Ill.) and quantified using the Col Count instrument (Oxford Optronix, UK), as described (Lui et al).

In Vivo Tumorigenicity and Statistical Assays

Early passages of ED-1 cells were harvested in PBS supplemented with 10% mouse serum (Invitrogen, Carlsbad, Calif.) and 106 cells of each transfectant of this cell line were individually injected into tail veins of each respective FVB syngeneic mouse. In each experimental arm 10 control mice tail vein-injected with control transfected ED-1 cells and 10 mice tail vein-experimental injected with miR-31 (miR-31 knock-down ED-1 transfectants) mice were used. With a replicate experiment, a total of 40 mice were examined. Post-injection (17 days) mice were sacrificed following an Institution Animal Care and Use Committee (IACUC) approved protocol and harvested lung tissues were formalin-fixed, paraffin-embedded, sectioned as well as hematoxylin and eosin stained for histopathologic analyses using optimized methods (Ma et al). Histopathologic sections were scored for lung tumors by a pathologist (H.L.), who was unaware of the treatment arms being analyzed. The log transformation of these data was used to eliminate the skewness of counts with the subsequent application of the two-tail t-test for comparison of the number of lung lesionsfoci in the FVB mice injected with anti-miR-neg versus anti-miR-31 transfectants. The difference was scored as statistically significant if the p-value was 0.05 or less. For an alternative statistical analysis, the likelihood-ratio test was used with the assumption that counts follow a Poisson distribution. Computations were conducted using the statistical package S-Plus 6.1 (Insightful Inc., Seattle, Wash.).

Example 12

Bioinformatic mRNA Targets

Bioinformatic analyses were performed to search for miR-31target mRNAs. The PicTar, TargetScan 4.0 and online miRNA target prediction programs (http COLON SLASH SLASH cbio DOT mskcc DOT org/cgi-bin/mirnaviewer/mirnaviewer.pl) (Hyperlink deactivated) were each used to independently predict miR-31targets. It is apparent that each miRNA can affect multiple targets via distinct mechanisms. Given this, attention focused on finding candidate tumor suppressive genes that could exert miR-31 growth inhibitory effects. Several candidates were highlighted across each bioinformatic program used. These were LATS2, PPP2R2A, Frizzled homolog 3 (FZD3), Sprouty-related, EVH1domain containing 1 (SPRED1), Sprouty homolog 4 (SPRY4), AXIN1up-regulated 1 (AXUD1), and DICER1. The miR-31 targets sought were those that were repressed by forced miR-31 over-expression and augmented by its engineered knock-down. Among these candidates, only LATS2 and PPP2R2A satisfied this criterion, as shown in FIG. 14A and 14B, respectively. All six cell lines (ED-1, ED-1, C10, H23, H226 and BEAS-2B) were independently examined in these analyses and each of them exhibited concordant results.

LATS2, human large tumor suppressor homolog 2 (also known as KPM), is a member of LATS tumor suppressor family. PPP2R2A, also known as protein phosphatase 2A B55 subunit act as a tumor suppressor by induction of apoptosis.

To functionally determine whether these species are targets of miR-31, LATS2 and PPP2R2A were individually knocked-down by siRNAs in ED-1 cells 48 hours after the initial transfection that conferred miR-31 repression (as described above in example 10). As expected, siRNA knock-down of LATS2 and PPP2R2A each antagonized the growth suppression caused by engineered miR-31 repression (FIG. 15A). Two independently designed siRNAs were used to target LATS2 and PPP2R2A and each experiment was conducted in triplicate at least three independent times. Compared with control siRNA, LATS2 siRNAs and PPP2R2A siRNAs repressed the desired target mRNA levels to 5-6% of basal levels as examined by real-time RT-PCR assays (FIG. 15B). These results demonstrated that repression of LATS2 and PPP2R2A expression antagonized growth suppression caused by miR-31 knock-down and functionally validated them as miR-31 targets. Similar results were independently obtained in experiments with ED-2 cells, as shown in FIGS. 15C and 15D.

The siRNA transfections were conducted following the same procedure as for a pre-miR and used at a final concentration of 25 nM (see above in relation to example 10). The Silencer Select Pre-designed siRNAs were purchased from Applied Biosystems (Foster City, Calif.) and LATS2 siRNAs (s78350 and s78351), PPP2R2A siRNAs (s90396 and s90395) and a negative control siRNA (4390843) wereas also used in these experiments.

Example 13

LATS2 and PPP2R2A Expression in Lung Cancers

Since miR-31 was over-expressed in both murine cyclin E transgenic lung cancer models and in human lung cancer tissues, we sought to determine whether LATS2 and PPP2R2A were each basally repressed in these lung cancers relative to adjacent normal lung tissues. Real-time RT-PCR assays were conducted on murine cyclin E transgenic lung adenocarcinomas and adjacent normal lung tissues, as well as in previously studied paired human normal-malignant lung tissues (Lui et al). Both LATS2 and PPP2R2A were each basally repressed in these murine cyclin E transgenic lung cancers, with mRNA levels substantially reduced as compared to adjacent normal lung tissues, as in FIGS. 16A and 16B. As expected, LATS2 and PPP2R2A expression was also repressed in all examined human lung cancers relative to adjacent normal tissues, as shown in FIGS. 16C and 16D. These results underscore that concordant expression profiles were found for miR-31 and its target mRNAs in both murine and human lung cancers.

Real-Time RT-PCR Assays were beformed as described above inrelation to example 8 using the below primers for amplification.

```
human GAPDH:
SEQ ID NO 38,     5'-ATGGGGAAGGTGAAGGTCG-3'
(forward) and

SEQ ID NO 39,     5'-GGGGTCATTGATGGCAACAATA-3'
(reverse);

human PPP2R2A:
SEQ ID NO 40,     5'-TCGGATGTAAAATTCAGCCA-3'
(forward) and
```

```
SEQ ID NO 41,     5'-CATGCACCTGGTATGTTTCC-3'
(reverse);

human LATS2:
SEQ ID NO 42,     5'-CAGATTCAGACCTCTCCCGT-3'
(forward) and

SEQ ID NO 43,     5'-CTTAAAGGCGTATGGCGAGT-3'
(reverse);

mouse GAPDH:
SEQ ID NO 44,     5'-AGGTCGGTGTGAACGGATTTG-3'
(forward) and

SEQ ID NO 45,     5'-TGTAGACCATGTAGTTGAGGTCA-3'
(reverse);

mouse LATS2:
SEQ ID NO 46,     5'-AGCAGATTGTGCGAGTCATC-3'
(forward) and

SEQ ID NO 47,     5'-GTGGTAGGATGGGAGTGCTT-3'
(reverse);

mouse PPP2R2A:
SEQ ID NO 48,     5'-TAAGAGAGCGGTCCATTGTG-3'
(forward) and

SEQ ID NO 49,     5'-ACAGCTTTCTCCATGAGGCT-3'
(reverse)
```

REFERENCES

Abelson, J. F., Kwan, K. Y., O'Roak, B. J., Baek, D. Y., Stillman, A. A., Morgan, T. M., Mathews, C. A., Pauls, D. L., Rasin, M. R., Gunel, M., Davis, N. R., Ercan-Sencicek, A. G., Guez, D. H., Spertus, J. A., Leckman, J. F., Dure, L. S. 4th, Kurlan, R, Singer, H. S., Gilbert, D. L., Farhi, A., Louvi, A., Lifton, R. P., Sestan, N., State, M. W. 2005. Sequence variants in SLITRK1 are associated with Tourette's syndrome. Science 310: 317-20.

Aboobaker, A. A., Tomancak, P., Patel, N., Rubin, G. M., Lai, E. C. 2005. Drosophila microRNAs exhibit diverse spatial expression patterns during embryonic development. Proc Natl Acad Sci USA. 102:18017-22.

't Veer, L. J., Dai, H., van de Vijver, M. J., He, Y. D., Hart, A. A., Mao, M., Peterse, H. L., van der, K. K., Marton, M. J., Witteveen, A. T., Schreiber, G. J., Kerkhoven, R. M., Roberts, C., Linsley, P. S., Bernards, R., and Friend, S. H. (2002). Gene expression profiling predicts clinical outcome of breast cancer. Nature 415, 530-536.

Altuvia, Y., Landgraf, P., Lithwick, G., Elefant, N., Pfeffer, S., Aravin, A., Brownstein, M. J., Tuschl, T., Margalit, H.2005. Clustering and conservation patterns of human microRNAs. Nucleic Acids Res. 33: 2697-706.

Barad, O., Meiri, E., Avniel, A., Aharonov, A., Barzilai, A., Bentwich, I., Einav, U., Gi-lad, S., Hurban, P., Karov, Y., Lobenhofer, E. K., Sharon, E., Shiboleth, Y. M., Shtutman, M., Bentwich, Z., and Einat, P. 2004. MicroRNA expression detected microarrays: System establishment profiling in human tissues. Genome Research 14: 2486-2494.

Bartel, D. P. 2004. MicroRNAs: Genomics, biogenesis, mechanism and function. Cell 116: 281-297.

Bentwich, I., Avniel, A., Karov, Y., Aharonov, R., Gilad, S., Barad, O., Barzilai, A., Einat, P., Einav, U., Meiri, E., Sharon, E., Spector, Y. and Bentwich, Z. 2005. Identification of hundreds of conserved and nonconserved human microRNAs. Nat. Genet. 37: 766-770.

Berezikov, E., Guryev, V., van de Belt, J., Wienholds, E., Plasterk, R. H. A. and Cuppen, E. 2005. Phylogenetic shadowing and computational identification of human microRNA genes. Cell 120: 21-24

Boehm, M., Slack, F. 2005. A developmental timing microRNA and its target regulate life span in C. elegans. Science. 310:1954-7.

Brennecke, J., Hipfner, D. R., Stark, A., Russel, R. B. and Cohen S. 2003. bantam encodes a developmentally regulated microRNA that controls cell proliferation and regulates the proapoptotic gene hid in Drosophila. Cell 113: 25-36.

Brennecke, J., Stark, A., Russel, R. B. and Cohen S 2005. Principles of MicroRNA-target recognition. PLoS Biology 3: e85

Calin, G. A., Sevignani, C., Dumitru, C. D., Hyslop, T., Noch, E., Yendamuri, S., Shimizu, M., Rattan, S., Bullrich, F., Negrini, M. and Croce, C. M. 2004. Human microRNA genes are frequently located at fragile sites and genomic regions involved in cancers. Proc. Natl. Acad. Sci.U.S.A. 101: 2999-3004.

Calin, G. A., Dumitru, C. D., Shimizu, M., Bichi, R., Zupo, S., Noch, E., Aldler, H., Rattan, S., Keating, M., Rai, K., Rassenti, L., Kipps, T., Negrini, M., Bullrich, F. and Croce, C. M. 2002. Frequent deletions and downregulation of microRNA genes miR15 and miR16 at 13q14 in chronic lymphocytic leukemia. Proc. Natl. Acad. Sci. USA 99: 15524-15529.

Calin, G. A., Ferracin, M., Cimmino, A., Di Leva, G., Shimizu, M., Wojcik, S. E., Iorio, M. V., Visone, R., Sever, N. I., Fabbri, M., Iuliano, R., Palumbo, T., Pichiorri, F., Roldo, C., Garzon, R., Sevignani, C., Rassenti, L., Alder, H., Volinia, S., Liu, C. G., Kipps, T. J., Negrini, M., Croce, C. M. 2005. A MicroRNA signature associated with prognosis and progression in chronic lymphocytic leukemia. N. Engl. J. Med. 353:1793-801

Chan, J. A., Krichevsky, A. M., Kosik, K. S. 2005. MicroRNA-21 is an antiapoptotic factor in human glioblastoma cells. Cancer Res. 65:6029-33.

Chen, C. Z., Li, L., Lodish, H. F. and Bartel, D. P. 2004. MicroRNAs modulate hematopoietic lineage differentiation. Science 303: 83-86.

Chen, X. 2004. A MicroRNA as a translational repressor of APETALA2 in Arabidopsis flower development. Science 203: 2022-2025;

Chen, J. F., Mandel, E. M., Thomson, J. M., Wu, Q., Callis, T. E., Hammond, S. M., Conlon, F. L., Wang, D. Z. 2005. The role of microRNA-1 and microRNA-133 in skeletal muscle proliferation and differentiation. Nat Genet. December 25, advance online publication.

Colozza, M., Cardoso, F., Sotiriou, C., Larsimont, D., and Piccart, M. J. (2005). Bringing molecular prognosis and prediction to the clinic. Clin. Breast Cancer. 6, 61-76.

Eis, P. S., Tam, W., Sun, L., Chadburn, A., Li, Z., Gomez, M. F., Lund, E., Dahlberg, J. E. 2005. Accumulation of miR-155 and BIC RNA in human B cell lymphomas. Proc Natl Acad Sci USA. 102: 3627-32.

Farh, K. K., Grimson, A., Jan, C., Lewis, B. P., Johnston, W. K., Lim, L. P., Burge, C. B., Bartel, D. P. 2005. The widespread impact of mammalian MicroRNAs on mRNA repression and evolution. Science. 310:1817-21.

Giraldez, A. J., Cinalli, R. M., Glasner, M. E., Enright, A. J., Thomson, J. M., Baskerville, S., Hammond, S. M., Bartel, D. P. and Schier, A. F. 2005. MicroRNAs regulate brain morphogenesis in zebrafish. Science 308: 833-838.

Griffiths-Jones, S. 2004. The microRNA Registry. Nucleic Acids Res. 32: D109-D111.

Griffiths-Jones, S., Grocock, R. J., van Dongen, S., Bateman, A., Enright, A. J. 2006. miRBase: microRNA sequences, targets and gene nomenclature. Nucleic Acids Res. 34: D140-4

He, L., Thomson, J. M., Hemann, M. T., Hernando-Monge, E., Mu, D., Goodson, S., Powers, S., Cordon-Cardo, C., Lowe, S. W., Hannon, G. J. and Hammond, S. M. 2005. A microRNA polycistron as a potential human oncogene. Nature 435: 828-833.

Hornstein, E., Mansfield, J. H., Yekta, S., Hu, J. K., Harfe, B. D., McManus, M. T., Baskerville. S., Bartel, D. P., Tabin, C. J. 2005. The microRNA miR-196 acts upstream of Hoxb8 and Shh in limb development. Nature 438: 671-4.

Huber, W., Heydebreck, A., Sultmann, H., Poustka, A., and Vingron, M. (2002) Variance stabilization applied to microarray data calibration and to quantification of differential expression. Bioinformatics 18: 96-104.

Hutvagner, G., McLachlan, J., Pasquinelli, A. E., Balint, E., Tuschl, T. and Zamore, P. D. 2001. A cellular function for the RNA-interference enzyme Dicer in the maturation of the let-7 small temporal RNA. Science 293: 834-838.

Hutvágner, G., Simard, M. J., Mello, C. C. and Zamore, P. D. 2004. Sequence-specific inhibition of small RNA function. PLoS Biology 2: 1-11.

Jin, P., Alisch, R. S., Warren, S. T. 2004. RNA and microRNAs in fragile X mental retardation. Nat Cell Biol. 6: 1048-53.

Johnson, S. M., Grosshans, H., Shingara, J., Byrom, M., Jarvis, R., Cheng, A., Labourier, E., Reinert, K. L., Brown, D. and Slack, F. J. 2005. RAS is regulated by the let-7 microRNA family. Cell 120: 635-647.

Johnston, R. J. and Hobert, O. 2003. A microRNA controlling left/right neuronal asymmetry in *Caenorhabditis elegans*. Nature 426: 845-849.

Jopling, C. L., Yi, M., Lancaster, A. M., Lemon, S. M., Sarnow, P. 2005. Modulation of hepatitis C virus RNA abundance by a liver-specific MicroRNA. Science 309:1577-81.

Ketting, R. F., Fischer, S. E., Bernstein, E., Sijen, T., Hannon, G. J. and Plasterk, R. H. 2001. Dicer functions in RNA interference and in synthesis of small RNA involved in developmental timing in *C. elegans*. Genes Dev. 15: 2654-2659.

Kim, J., Krichevsky, A., Grad, Y., Hayes, G. D., Kosik, K. S., Church, G. M., Ruvkun, G. 2004. Identification of many microRNAs that copurify with polyribosomes in mammalian neurons. Proc Natl Acad Sci USA. 101: 360-5.

Krek, A., Grun, D., Poy, M. N., Wolf, R., Rosenberg, L., Epstein, E. J., MacMenamin, P., da Piedade, I., Gunsalus, K. C., Stoffel, M. and Rajewsky, N. 2005. Combinatorial microRNA target predictions. Nat. Genet. 37: 495-500.

Krichevsky, A. M., King, K. S., Donahue, C. P., Khrapko, K. and Kosik, K. S. 2003. A microRNA array reveals extensive regulation of microRNAs during brain development. RNA 9: 1274-1281.

Krützfeldt, J., Rajewsky, N., Braich, R., Rajeev, K. G., Tuschl, T., Manoharan, M. and Stoffel, M. 2005. Silencing of microRNAs in vivo with 'antagomirs'. Nature 438: 685-9.

Kwon, C., Han, Z., Olson, E. N., Srivastava, D. 2005. MicroRNA1 influences cardiac differentiation in *Drosophila* and regulates Notch signaling. Proc Natl Acad Sci USA. 102: 18986-91.

Lagos-Quintana, M., Rauhut, R., Lendeckel, W. and Tuschl, T. 2001. Identification of novel genes coding for small expressed RNAs. Science 294: 853-858.

Landthaler, M., Yalcin, A. and Tuschl, T. 2004. The human DiGeorge syndrome critical region gene 8 and its *D. melanogaster* homolog are required for miRNA biogenesis. Curr. Biol. 14: 2162-2167.

Leaman, D., Chen, P, Y., Fak, J., Yalcin, A., Pearce, M., Unnerstall, U., Marks, D. S., Sander, C., Tuschl, T., Gaul, U. 2005. Antisense-mediated depletion reveals essential and specific functions of microRNAs in *Drosophila* development. Cell 121: 1097-108.

Lee, R. C. and Ambros, V. 2001. An extensive class of small RNAs in *Caenorhabditis elegans*. Science 294: 862-864.

Lee, R. C., Feinbaum, R. L. and Ambros, V. 1993. The *C. elegans* heterochronic gene lin-4 encodes small RNAs with antisense complementarity to lin-14. Cell 75: 843-854.

Lee, Y., Ahn, C., Han, J., Choi, H., Kim, J., Yim, J., Lee, J., Provost, P., Radmark, O., Kim, S, and Kim, V. N. 2003. The nuclear RNase III Drosha initiates microRNA processing. Nature 425: 415-419.

Lewis, B. P., Burge, C. B., Bartel, D. P. 2005. Conserved seed pairing, often flanked by adenosines, indicates that thousands of human genes are microRNA targets. Cell 120: 15-20.

Li, X. and Carthew, R. W. 2005. A microRNA mediates EGF receptor signaling and promotes photoreceptor differentiation in the *drosophila* eye. Cell 123: 1267-77.

Liu, X., Sempere, L. F., Galimberti, F., Freemantle, S. J., Black, C., Dragnev, K. H., Ma, Y., Fiering, S., Memoli, V., Li, H., et al. 2009. Uncovering growth-suppressive MicroRNAs in lung cancer. Clin Cancer Res 15:1177-1183.

Lim, L. P., Lau, N. C., Garrett-Engele, P., Grimson, A., Schelter, J. M., Castle, J., Bartel, D. P., Linsley, P. S., and Johnson, J. M. 2005. Microarray analysis shows that some microRNAs downregulate large numbers of target mRNAs. Nature 433: 769-773.

Liu, C-G., Calin, G. A., Meloon, B., Gamliel, N., Sevignani, G., Ferracin, M., Dumitru, C. M., Shimizu, M., Zupo, S., Dono, M., Alder, H., Bullrich, F., Negrini, M. and Croce, C. M. 2004. An oligonucleotide microchip for genome-wide microRNA profiling in human and mouse tissues. Proc. Natl. Acad. Sci, U.S.A 101:9740-9744, Lu. J., Getz, G., Miska, E. A., Alvarez-Saavedra, E. A., Lamb, J., Peck, D., Sweet-Cordero, A., Ebert, B. L., Mak, R. H., Ferrando, A. A., Downing, J. R., Jacks, T., Horvitz, H. R., and Golub, T. R. 2005. MicroRNA expression profiles classify human cancers. Nature 435: 834-838.

Ludwig, J. A. and Weinstein, J. N. (2005). Biomarkers in cancer staging, prognosis and treatment selection. Nat. Rev. Cancer. 5, 845-856.

Ma, Y., Fiering, S., Black, C., Liu, X., Yuan, Z., Memoli, V. A., Robbins, D. J., Bentley, H. A., Tsongalis, G. J., Demidenko, E., et al. 2007. Transgenic cyclin E triggers dysplasia and multiple pulmonary adenocarcinomas. Proc Natl Acad Sci USA 104:4089-4094.

Michael, M. Z., SM, O. C., van Holst Pellekaan, N. G., Young, G. P. and James, R. J. 2003. Reduced accumulation of specific microRNAs in colourectal neoplasia. Mol. Cancer Res. 1: 882-891.

Nelson, P., Kiriakidou, M., Sharma, A., Maniataki, E. and Mourelatos, Z. 2003. The microRNA world: small is mighty. TIBS 28: 534-540.

Petty, W. J., Li, N., Biddle, A., Bounds, R., Nitkin, C., Ma, Y., Dragnev, K. H., Freemantle, S. J., and Dmitrovsky, E. 2005. A novel retinoic acid receptor beta isoform and retinoid resistance in lung carcinogenesis. J Natl Cancer Inst 97:1645-1651.

Ocana, A., Cruz, J. J., and Pandiella, A. (2006). Trastuzumab and antiestrogen therapy: focus on mechanisms of action and resistance. Am. J. Clin. Oncol. 29, 90-95.

Paushkin, S., Gubitz, A. K., Massenet, S. and Dreyfuss, G. 2002. The SMN complex, an assemblyosome of ribonucleoproteins. Curr. Opin. Cell Biol. 14: 305-312.

Perou, C. M., Jeffrey, S. S., van de, R. M., Rees, C. A., Eisen, M. B., Ross, D. T., Pergamenschikov, A., Williams, C. F., Zhu, S. X., Lee, J. C., Lashkari, D., Shalon, D., Brown, P. O., and Botstein, D. (1999). Distinctive gene expression patterns in human mammary epithelial cells and breast cancers. Proc. Natl. Acad. Sci. U.S. A 96, 9212-9217.

Poy, M. N., Eliasson, L., Krutzfeldt, J., Kuwajima, S., Ma, X., Macdonald, P. E., Pfeffer, S., Tuschl, T., Rajewsky, N., Rorsman, P. and Stoffel, M. (2004) A pancreatic islet-specific microRNA regulates insulin secretion. Nature 432: 226-230.

Reinhart, B. J., Slack, F. J., Basson, M., Bettinger, J. C., Pasquinelli, T., Rougvie, A. E., Horvitz, H. R., and Ruvkun, G. 2000. The 21 nucleotide let-7 RNA regulates developmental timing in Caenorhabditis elegans. Nature 403: 901-906.

Reinhart, B. J., Weinstein, E. G., Rhoades, M. W., Bartel, B., and Bartel, D. P. 2002. MicroRNAs in plants. Genes Dev. 16: 1616-1626.

Rodriguez, A., Griffiths-Jones, S., Ashurst, J. L., Bradley, A. Related 2004. Identification of mammalian microRNA host genes and transcription units. Genome Res. 10A: 1902-10.

Saeed, A. I., Sharov, V., White, J., Li, J., Liang, W., Bhagabati, N., Braisted, J., Klapa, M., Currier, T., Thiagarajan, M., Sturn, A., Snuffin, M., Rezantsev, A., Popov, D., Ryltsov, A., Kostukovich, E., Borisovsky, I., Liu, Z., Vinsavich, A., Trush, V., and Quackenbush, J. (2003).

TM4: a free, open-source system for microarray data management and analysis. Biotechniques 34, 374-378.

Seitz, H., Royo, H., Bortolin, M. L., Lin, S. P., Ferguson-Smith, A. C., Cavaille, J. 2004. A large imprinted microRNA gene cluster at the mouse Dlk1-Gtl2 domain. Genome Res. 9:1741-8.

Sempere, L. F., Christensen, M., Silahtaroglu, A., Bak, M., Heath, C. V., Schwartz, G., Wells, W., Kauppinen, S., and Cole, C. N. 2007. Altered MicroRNA expression confined to specific epithelial cell subpopulations in breast cancer. Cancer Res 67:11612-11620.

Smirnova, L., Grafe, A., Seiler, A., Schumacher, S., Nitsch, R. and Wulczyn, F. G. 2005. Regulation of miRNA expression during neural cell specification. Eur J Neurosci. 21: 1469-77.

Sokol, N. S., Ambros, V. 2005. Mesodermally expressed Drosophila microRNA-1 is regulated by Twist and is required in muscles during larval growth. Genes Dev. 19: 2343-54.

Sorlie, T. (2004). Molecular portraits of breast cancer: tumour subtypes as distinct disease entities. Eur. J. Cancer. 40, 2667-2675.

Sorlie, T., Perou, C. M., Tibshirani, R., Aas, T., Geisler, S., Johnsen, H., Hastie, T., Eisen, M. B., van de, R. M., Jeffrey, S. S., Thorsen, T., Quist, H., Matese, J. C., Brown, P. O., Botstein, D., Eystein, L. P., and Borresen-Dale, A. L. (2001). Gene expression patterns of breast carcinomas distinguish tumour subclasses with clinical implications. Proc. Natl. Acad. Sci. U.S.A. 98, 10869-10874.

Sorlie, T., Tibshirani, R., Parker, J., Hastie, T., Marron, J. S., Nobel, A., Deng, S., Johnsen, H., Pesich, R., Geisler, S., Demeter, J., Perou, C. M., Lonning, P. E., Brown, P. O., Borresen-Dale, A. L., and Botstein, D. (2003). Repeated observation of breast tumour subtypes in independent gene expression data sets. Proc. Natl. Acad. Sci. U.S.A 100, 8418-8423.

Stark, A., Brennecke, J., Bushati, N., Russell, R. B., Cohen, S. M. 2005. Animal MicroRNAs confer robustness to gene expression and have a significant impact on 3'UTR evolution. Cell 123: 1133-46.

Wienholds, E., Kloosterman, W. P., Miska, E., Alvarez-Saavedra, E., Berezikov, E., de Bruijn, E., Horvitz, H. R., Kauppinen, S. and Plasterk, R. H. A. 2005. MicroRNA expression in zebrafish embryonic development. Science 309: 310-311.

Xie, X., Lu, J., Kulbokas, E. J., Golub, T. R., Mootha, V., Lindblad-Toh, K., Lander, E. S. and Kellis, M. 2005. Systematic discovery of regulatory motifs in human promoters and 30 UTRs by comparison of several mammals. Nature 434: 338-345.

Yekta, S., Shih, I-s and Bartel, D. 2004. microRNA-Directed Cleavage of HOXB8 mRNA. Science 304: 594-596.

Zhao, Y., Samal, E. and Srivastava, D. 2005. Serum response factor regulates a muscle-specific microRNA that targets Hand2 during cardiogenesis. Nature 436: 214-220.

---

The invention claimed is:

1. A pharmaceutical composition comprising
   a) an oligonucleotide that down-regulates the over-expression of the miRNA or pre-miRNA of SEQ ID NO:25 in lung cancer, wherein said oligonucleotide is:
      i) complementary to the nucleotide sequence of SEQ ID NO:25, or
      ii) hybridizes under stringent conditions to a nucleotide sequence of i) or the nucleotide sequence of SEQ ID NO:25; and
   b) a second active ingredient for prophylactic or therapeutic treatment of lung cancer.

2. The pharmaceutical composition of claim 1, wherein the oligonucleotide is chemically modified.

3. A method for treating, preventing or reducing the risk of lung cancer associated with aberrant expression of a pre-miRNA and/or miRNA in a cell, tissue or animal comprising contacting the cell, tissue or animal with the pharmaceutical composition according to claim 1.

4. The method of claim 3, wherein the pharmaceutical composition is administered to an individual in need in a therapeutically effective amount.

5. The method of claim 4, wherein the animal is a human being.

6. The method of claim 3, wherein the oligonucleotide is administered by pulmonary administration.

7. The method of claim 3, where the aberrant expression is up-regulation of a miRNA.

8. The method of claim 7, where the oligonucleotide is capable of reducing expression of a miRNA by at least 50%.

* * * * *

SEQUENCE LISTING

```
<160> NUMBER OF SEQ ID NOS: 49

<210> SEQ ID NO 1
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-451 mature

<400> SEQUENCE: 1
aaaccguuac cauuacugag uuu                                            23

<210> SEQ ID NO 2
<211> LENGTH: 22
<212> TYPE: RNA
<213> ORGANISM: Homo sapiens
<220> FEATURE:
```

```
<221> NAME/KEY: misc_feature
<223> OTHER INFORMATION: hsa-miR-143 mature

<400> SEQUENCE: 2
ugagaugaag cacuguagcu ca                                              22

<210> SEQ ID NO 3
<211> LENGTH: 24
<212> TYPE: RNA
<213> ORGANISM: Homo sapiens
<220> FEATURE:
<221> NAME/KEY: misc_feature
<223> OTHER INFORMATION: hsa-miR-145 mature

<400> SEQUENCE: 3
guccaguuuu cccaggaauc ccuu                                            24

<210> SEQ ID NO 4
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-141 mature

<400> SEQUENCE: 4
uaacacuguc ugguaaagau gg                                              22

<210> SEQ ID NO 5
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-200b mature

<400> SEQUENCE: 5
uaauacugcc ugguaaugau gac                                             23

<210> SEQ ID NO 6
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-200c mature

<400> SEQUENCE: 6
uaauacugcc ggguaaugau gg                                              22

<210> SEQ ID NO 7
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-221 mature

<400> SEQUENCE: 7
agcuacauug ucugcugggu uuc                                             23

<210> SEQ ID NO 8
<211> LENGTH: 24
<212> TYPE: RNA
<213> ORGANISM: Homo sapiens
<220> FEATURE:
<221> NAME/KEY: misc_feature
<223> OTHER INFORMATION: hsa-miR-222 mature
```

```
<400> SEQUENCE: 8
agcuacaucu ggcuacuggg ucuc                                        24

<210> SEQ ID NO 9
<211> LENGTH: 72
<212> TYPE: RNA
<213> ORGANISM: Homo sapiens
<220> FEATURE:
<221> NAME/KEY: misc_feature
<223> OTHER INFORMATION: hsa-miR-451 precursor

<400> SEQUENCE: 9
cuugggaaug gcaaggaaac cguuaccauu acugaguuua guaaugguaa ugguucucuu    60
gcuauaccca ga                                                       72

<210> SEQ ID NO 10
<211> LENGTH: 106
<212> TYPE: RNA
<213> ORGANISM: Homo sapiens
<220> FEATURE:
<221> NAME/KEY: misc_feature
<223> OTHER INFORMATION: hsa-miR-143 precursor

<400> SEQUENCE: 10
gcgcagcgcc cugucuccca gccugaggug cagugcugca ucucggguca guugggaguc    60
ugagaugaag cacuguagcu caggaagaga gaaguuguuc ugcagc                  106

<210> SEQ ID NO 11
<211> LENGTH: 88
<212> TYPE: RNA
<213> ORGANISM: Homo sapiens
<220> FEATURE:
<221> NAME/KEY: misc_feature
<223> OTHER INFORMATION: hsa-miR-145 precursor

<400> SEQUENCE: 11
caccuugucc ucacggucca guuucccag gaaucccuua gaugcuaaga uggggauucc     60
uggaaauacu guucuugagg ucaugguu                                      88

<210> SEQ ID NO 12
<211> LENGTH: 95
<212> TYPE: RNA
<213> ORGANISM: Homo sapiens
<220> FEATURE:
<221> NAME/KEY: misc_feature
<223> OTHER INFORMATION: hsa-miR-141 precursor

<400> SEQUENCE: 12
cggccggccc uggguccauc uuccaguaca guguuggaug gucuaauugu gaagcccua     60 acacgucug guaaagaugg cucccgggug gguuc                               95

<210> SEQ ID NO 13
<211> LENGTH: 95
<212> TYPE: RNA
<213> ORGANISM: Homo sapiens
<220> FEATURE:
<221> NAME/KEY: misc_feature
<223> OTHER INFORMATION: hsa-miR-200b precursor

<400> SEQUENCE: 13
ccagcucggg cagccguggc caucuuacug ggcagcauug gauggaguca ggucucuaau    60
acugccuggu aaugaugacg gcggagcccu gcacg                              95
```

```
<210> SEQ ID NO 14
<211> LENGTH: 68
<212> TYPE: RNA
<213> ORGANISM: Homo sapiens
<220> FEATURE:
<221> NAME/KEY: misc_feature
<223> OTHER INFORMATION: hsa-miR-200c precursor

<400> SEQUENCE: 14
cccucgucuu acccagcagu guuuggguGC gguugggagu cucuaauacu gccggguaau    60
gauggagg                                                             68

<210> SEQ ID NO 15
<211> LENGTH: 110
<212> TYPE: RNA
<213> ORGANISM: Homo sapiens
<220> FEATURE:
<221> NAME/KEY: misc_feature
<223> OTHER INFORMATION: hsa-miR-221 precursor

<400> SEQUENCE: 15
ugaacaucca ggucuggggc augaaccugg cauacaaugu agauuucugu guucguuagg    60
caacagcuac auugucugcu ggguuucagg cuaccuggaa acauguucuc              110

<210> SEQ ID NO 16
<211> LENGTH: 110
<212> TYPE: RNA
<213> ORGANISM: Homo sapiens
<220> FEATURE:
<221> NAME/KEY: misc_feature
<223> OTHER INFORMATION: hsa-miR-222 precursor

<400> SEQUENCE: 16
gcugcuggaa gguguaggua cccucaaugg cucaguagcc aguguagauc cugucuuucg    60
uaaucagcag cuacaucugg cuacggguc ucugauggca ucuucuagcu               110

<210> SEQ ID NO 17
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-21 mature

<400> SEQUENCE: 17
uagcuuauca gacugauguu ga                                             22

<210> SEQ ID NO 18
<211> LENGTH: 72
<212> TYPE: RNA
<213> ORGANISM: Homo sapiens
<220> FEATURE:
<221> NAME/KEY: misc_feature
<223> OTHER INFORMATION: hsa-miR-21 precursor

<400> SEQUENCE: 18
ugucggguag cuuaucagac ugauguugac uguugaaucu cauggcaaca ccagucgaug    60
ggcugucuga ca                                                        72

<210> SEQ ID NO 19
<211> LENGTH: 23
<212> TYPE: RNA
<213> ORGANISM: Homo sapiens
<220> FEATURE:
<221> NAME/KEY: misc_feature
```

```
<223> OTHER INFORMATION: hsa-miR-34b mature

<400> SEQUENCE: 19
uaggcagugu cauuagcuga uug                                           23

<210> SEQ ID NO 20
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-34c mature

<400> SEQUENCE: 20
aggcagugua guuagcugau ugc                                           23

<210> SEQ ID NO 21
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-142-3p mature

<400> SEQUENCE: 21
uguaguguuu ccuacuuuau gga                                           23

<210> SEQ ID NO 22
<211> LENGTH: 20
<212> TYPE: RNA
<213> ORGANISM: Homo sapiens
<220> FEATURE:
<221> NAME/KEY: misc_feature
<223> OTHER INFORMATION: hsa-miR-142-5p mature

<400> SEQUENCE: 22
cauaaaguag aaagcacuac                                               20

<210> SEQ ID NO 23
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-486 mature

<400> SEQUENCE: 23
uccuguacug agcugccccg ag                                            22

<210> SEQ ID NO 24
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-144 mature

<400> SEQUENCE: 24
uacaguauag augauguacu ag                                            22

<210> SEQ ID NO 25
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-31 mature
```

```
<400> SEQUENCE: 25
ggcaagaugc uggcauagcu g                                      21

<210> SEQ ID NO 26
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-127 mature

<400> SEQUENCE: 26
ucggauccgu cugagcuugg cu                                     22

<210> SEQ ID NO 27
<211> LENGTH: 23
<212> TYPE: RNA
<213> ORGANISM: Homo sapiens
<220> FEATURE:
<221> NAME/KEY: misc_feature
<223> OTHER INFORMATION: hsa-miR-136 mature

<400> SEQUENCE: 27
acuccauuug uuuugaugau gga                                    23

<210> SEQ ID NO 28
<211> LENGTH: 21
<212> TYPE: RNA
<213> ORGANISM: Homo sapiens
<220> FEATURE:
<221> NAME/KEY: misc_feature
<223> OTHER INFORMATION: hsa-miR-376a mature

<400> SEQUENCE: 28
aucauagagg aaaauccacg u                                      21

<210> SEQ ID NO 29
<211> LENGTH: 22
<212> TYPE: RNA
<213> ORGANISM: Homo sapiens
<220> FEATURE:
<221> NAME/KEY: misc_feature
<223> OTHER INFORMATION: hsa-miR-150 mature

<400> SEQUENCE: 29
ucucccaacc cuuguaccag ug                                     22

<210> SEQ ID NO 30
<211> LENGTH: 23
<212> TYPE: DNA
<213> ORGANISM: Homo sapiens
<220> FEATURE:
<221> NAME/KEY: misc_feature
<223> OTHER INFORMATION: miR-451 probe

<400> SEQUENCE: 30
aaactcagta atggtaacgg ttt                                    23

<210> SEQ ID NO 31
<211> LENGTH: 22
<212> TYPE: DNA
<213> ORGANISM: Homo sapiens
<220> FEATURE:
<221> NAME/KEY: misc_feature
<223> OTHER INFORMATION: miR-21 probe

<400> SEQUENCE: 31
```

```
tcaacatcag tctgataagc ta                                              22
```

<210> SEQ ID NO 32
<211> LENGTH: 21
<212> TYPE: DNA
<213> ORGANISM: Homo sapiens
<220> FEATURE:
<221> NAME/KEY: misc_feature
<223> OTHER INFORMATION: miR-141 probe

<400> SEQUENCE: 32

```
ccatctttac cagacagtgt t                                               21
```

<210> SEQ ID NO 33
<211> LENGTH: 23
<212> TYPE: DNA
<213> ORGANISM: Homo sapiens
<220> FEATURE:
<221> NAME/KEY: misc_feature
<223> OTHER INFORMATION: miR-200b probe

<400> SEQUENCE: 33

```
gtcatcatta ccaggcagta tta                                             23
```

<210> SEQ ID NO 34
<211> LENGTH: 23
<212> TYPE: DNA
<213> ORGANISM: Homo sapiens
<220> FEATURE:
<221> NAME/KEY: misc_feature
<223> OTHER INFORMATION: miR-221 probe

<400> SEQUENCE: 34

```
gaaacccagc agacaatgta gct                                             23
```

<210> SEQ ID NO 35
<211> LENGTH: 24
<212> TYPE: DNA
<213> ORGANISM: Homo sapiens
<220> FEATURE:
<221> NAME/KEY: misc_feature
<223> OTHER INFORMATION: miR-222 probe

<400> SEQUENCE: 35

```
tcgatgtaga ccgatgaccc agag                                            24
```

<210> SEQ ID NO 36
<211> LENGTH: 22
<212> TYPE: DNA
<213> ORGANISM: Homo sapiens
<220> FEATURE:
<221> NAME/KEY: misc_feature
<223> OTHER INFORMATION: miR-143 probe

<400> SEQUENCE: 36

```
tgagctacag tgcttcatct ca                                              22
```

<210> SEQ ID NO 37
<211> LENGTH: 24
<212> TYPE: DNA
<213> ORGANISM: Homo sapiens
<220> FEATURE:
<221> NAME/KEY: misc_feature
<223> OTHER INFORMATION: miR-145 probe

<400> SEQUENCE: 37

```
aagggattcc tgggaaaact ggac                                            24
```

```
<210> SEQ ID NO 38
<211> LENGTH: 19
<212> TYPE: DNA
<213> ORGANISM: Homo sapiens
<220> FEATURE:
<221> NAME/KEY: misc_feature
<223> OTHER INFORMATION: Human GAPDH forward

<400> SEQUENCE: 38
atggggaagg tgaaggtcg                                                19

<210> SEQ ID NO 39
<211> LENGTH: 22
<212> TYPE: DNA
<213> ORGANISM: Homo sapiens
<220> FEATURE:
<221> NAME/KEY: misc_feature
<223> OTHER INFORMATION: Human GAPDH reverse

<400> SEQUENCE: 39
ggggtcattg atggcaacaa ta                                            22

<210> SEQ ID NO 40
<211> LENGTH: 20
<212> TYPE: DNA
<213> ORGANISM: Homo sapiens
<220> FEATURE:
<221> NAME/KEY: misc_feature
<223> OTHER INFORMATION: Human PPP2R2A forward

<400> SEQUENCE: 40
tcggatgtaa aattcagcca                                               20

<210> SEQ ID NO 41
<211> LENGTH: 20
<212> TYPE: DNA
<213> ORGANISM: Homo sapiens
<220> FEATURE:
<221> NAME/KEY: misc_feature
<223> OTHER INFORMATION: Human PPP2R2A reverse

<400> SEQUENCE: 41
catgcacctg gtatgtttcc                                               20

<210> SEQ ID NO 42
<211> LENGTH: 20
<212> TYPE: DNA
<213> ORGANISM: Homo sapiens
<220> FEATURE:
<221> NAME/KEY: misc_feature
<223> OTHER INFORMATION: Human LATS2 forward

<400> SEQUENCE: 42
cagattcaga cctctcccgt                                               20

<210> SEQ ID NO 43
<211> LENGTH: 20
<212> TYPE: DNA
<213> ORGANISM: Homo sapiens
<220> FEATURE:
<221> NAME/KEY: misc_feature
<223> OTHER INFORMATION: Human LATS2 reverse

<400> SEQUENCE: 43
cttaaaggcg tatggcgagt                                               20

<210> SEQ ID NO 44
```

```
<211> LENGTH: 21
<212> TYPE: DNA
<213> ORGANISM: Mus musculus
<220> FEATURE:
<221> NAME/KEY: misc_feature
<223> OTHER INFORMATION: Mouse GAPDH forward

<400> SEQUENCE: 44
aggtcggtgt gaacggattt g                                              21

<210> SEQ ID NO 45
<211> LENGTH: 23
<212> TYPE: DNA
<213> ORGANISM: Mus musculus
<220> FEATURE:
<221> NAME/KEY: misc_feature
<223> OTHER INFORMATION: Mouse GADPH reverse

<400> SEQUENCE: 45
tgtagaccat gtagttgagg tca                                            23

<210> SEQ ID NO 46
<211> LENGTH: 20
<212> TYPE: DNA
<213> ORGANISM: Mus musculus
<220> FEATURE:
<221> NAME/KEY: misc_feature
<223> OTHER INFORMATION: Mouse LATS2 forward

<400> SEQUENCE: 46
agcagattgt gcgagtcatc                                                20

<210> SEQ ID NO 47
<211> LENGTH: 20
<212> TYPE: DNA
<213> ORGANISM: Mus musculus
<220> FEATURE:
<221> NAME/KEY: misc_feature
<223> OTHER INFORMATION: Mouse LATS2 reverse

<400> SEQUENCE: 47
gtggtaggat gggagtgctt                                                20

<210> SEQ ID NO 48
<211> LENGTH: 20
<212> TYPE: DNA
<213> ORGANISM: Mus musculus
<220> FEATURE:
<221> NAME/KEY: misc_feature
<223> OTHER INFORMATION: Mouse PPP2R2A forward

<400> SEQUENCE: 48
taagagagcg gtccattgtg                                                20

<210> SEQ ID NO 49
<211> LENGTH: 20
<212> TYPE: DNA
<213> ORGANISM: Mus Musculus
<220> FEATURE:
<221> NAME/KEY: misc_feature
<223> OTHER INFORMATION: Mouse PPP2R2A reverse

<400> SEQUENCE: 49
acagctttct ccatgaggct                                                20
```